US009371388B2

(12) United States Patent
Nash et al.

(10) Patent No.: US 9,371,388 B2
(45) Date of Patent: *Jun. 21, 2016

(54) HIGH AFFINITY ANTIBODY ANTAGONISTS OF INTERLEUKIN-13 RECEPTOR ALPHA 1

(71) Applicant: CSL Limited, Parkville (AU)

(72) Inventors: Andrew Donald Nash, Kew (AU); Manuel Baca, Gaithersburg, MD (US); Louis Jerry Fabri, Diamond Creek (AU); Dennis Zaller, Scotch Plains, NJ (US); William R. Strohl, Bridgewater, NJ (US); Zhiqiang An, Ambler, PA (US)

(73) Assignee: CSL Limited, Parkville, Victoria (AU)

( * ) Notice: Subject to any disclaimer, the term of this patent is extended or adjusted under 35 U.S.C. 154(b) by 267 days.

This patent is subject to a terminal disclaimer.

(21) Appl. No.: 14/052,791

(22) Filed: Oct. 14, 2013

(65) Prior Publication Data
US 2014/0056915 A1   Feb. 27, 2014

Related U.S. Application Data

(63) Continuation of application No. 12/774,966, filed on May 6, 2010, now Pat. No. 8,568,722, which is a continuation of application No. 11/875,017, filed on Oct. 19, 2007, now Pat. No. 7,754,213.

(60) Provisional application No. 60/852,884, filed on Oct. 19, 2006.

(51) Int. Cl.
*A61K 39/395* (2006.01)
*C07K 16/28* (2006.01)

(52) U.S. Cl.
CPC ......... *C07K 16/2866* (2013.01); *C07K 2317/21* (2013.01); *C07K 2317/33* (2013.01); *C07K 2317/56* (2013.01); *C07K 2317/565* (2013.01); *C07K 2317/71* (2013.01); *C07K 2317/76* (2013.01); *C07K 2317/92* (2013.01); *C07K 2319/43* (2013.01)

(58) Field of Classification Search
None
See application file for complete search history.

(56) References Cited

U.S. PATENT DOCUMENTS

| 6,468,528 B1 | 10/2002 | Mak et al. ............... 424/130.1 |
| 7,135,287 B1 | 11/2006 | Lonberg et al. ............ 435/6.14 |
| 7,754,213 B2 | 7/2010 | Nash et al. ................ 424/142.1 |
| 2005/0058645 A1 | 3/2005 | Dunlop et al. ............. 424/145.1 |
| 2006/0140948 A1 | 6/2006 | Foltz et al. ................ 424/145.1 |

FOREIGN PATENT DOCUMENTS

| EP | 1449851 A1 | 8/2004 |
| WO | WO 97/15663 A1 | 5/1997 |
| WO | WO 03/046009 A1 | 6/2003 |
| WO | WO 03/080675 A2 | 10/2003 |
| WO | WO 2006/072564 A1 | 7/2006 |
| WO | WO 2008/060814 A2 | 5/2008 |

OTHER PUBLICATIONS

Akaiwa et al. "Localization of Human Interleukin 13 Receptor in Non-Haematopoietic Cells" Cytokine 2001 13:75-84.
Aman et al. "cDNA Cloning and Characterization of the Human Interleukin 13 Receptor Alpha Chain" Journal of Biological Chemistry 1996 271:29265-29270.
Brown et al. "Tolerance of Single, But Not Multiple, Amino Acid Replacements in Antibody VH CDR 2: A Means of Minimizing B Cell Wastage from Somatic Hypermutation?" Journal of Immunology 1996 156(9):3285-3291.
Cancino-Diaz et al. "Interleukin-13 Receptor in Psoriatic Keratinocytes: Overexpression of the mRNA and Underexpression of the Protein" The Journal of Investigative Dermatology 2002 119:1114-1120.
Clement et al. "Abstracts: Fifth Annual Conference of the International Cytokine Society" Cytokine Meeting 1997 9(11):959.
Colman, P.M. "Effects of Amino Acid Sequence Changes on Antibody-Antigen Interactions" Research in Immunology 1994 145:33-36.
Damschroder et al. "Analysis of Human and Primate CD2 Molecules by Protein Sequence and Epitope Mapping with Anti-Human CD2 Antibodies" Molecular Immunology 2004 41:985-1000.
GENOVAC "Product Data Sheet Anti-Human IL13 Receptor (IL 13-R) Monoclonal Antibody" Catalog No. GM-0104 http://www.liferesearch.com/media/pdf/genovac/GM-0104.pdf, retrieved May 11, 2010.
Graber et al. "The Distribution of IL-13 Receptor Alpha1 Expression on B Cells, T Cells and Monocytes and Its Regulation by IL-13 and IL-4" European Journal of Immunology 1998 28:4286-4298.
Harlow, E. and Lane, D. "Antibody Structure and Function" *Using Antibodies: A Laboratory Manual* Cold Spring Harbor, New York: Cold Spring Harbor Laboratory Press, 1999 p. 4.
Hilton et al. "Cloning and Characterization of a Binding Subunit of the Interleukin 13 Receptor That Is Also a Component of the Interleukin 4 Receptor" Proceedings of the National Academy of Sciences USA 1996 93:497-501.
Krause et al. "Blockade of Interleukin-13-Mediated Cell Activation by a Novel Inhibitory Antibody to Human IL-13 Receptor Alpha1" Molecular Immunology 2006 43:1799-1807.
Miloux et al. "Cloning of the Human IL-13R Alpha1 Chain and Reconstitution with the IL4R Alpha of a Functional IL-4/IL-13 Receptor Complex" FEBS Letters 1997 401:163-166.

(Continued)

*Primary Examiner* — Zachary Skelding
(74) *Attorney, Agent, or Firm* — Licata & Tyrrell P.C.

(57) ABSTRACT

High affinity antibody antagonists of human interleukin-13 receptor alpha 1 are disclosed. The antibody molecules are effective in the inhibition of IL-13Rα1-mediated activities and, accordingly, present desirable antagonists for the use in the treatment of conditions associated with hIL-13Rα1 activity. The present invention also discloses nucleic acid encoding said antibody molecules, vectors, host cells, and compositions comprising the antibody molecules. Methods of using the antibody molecules for inhibiting or antagonizing IL-13Rα1-mediated activities are also disclosed.

4 Claims, 12 Drawing Sheets

(56) References Cited

OTHER PUBLICATIONS

NCBI Genbank Accession No. U62858 dated Mar. 9, 2000.
NCBI Genbank Accession No. CAA70508 dated Apr. 18, 2005.
NCBI Genbank Accession No. AAP78901 dated Jul. 1, 2003.
Ogata et al. "Regulation of Interleukin-13 Receptor Constituents on Mature Human B Lymphocytes" Journal of Biological Chemistry 1998 273:9864-9871.
Poudrier et al. "A Novel Monoclonal Antibody, C41, Reveals IL-13Ralpha1 Expression by Murine Germinal Center B Cells and Follicular Dendritic Cells" European Journal of Immunology 2000 30:3157-3164.
Rudikoff et al. "Single Amino Acid Substitution Altering Antigen-Binding Specificity" Proceedings of the National Academy of Sciences USA 1982 79:1979-1983.
Vajdos et al. "Comprehensive Functional Maps of the Antigen-Binding Site of an Anti-ErbB2 Antibody Obtained with Shotgun Scanning Mutagenesis" Journal of Molecular Biology 2002 320(2):415-428.
Vermont-Desroches et al. "Meeting Abstract" Tissue Antigens 2000 5(suppl 1):52-53.
Office Communication dated Mar. 20, 2009 from U.S. Appl. No. 11/875,017, filed Oct. 19, 2007.
Office Communication dated Oct. 30, 2009 from U.S. Appl. No. 11/875,017, filed Oct. 19, 2007.
Office Communication dated May 22, 2012 from U.S. Appl. No. 12/774,966, filed May 6, 2010.
Office Communication dated Mar. 6, 2013 from U.S. Appl. No. 12/774,966, filed May 6, 2010.
Extended Search Report from EP Application 07868508.8 filed Oct. 19, 2007, Jun. 1, 2010, EP.

GAGGTGCAGCTGGTGCAGTCTGGAGCAGAGGTGAAAAAGCCCGGGGAGTCTCTGAAGATCTCCTGT
 E  V  Q  L  V  Q  S  G  A  E  V  K  K  P  G  E  S  L  K  I  S  C

AAGGGTTCTGGATACAGCTTTACCAGCTACTGGATCGGCTGGGTGCGCCAGATGCCCGGGAAAGGC
 K  G  S  G  Y  S  F  T  S  Y  W  I  G  W  V  R  Q  M  P  G  K  G
                <u>         CDR1         </u>

CTGGAGTGGATGGGGTCATCTATCCTGGTGACTCTTATACCAGATACAGCCCGTCCTTCCAAGGC
 L  E  W  M  G  V  I  Y  P  G  D  S  Y  T  R  Y  S  P  S  F  Q  G
         <u>            CDR2                        </u>

CAGGTCACCATCTCAGCCGACAAGTCCATCAGCACCGCCTACTTGCAGTGGAGCAGCCTGAAGGCC
 Q  V  T  I  S  A  D  K  S  I  S  T  A  Y  L  Q  W  S  S  L  K  A

TCGGACACCGCCATGTATTACTGTGCCAGATTCCCCAACTGGGGCTCATTTGACTACTGGGGCCAG
 S  D  T  A  M  Y  Y  C  A  R  <u>F  P  N  W  G  S  F  D  Y</u>  W  G  Q
                            <u>         CDR3              </u>

GGAACCCTGGTCACCGTCTCCTCA (SEQ ID NO:43)
 G  T  L  V  T  V  S  S    (SEQ ID NO:45)

*FIG. 1*

```
GAAATTGTGTTGACGCAGTCTCCAGGCACCCTGTCTTTGTCTCCAGGGGAAAGAGCCACCCTCTCC
 E  I  V  L  T  Q  S  P  G  T  L  S  L  S  P  G  E  R  A  T  L  S

TGCAGGGCCAGTCAGAGTATTAGCAGCAGTTACTTAGCCTGTACCAGCAGAAACCTGGCCAGGCT
 C  R  A  S  Q  S  I  S  S  S  Y  L  A  W  Y  Q  Q  K  P  G  Q  A
       ─────────────CDR1────────────

CCCAGGCTCCTCATCTATGGTGCATCCAGCAGGGCCACTGGCATCCCAGACAGGTTCAGTGGCAGT
 P  R  L  L  I  Y  G  A  S  S  R  A  T  G  I  P  D  R  F  S  G  S
             ────────CDR2────────

GGGTCTGGGACAGACTTCACTCTCACCATCAGCAGACTGGAGCCTGAAGATTTTGCAGTGTATTAC
 G  S  G  T  D  F  T  L  T  I  S  R  L  E  P  E  D  F  A  V  Y  Y

TGTCAGCAGTATGAGACGTTCGGCCAAGGGACCAAGGTGGAAATCAAA    (SEQ ID NO:47)
 C  Q  Q  Y  E  T  F  G  Q  G  T  K  V  E  I  K     (SEQ ID NO:49)
 ──────CDR3─────
```

FIG. 2

>pFab3d-10G5H
MKKTAIAIAVALAGFATVAQAALEEVQLVQSGAEVKKPGESLKISCKG
  ompA secretion signal
SG<u>YSFTSYWIG</u>WVRQMPGKGLEWMG<u>VIYPGDSYTRY</u>SPSFQGQVTISA
   CDR1                          CDR2
DKSISTAYLQWSSLKASDTAMYYCAR<u>FPNWGSFDY</u>WGQGTLVTVSS<u>AS
                              CDR3
TKGPSVFPLAPSSKSTSGGTAALGCLVKDYFPEPVTVSWNSGALTSGV
                          hCH1
HTFPAVLQSSGLYSLSSVVTVPSSSLGTQTYICNVNHKPSNTKVDKRV
                          hCH1
EPKSCDKTHTCPPCPTSG</u>HHHHHHGGEQKLISEEDLGG* <u>PFVCEYQG
                  His-tag    Myc-tag  ♦Amb
QSSDLPQPPVNAGGGSGGGSGGGSEGGGSEGGGSEGGGSEGGGSGGGS
                    pIII stump (aa198-406)
GSGDFDYEKMANANKGAMTENADENALQSDAKGKLDSVATDYGAAIDGFIGDVSGLAN
GNGATGDFAGSNSQMAQVGDGDNSPLMNNFRQYLPSLPQSVECRPYVFGAGKPYEFSI
DCDKINLFRGVFAFLLYVATFMYVFSTFANILRNKES</u> (SEQ ID NO:86)

*FIG. 4A*

>pFab3d-10G5L
MKYLLPTAAAGLLLLAAQPAMAS<u>REIVLTQSPGTLSLSPGERATLSCR
   PeI secretion signal
ASQSISSSYLA</u>WYQQKPGQAPRLLIY<u>GASSRAT</u>GIPDRFSGSGSGTDF
   CDR1                        CDR2
TLTISRLEPEDFAVYYC<u>QQYETFGQ</u>GTKVEIKRTVAAPSVFIFPPSDE
                   CDR3
<u>QLKSGTASVVCLLNNFYPREAKVQWKVDNALQSGNSQESVTEQDSKDS
                          Hck
TYSLSSTLTLSKADYEKHKVYACEVTHQGLSSPVTKSFNRGEC</u>
                                    (SEQ ID NO: 87)

*FIG. 4B*

```
                |--- CH1 STARTS HERE
IgG1    LVTVSSASTK GPSVFPLAPS SKSTSGGTAA LGCLVKDYFP EPVTVSWNSG
IgG2    LVTVSSASTK GPSVFPLAPC SRSTSESTAA LGCLVKDYFP EPVTVSWNSG
IgG4    LVTVSSASTK GPSVFPLAPC SRSTSESTAA LGCLVKDYFP EPVTVSWNSG
IgG2M4  LVTVSSASTK GPSVFPLAPC SRSTSESTAA LGCLVKDYFP EPVTVSWNSG
        (VH-C1 LINKER)
                                              C200
IgG1    ALTSGVHTFP AVLQSSGLYS LSSVVTVPSS SLGTQTYICN VNHKPSNTKV
IgG2    ALTSGVHTFP AVLQSSGLYS LSSVVTVTSS NFGTQTYTCN VDHKPSNTKV
IgG4    ALTSGVHTFP AVLQSSGLYS LSSVVTVPSS SLGTKTYTCN VDHKPSNTKV
IgG2M4  ALTSGVHTFP AVLQSSGLYS LSSVVTVTSS NFGTQTYTCN VDHKPSNTKV

-HINGE REGION--||----CH2-> P238          M252      C261
IgG1    DKKAEPKSCD KTHTCPPCPA PELLGGPSVF LFPPKPKDTL MISRTPEVTC
IgG2    DKTVERKCC- --VECPPCPA PP-VAGPSVF LFPPKPKDTL MISRTPEVTC
IgG4    DKRVESKYGP ---PCPSCPA PEFLGGPSVF LFPPKPKDTL MISRTPEVTC
IgG2M4  DKTVERKCC- --VECPPCPA PP-VAGPSVF LFPPKPKDTL MISRTPEVTC
                       (LOWER HINGE)                FcRn-BIND

D265 D270                        N297*      T307
IgG1    VVVDVSHEDP EVKFNWYVDG VEVHNAKTKP REEQYNSTYR VVSVLTVLHQ
IgG2    VVVDVSHEDP EVQFNWYVDG VEVHNAKTKP REEQFNSTFR VVSVLTVVHQ
IgG4    VVVDVSQEDP EVQFNWYVDG VEVHNAKTKP REEQFNSTYR VVSVLTVLHQ
IgG2M4  VVVDVSQEDP EVQFNWYVDG VEVHNAKTKP REEQFNSTFR VVSVLTVLHQ
          B/C LOOP                         C'E LOOP   FcRn-BIND

C321       P329       |----CH3->
IgG1    DWLNGKEYKC KVSNKALPAPI EKTISKAKG QPREPQVYTL PPSRDELTKN
IgG2    DWLNGKEYKC KVSNKGLPAPI EKTISKTKG QPREPQVYTL PPSREEMTKN
IgG4    DWLNGKEYKC KVSNKGLPSSI EKTISKAKG QPREPQVYTL PPSQEEMTKN
IgG2M4  DWLNGKEYKC KVSNKGLPSSI EKTISKTKG QPREPQVYTL PPSREEMTKN
                  F/G LOOP

IgG1    QVSLTCLVKG FYPSDIAVEW ESNGQPENNY KTTPPVLDSD GSFFLYSKLT
IgG2    QVSLTCLVKG FYPSDIAVEW ESNGQPENNY KTTPPMLDSD GSFFLYSKLT
IgG4    QVSLTCLVKG FYPSDIAVEW ESNGQPENNY KTTPPVLDSD GSFFLYSRLT
IgG2M4  QVSLTCLVKG FYPSDIAVEW ESNGQPENNY KTTPPMLDSD GSFFLYSKLT

H433
IgG1    VDKSRWQQGN VFSCSVMHEA LHNHYTQKSL SLSPGK* (SEQ ID NO:97)
IgG2    VDKSRWQQGN VFSCSVMHEA LHNHYTQKSL SLSPGK* (SEQ ID NO:98)
IgG4    VDKSRWQEGN VFSCSVMHEA LHNHYTQKSL SLSLGK* (SEQ ID NO:99)
IgG2M4  VDKSRWQQGN VFSCSVMHEA LHNHYTQKSL SLSPGK* (SEQ ID NO:100)
                              FcRn-BIND
```

FIG. 16

HIGH AFFINITY ANTIBODY ANTAGONISTS OF INTERLEUKIN-13 RECEPTOR ALPHA 1

INTRODUCTION

This application is a continuation of U.S. Ser. No. 12/774,966 filed May 6, 2010, which is a continuation of U.S. Ser. No. 11/875,017 filed Oct. 19, 2007, now issued as U.S. Pat. No. 7,754,213, which claims benefit of priority to U.S. Provisional Patent Application Ser. No. 60/852,884, filed Oct. 19, 2006, each of which are herein incorporated by reference in their entireties.

BACKGROUND OF THE INVENTION

Data from human studies and experimental animal models strongly implicate Th2-derived cytokines as contributing to atopic asthma, with interleukin-4 (IL-4) and interleukin-13 (IL-13; see, e.g., Minty et al., 1993 *Nature* 362:248-250; McKenzie et al., 1993 *Proc. Natl. Acad. Sci. USA* 90:3735-3739; Acc. Nos: U31120 and L13029 (human) and NM_001032929 (*Macaca mulatta*)) playing the most central role. These two cytokines have significant structural similarities and share certain receptor components. The receptor that IL-4 and IL-13 share is a dual IL-4R/IL-13 receptor (or type II receptor) which binds both IL-4 and IL-13. This receptor is composed of the IL-4Rα chain (see, e.g., Idzerda et al., 1990 *J. Exp. Med.* 171:861-873) and the IL-13Rα1 chain (see, e.g., Hilton et al., 1996 *Proc. Natl. Acad. Sci. USA* 93:497-501; Aman et al., 1996 *J. Biol. Chem.* 271:29265-29270; Miloux et al., 1997 *FEBS Lett.* 401:163-166; Acc. Nos: U62858 and CAA70508 (human) and AAP78901 (*Macaca fascicularis*)). The dual IL-4R/IL-13R receptor is expressed on hematopoietic and non-hematopoietic cells, including lung epithelial and smooth muscle cells. Both IL-4 and IL-13, additionally, each have one receptor that recognizes them to the exclusion of the other. For instance, IL-4 receptor (IL-4R) type I, composed of the IL-4Rα chain and the common gamma chain (γc), specifically binds IL-4. IL-4R type I is expressed exclusively on cells of hematopoietic origin. The receptor specific for IL-13, IL-13Rα2, binds IL-13 with high affinity, but apparently does not transduce signals. Rather, the receptor acts as a decoy to attenuate the response to IL-13.

IL-13 and IL-4 carry out a number of functions and both regulate a number of functions related to the allergic phenotype, such as isotype class switching to IgE in B-cells, activation of mast cells and eosinophils, up-regulation of vascular cell adhesion molecule-1 (VCAM-1) on endothelial cells, and production of chemokines such as eotaxins, thymus and activation-regulated chemokine (TARC), and macrophage-derived chemokine (MDC).

IL-4 and IL-13, though, have many distinct functions in vitro and in vivo owing to differences in their receptor complexes. For instance, sequestration of IL-13, but not IL-4, has been shown to prevent airway hyperreactivity and reduce mucous production in mouse asthma models. This correlation between IL-13 and the asthmatic response has been further supported by other studies; see, e.g., Hershey et al., 2003 *J. Allergy Clin. Immunol.* 111(4):677-690; Grunig et al., 1998 *Science* 282(5397):2261-2263; Mattes et al., 2001 *J. Immunol.* 167(3):1683-1692; and Fulkerson et al., 2006 *Am. J. Respir. Cell. Mol. Biol.* 35(3)337-346. Delivery of IL-13 to the lung, for example, has been found to be sufficient to induce the entire asthma-like phenotype in mice. Treated animals develop airway hyperreactivity, eosinophil-rich cell inflammation, goblet cell hyperplasia with associated mucous overproduction, and subepithelial fibrosis; see, e.g., Wills-Karp et al., 1998 *Science* 282(5397): 2258-2261; Reiman et al., 2006 *Infect. Immun.* 74(3): 1471-1479; and Kaviratne et al., 2004 *J. Immunol.* 173(6):4020-4029. Expression of IL-13 has, furthermore, been reported to be elevated in the lungs of human asthmatics. In addition, several groups have reported associations of polymorphisms in the IL-13 gene with an increased risk of allergic traits and asthma symptoms. Some of these polymorphisms have been shown to be correlated with increased expression of IL-13; see, e.g., Huang et al., 1995 *J. Immunol.* 155(5)2688-2694; Naseer et al., 1997 *Am. J. Respir. Crit. Care Med.* 155(3):845-851; Vladich et al., 2005 *J. Clin. Invest.* 115(3):747-754; Chen et al., 2004 *J. Allergy Clin. Immunol.* 114(3):553-560; and Vercelli et al., 2002 *Curr. Opin. Allergy Clin. Immunol.* 2(5):389-393.

IL-13 has also been associated with various other conditions, including but not limited to various respiratory and allergy-mediated disorders, fibrosis, scleroderma, inflammatory bowel disease and certain cancers; see, e.g., Wynn, T. A., 2003 *Annu. Rev. Immunol.* 21:425-456; Terabe et al., 2000 *Nat. Immunol.* 1(6):515-520; Fuss et al., 2004 *J. Clin. Invest.* 113(10):1490-1497; Simms et al., 2002 *Curr. Opin. Rheumatol.* 14(6):717-722; and Hasegawa et al., 1997 *J. Rheumatol.* 24(2):328-332.

An antagonist of IL-13 would, therefore, be a highly attractive molecule for use in the development of a treatment for IL-13-associated disorders. An effective antibody antagonist would interfere with the binding of IL-13 to IL-13R. An effective antibody antagonist to IL-13Rα1 may also interfere with the binding of IL-13 and prevent heterodimerization of IL-4Rα and IL-13Rα1. Such an antibody could inhibit signaling of both IL-13 and IL-4 through the type II receptor while sparing IL-4 signaling through the type I receptor. Signaling through the type I receptor is essential in the induction phase of the immune response during which Th2 cells differentiate. T cells do not express IL-13Rα1 so the type II receptor plays no role in Th2 differentiation. Hence, an IL-13Rα1 antibody should not affect the overall Th1/Th2 balance. Signaling through the type II IL-4/IL-13 receptor is critical during the effector stage of the immune response during established allergic inflammation. Thus, blockade of the type II receptor should have a beneficial effect on many of the symptoms of asthma and other IL-13R-mediated conditions and should, therefore, be an effective disease modifying agent.

Antibodies against IL-13Rα1 (both monoclonal and polyclonal) have been described in the art; see, e.g., WO 97/15663, WO 03/80675; WO 03/46009; WO 06/072564; Gauchat et al., 1998 *Eur. J. Immunol.* 28:4286-4298; Gauchat et al., 2000 *Eur. J. Immunol.* 30:3157-3164; Clement et al., 1997 *Cytokine* 9(11):959 (Meeting Abstract); Ogata et al., 1998 *J. Biol. Chem.* 273:9864-9871; Graber et al., 1998 *Eur. J. Immunol.* 28:4286-4298; C. Vermot-Desroches et al., 2000 *Tissue Antigens* 5(Supp. 1):52-53 (Meeting Abstract); Poudrier et al., 2000 *Eur. J. Immunol.* 30:3157-3164; Akaiwa et al., 2001 *Cytokine* 13:75-84; Cancino-Díaz et al., 2002 *J. Invest. Dermatol.* 119:1114-1120; and Krause et al., 2006 *Mol. Immunol.* 43:1799-1807.

There is a need for an antibody with enhanced biological activity that could impact activities associated with the allergy and asthmatic response as well as other various conditions that have been attributed at least in part to an increased expression/functioning of IL-13Rα1. There is further a need for an antibody molecule with high affinity for IL-13Rα1 with low immunogenicity in humans. Accordingly, it would be of great import to produce a therapeutic-based human antibody antagonist of IL-13Rα1 that inhibits or antagonizes the activity of IL-13Rα1 and the corresponding role IL-13Rα1 plays in various therapeutic conditions.

SUMMARY OF THE INVENTION

The present invention relates to high affinity antibody antagonists of IL-13Rα1 and particularly human IL-13Rα1. Disclosed antibody molecules selectively recognize IL-13Rα1, particularly human IL-13Rα1, exhibiting binding to human IL-13Rα1 with a $K_D$ of $5 \times 10^{-9}$ or less, more preferably $2 \times 10^{-9}$ or less, and even more preferably, $1 \times 10^{-9}$ or less. Specific antibody molecules in accordance herewith additionally, bind primate IL-13Rα1 with high affinity, a desirable quality given the accessibility of non-human primate models for predicting efficacy and safety profiles in humans. Antibody molecules in accordance herewith are effective in the inhibition of IL-13Rα1-mediated activities and, thus, are of import in the treatment of conditions associated therewith, including, but not limited to, asthma, allergy, allergic rhinitis, chronic sinusitis, hay fever, atopic dermatitis, chronic obstructive pulmonary disease ("COPD"), pulmonary fibrosis, esophageal eosinophilia, scleroderma, psoriasis, psoriatic arthritis, fibrosis, inflammatory bowel disease (particularly, ulcerative colitis), anaphylaxis, and cancer (particularly, Hodgkin's lymphoma, glioma, and renal carcinoma), and general Th2-mediated disorders/conditions. IL-13Rα1-specific antibodies also have utility for various diagnostic purposes in the detection and quantification of IL-13Rα1.

The present invention provides, in one particular aspect, the isolated antibody, 10G5, which very effectively antagonizes IL-13 functioning through IL-13Rα1. 10G5 exhibits inhibition of IL-13- and IL-4-induced eotaxin release in NHDF cells, IL-13- and IL-4-induced STAT6 phosphorylation in NHDF cells, and IL-13-stimulated release of TARC in blood or peripheral blood mononuclear cells (PBMCs). The present invention, thus, encompasses antibodies as produced by the hybridoma cell line deposited as ATCC Deposit No. PTA-6933. The present invention also encompasses antibodies that compete for binding to hIL-13Rα1 with an antibody of PTA-6933. Particular embodiments of the present invention include antibody molecules including heavy and/or light chain variable region sequences of 10G5, as well as equivalents (characterized as having one or more conservative amino acid substitutions) or homologs thereof. Particular embodiments embrace isolated antibody molecules that have the CDR domains disclosed herein or sets of heavy and/or light chain CDR domains disclosed herein, or equivalents thereof, characterized as having one or more conservative amino acid substitutions. Specifically, antibody molecules of the invention have a heavy chain variable region with CDR1, CDR2, and CDR3 amino acid sequences as set forth in SEQ ID NO:82, SEQ ID NO:83, and SEQ ID NO:121, respectively; and a light chain variable region with CDR1, CDR2, and CDR3 amino acid sequences as set forth in SEQ ID NO:84, SEQ ID NO:85, and SEQ ID NO:122. More particularly, antibody molecules of the invention have a heavy chain variable region with an amino acid sequence as set forth in SEQ ID NO:45, SEQ ID NO:51, SEQ ID NO: 55, SEQ ID NO:59, SEQ ID NO:63 or SEQ ID NO:67; a light chain variable region with an amino acids sequence as set forth in SEQ ID NO:49, SEQ ID NO:71, SEQ ID NO:75 or SEQ ID NO:79; or a combination of the above-referenced heavy chain and light chain variable regions.

As will be appreciated by those skilled in the art, fragments of an antibody that retain the ability to bind to hIL-13Rα1 may be inserted into various frameworks, see, e.g., U.S. Pat. No. 6,818,418, and references contained therein, which discuss various scaffolds which may be used to display antibody loops previously selected on the basis of antigen binding. In addition, genes encoding for $V_L$ and $V_H$ can be joined, using recombinant methods, for example using a synthetic linker that enables them to be made as a single protein chain in which the $V_L$ and $V_H$ regions pair to form monovalent molecules, otherwise known as single chain Fvs (ScFVs); see, e.g., Bird et al., 1988 *Science* 242: 423-426, and Huston et al., 1988 *Proc. Natl. Acad. Sci. USA* 85:5879-5883.

In another aspect, the present invention provides nucleic acid encoding the disclosed antibody molecules. The present invention also provides nucleic acids encoding the variable heavy and light chains and select components thereof, particularly the disclosed respective CDR3 regions. In another aspect, the present invention provides vectors including said nucleic acid. In another aspect, the present invention provides isolated cell(s) harboring nucleic acid encoding the disclosed antibody molecules and components thereof as described. In another aspect, the present invention provides isolated cell(s) comprising a polypeptide or vector of the present invention.

In another aspect, the present invention provides a method of making an antibody molecule which selectively binds IL-13Rα1 (inclusive of antibodies, antigen binding fragments, derivatives, chimeric molecules, fusions of any of the foregoing with another polypeptide, or alternative structures/compositions incorporating any of the foregoing) of the present invention, which includes incubating a cell harboring nucleic acid encoding a heavy and/or a light chain (depending on the antibody molecule being produced) under conditions that allow for the expression and/or assembly of said heavy and/or light chains into the antibody molecule, and isolating said antibody molecule from the cell. One of skill in the art can obtain the antibody molecules disclosed herein using standard recombinant DNA techniques.

In another aspect, the present invention provides a method for antagonizing the activity or function of IL-13Rα1, be it signaling or other, which includes contacting a cell expressing IL-13Rα1 with an antibody molecule disclosed herein under conditions that allow said antibody molecule to bind to IL-13Rα1. Specific embodiments of the present invention include such methods wherein the cell is a human cell. Antibody molecules in accordance herewith are effective in the inhibition of IL-13Rα1-mediated activities. Antibody molecules in accordance with the present invention were found to effectively inhibit eotaxin release from normal human dermal fibroblast cells (hereinafter "NHDF" cells). Antibody molecules in accordance with the present invention were found to effectively inhibit IL-13- and IL-4-stimulated STAT6 phosphorylation in NHDF cells and found to effectively inhibit the IL-13-stimulated release of TARC(CCL17) in whole blood (human/rhesus).

In another aspect, the present invention provides a method of antagonizing the activity of IL-13Rα1 in a subject exhibiting a condition associated with IL-13Rα1 activity (or a condition where the functioning of IL-13Rα1 is deemed not beneficial to the particular subject), which involves administering to the subject a therapeutically effective amount of an antibody molecule of the present invention. In select embodiments, the condition may be asthma, allergy, allergic rhinitis, chronic sinusitis, hay fever, atopic dermatitis, chronic obstructive pulmonary disease ("COPD"), pulmonary fibrosis, esophageal eosinophilia, psoriasis, psoriatic arthritis, fibrosis, scleroderma, inflammatory bowel disease (particularly, ulcerative colitis), anaphylaxis, and cancer (particularly, Hodgkin's lymphoma, glioma, and renal carcinoma), and general Th2-mediated disorders/conditions. In another aspect, the present invention provides a pharmaceutical composition or other composition including an antibody molecule of the invention (or alternative antigen-binding structure or protein that comprises an IL-13Rα1-specific antigen binding portion disclosed herein) and a pharmaceutically acceptable carrier, excipient, diluent, stabilizer, buffer, or alternative designed to facilitate administration of the antibody molecule in the desired amount to the treated individual.

Another aspect of the present invention concerns the identification of a critical contact point between the antibodies disclosed herein and hIL-13Rα1. This critical contact point was identified by the generation of a specific mutation that impacted the binding of the receptor by the antibody. More specifically, it was found that substitution of the phenylalanine residue at position 233 of SEQ ID NO:101 with an alanine residue results in a loss of binding between the antibody and the receptor. This is a very useful finding in characterizing 10G5 and its derivatives. Peptides exploiting the narrow region surrounding amino acid 233 will be useful in the generation of additional monoclonal antibodies with similar specificity. Accordingly, the present invention encompasses isolated peptides including hIL-13R sequence with a Phe233Ala mutation, whether they be full-length or fragments thereof including the mutation. Additionally, the present invention also encompasses the use of said peptides in an assay to evaluate 10G5 or 10G5 derivatives, identify antibodies with specificity for a similar epitope or, alternatively, produce antibodies with similar specificity.

BRIEF DESCRIPTION OF THE DRAWINGS

FIG. 1 illustrates the nucleotide and derived amino acid sequence of the heavy chain variable region of antibody 10G5. CDRs and nucleic acid encoding CDRs are underlined.

FIG. 2 illustrates the nucleotide and derived amino acid sequence of the light chain variable region of antibody 10G5. CDRs and nucleic acid encoding CDRs are underlined.

FIGS. 4A and 4B illustrate heavy and light chain constructs, SEQ ID NOs:86 AND 87, respectively, of 10G5 Fab in pFab3d.

FIG. 16 illustrates a sequence comparison of the Fc domains of IgG1 (SEQ ID NO:97), IgG2 (SEQ ID NO:98), IgG4 (SEQ ID NO:99) and the IgG2 m4 (SEQ ID NO:100) isotypes.

DETAILED DESCRIPTION OF THE INVENTION

Figure 3:
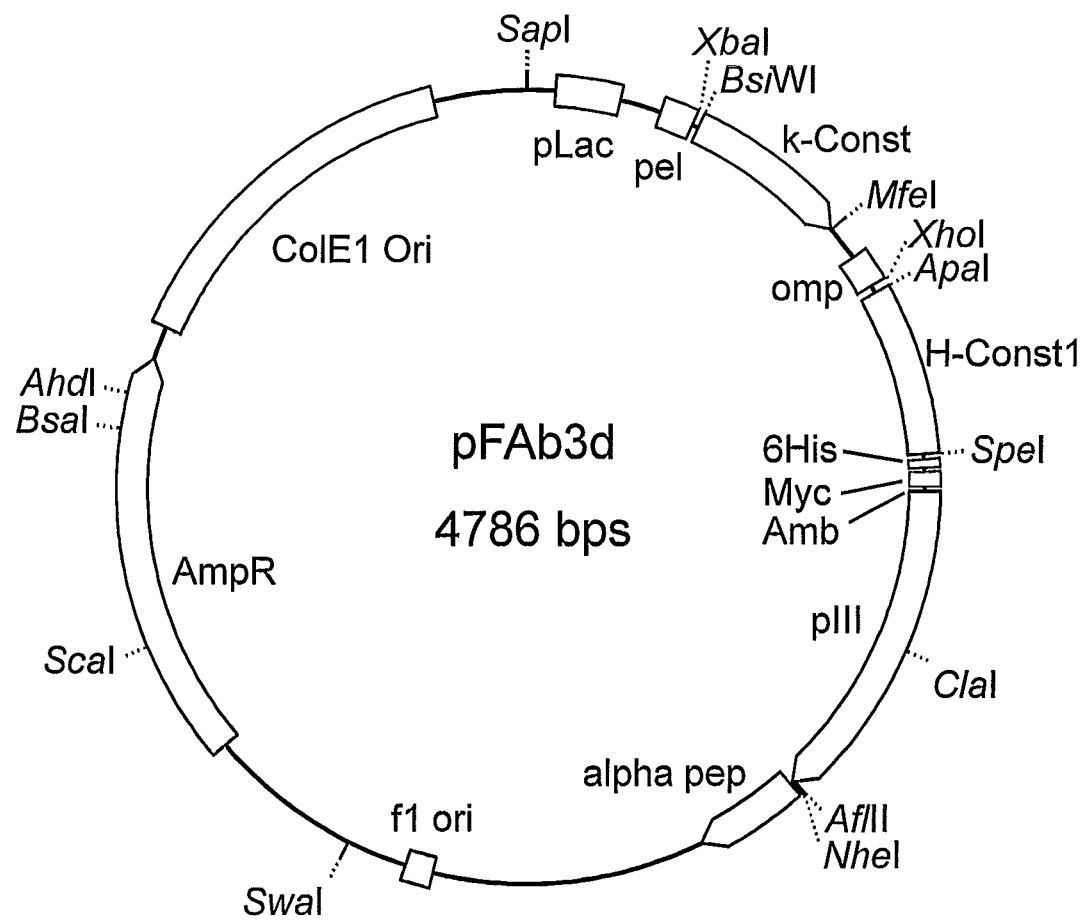
FIG. 3 illustrates a genetic map of pFab3d.

The present invention relates to high affinity antibody antagonists of IL-13Rα1 and particularly human IL-13Rα1. Disclosed antibody molecules selectively recognize and specifically bind to IL-13Rα1. In particular embodiments, the antibodies bind primate IL-13Rα1 (e.g., cynomolgus IL-13Rα1) with high affinity, a desirable quality given the accessibility of non-human primate models for predicting efficacy and safety profiles in humans. Use of the terms "selective" or "specific" herein refers to the fact that the disclosed antibody molecules do not show significant binding to other than IL-13Rα1. The disclosed antibody molecules bind to human IL-13Rα1 with a $K_D$ of $5\times10^{-9}$ or less, more preferably $2\times10^{-9}$ or less, and even more preferably, $1\times10^{-9}$ or less. $K_D$ refers to the dissociation constant obtained from the ratio of $K_d$ (the dissociation rate of a particular antibody-antigen interaction) to $K_a$ (the association rate of the particular antibody-antigen interaction), or $K_d/K_a$ which is expressed as a molar concentration (M). $K_D$ values can be determined using methods well established in the art. A preferred method for determining the $K_D$ of an antibody is by using surface plasmon resonance, for example a biosensor system such as a BIACORE™ (Pharmacia AB Corporation) system.

Antibodies, as described herein, are particularly effective in antagonizing IL-13Rα1 function, or IL-13Rα1-mediated activity as referred to herein. The language "IL-13Rα1-mediated" activity/function is used herein to refer to any activity/function that requires, or is exacerbated or enhanced by, the function of IL-13Rα1. The disclosed antibody molecules have been shown to exhibit at least one of the following functional properties: (i) inhibition of IL-13-induced eotaxin release in NHDF cells; (ii) inhibition of IL-4-induced eotaxin release in NHDF cells; (iii) inhibition of IL-13-induced STAT6 phosphorylation in NHDF cells; (iv) inhibition of IL-4-induced STAT6 phosphorylation in NHDF cells; or (v) inhibition of IL-13-stimulated release of TARO in blood or PBMCs. Specific embodiments of the present invention provide antibody molecules that antagonize IL-13Rα1-mediated eotaxin release from NHDF cells with an $IC_{50}$ of 1.0 μg/ml or less, more preferably, 0.5 μg/ml or less, and more preferably yet, 0.1 μg/ml or less. Specific embodiments of the present invention provide antibody molecules that antagonize IL-13Rα1-mediated STAT6 phosphorylation in NHDF cells. Specific embodiments of the present invention provide antibody molecules that antagonize IL-13Rα1-mediated TARO (CCL17) release in whole blood or PBMCs with an $IC_{50}$ of 1000 ng/ml or less, more preferably, 500 ng/ml or less, and more preferably yet, 250 ng/ml or less. The extent of antagonism by any particular antibody can be measured quantitatively as the $IC_{50}$ value in statistical comparison to a control, or via any alternative method available in the art for assessing a negative effect on, or inhibition of, IL-13Rα1 function (i.e., any method capable of assessing antagonism of IL-13Rα1 function).

"Antibody molecule" or "antibody", as described herein, refers to an immunoglobulin-derived structure with selective binding to hIL-13Rα1 including, but not limited to, a full length or whole antibody, an antigen binding fragment (a fragment derived, physically or conceptually, from an antibody structure), a derivative of any of the foregoing, a chimeric molecule, a fusion of any of the foregoing with another polypeptide, or any alternative structure/composition which incorporates any of the foregoing for purposes of selectively binding/inhibiting the function of IL-13Rα1. "Whole" antibodies or "full-length" antibodies refer to proteins that have two heavy (H) and two light (L) chains inter-connected by disulfide bonds which include: (1) in terms of the heavy chains, a variable region (abbreviated herein as "$V_H$") and a heavy chain constant region which has three domains, $C_{H1}$, $C_{H2}$, and $C_{H3}$; and (2) in terms of the light chains, a light chain variable region (abbreviated herein as "$V_L$") and a light chain constant region which includes one domain, $C_L$. "Isolated", as used herein, describes a property as it pertains to the disclosed antibody molecules, nucleic acid or other that makes them different from that found in nature. The difference can be, for example, that they are of a different purity than that found in nature, or that they are of a different structure or form than that found in nature. A structure not found in nature, for example, includes recombinant human immunoglobulin structures including, but not limited to, recombinant human immunoglobulin structures with optimized complementarity determining regions (CDRs). Other examples of structures not found in nature are antibody molecules or nucleic acid substantially free of other cellular material. Isolated antibodies are generally free of other antibodies having different antigenic specificities (other than IL-13Rα1).

Antibody fragments and, more specifically, antigen binding fragments are molecules possessing an antibody variable region or segment thereof (which includes one or more of the disclosed CDR 3 domains, heavy and/or light), which confers selective binding to IL-13Rα1, and particularly human IL-13Rα1 (hIL-13Rα1). Antibody fragments containing such an antibody variable region include, but are not limited to the following antibody molecules: a Fab, a F(ab')$_2$, a Fd, a Fv, a scFv, bispecific antibody molecules (i.e., antibody molecules including an IL-13R+1-specific antibody or antigen binding fragment as disclosed herein linked to a second functional moiety having a different binding specificity than the antibody, including, without limitation, another peptide or protein such as an antibody, or receptor ligand), a bispecific single chain Fv dimer, an isolated CDR3, a minibody, a 'scAb', a dAb fragment, a diabody, a triabody, a tetrabody, and artificial antibodies based upon protein scaffolds, including but not limited to fibronectin type III polypeptide antibodies (see, e.g., U.S. Pat. No. 6,703,199, WO 02/32925 and WO 00/34784) or cytochrome B (see, e.g., Nygren et al., 1997 Curr. Opinion Struct. Biol. 7:463-469). The antibody portions or binding fragments may be natural, or partly or wholly synthetically produced. Such antibody portions can be prepared by various means known by one of skill in the art, including, but not limited to, conventional techniques, such as papain or pepsin digestion.

The present invention provides, in one particular aspect, isolated antibody 10G5 which very effectively antagonizes IL-13 functioning through IL-13Rα1. 10G5 has exhibited inhibition of IL-13- and IL-4-induced eotaxin release in NHDF cells, IL-13- and IL-4-induced STAT6 phosphorylation in NHDF cells, and IL-13-stimulated release of TARC in blood or peripheral blood mononuclear cells (PBMCs). The present invention, thus, encompasses antibodies as produced by the hybridoma cell line deposited as ATCC Deposit No. PTA-6933. The present invention also encompasses antibody molecules that compete for binding to hIL-13Rα1 with an antibody of PTA-6933. Additional embodiments of the present invention are antibody molecules that compete for binding to hIL-13Rα1 with antibodies disclosed herein. Specific embodiments of the present invention provide isolated antibody molecules which inhibit the binding of IL-13 to hIL-13Rα1.

Particular embodiments of the present invention include antibody molecules having heavy and/or light chain variable region sequences of 10G5, as well as equivalents (characterized as having one or more conservative amino acid substitutions) or homologs thereof. Particular embodiments are isolated antibody molecules that include the CDR domains disclosed herein or sets of heavy and/or light chain CDR domains disclosed herein, or equivalents thereof, characterized as having one or more conservative amino acid substitutions. Use of the terms "domain" or "region" herein simply refers to the respective portion of the antibody molecule wherein the sequence or segment at issue will reside or, in the alternative, currently resides.

Table 1 provides a generalized outline of sequences embraced by the present invention.

TABLE 1

| SEQ ID NO: | DESCRIPTION |
|---|---|
| SEQ ID NO: 1 | HEAVY CHAIN CDR3 OPTIMIZED VARIANT |
| SEQ ID NO: 2 | HEAVY CHAIN CDR3 OPTIMIZED VARIANT |
| SEQ ID NO: 3 | HEAVY CHAIN CDR3 OPTIMIZED VARIANT |
| SEQ ID NO: 4 | HEAVY CHAIN CDR3 OPTIMIZED VARIANT |
| SEQ ID NO: 5 | HEAVY CHAIN CDR3 OPTIMIZED VARIANT |
| SEQ ID NO: 6 | HEAVY CHAIN CDR3 OPTIMIZED VARIANT |
| SEQ ID NO: 7 | HEAVY CHAIN CDR3 OPTIMIZED VARIANT |
| SEQ ID NO: 8 | HEAVY CHAIN CDR3 OPTIMIZED VARIANT |
| SEQ ID NO: 9 | HEAVY CHAIN CDR3 OPTIMIZED VARIANT |
| SEQ ID NO: 10 | HEAVY CHAIN CDR3 OPTIMIZED VARIANT |
| SEQ ID NO: 11 | HEAVY CHAIN CDR3 OPTIMIZED VARIANT |
| SEQ ID NO: 12 | HEAVY CHAIN CDR3 OPTIMIZED VARIANT |
| SEQ ID NO: 13 | HEAVY CHAIN CDR3 OPTIMIZED VARIANT |
| SEQ ID NO: 14 | HEAVY CHAIN CDR3 OPTIMIZED VARIANT |
| SEQ ID NO: 15 | HEAVY CHAIN CDR3 OPTIMIZED VARIANT |
| SEQ ID NO: 16 | HEAVY CHAIN CDR3 OPTIMIZED VARIANT |
| SEQ ID NO: 17 | HEAVY CHAIN CDR3 OPTIMIZED VARIANT |
| SEQ ID NO: 18 | HEAVY CHAIN CDR3 OPTIMIZED VARIANT |
| SEQ ID NO: 19 | VARIANT SEQUENCE W/ OPTIMIZED CDR3 |
| SEQ ID NO: 20 | VARIANT SEQUENCE W/ OPTIMIZED CDR3 |
| SEQ ID NO: 21 | VARIANT SEQUENCE W/ OPTIMIZED CDR3 |
| SEQ ID NO: 22 | VARIANT SEQUENCE W/ OPTIMIZED CDR3 |
| SEQ ID NO: 23 | VARIANT SEQUENCE W/ OPTIMIZED CDR3 |
| SEQ ID NO: 24 | VARIANT SEQUENCE W/ OPTIMIZED CDR3 |
| SEQ ID NO: 25 | VARIANT SEQUENCE W/ OPTIMIZED CDR3 |
| SEQ ID NO: 26 | HEAVY CHAIN CDR3 OPTIMIZED VARIANT |
| SEQ ID NO: 27 | LIGHT CHAIN CDR3 OPTIMIZED VARIANT |
| SEQ ID NO: 28 | LIGHT CHAIN CDR3 OPTIMIZED VARIANT |
| SEQ ID NO: 29 | LIGHT CHAIN CDR3 OPTIMIZED VARIANT |
| SEQ ID NO: 30 | LIGHT CHAIN CDR3 OPTIMIZED VARIANT |
| SEQ ID NO: 31 | LIGHT CHAIN CDR3 OPTIMIZED VARIANT |
| SEQ ID NO: 32 | LIGHT CHAIN CDR3 OPTIMIZED VARIANT |
| SEQ ID NO: 33 | LIGHT CHAIN CDR3 OPTIMIZED VARIANT |
| SEQ ID NO: 34 | LIGHT CHAIN CDR3 OPTIMIZED VARIANT |
| SEQ ID NO: 35 | LIGHT CHAIN CDR3 OPTIMIZED VARIANT |
| SEQ ID NO: 36 | LIGHT CHAIN CDR3 OPTIMIZED VARIANT |
| SEQ ID NO: 37 | LIGHT CHAIN CDR3 OPTIMIZED VARIANT |
| SEQ ID NO: 38 | LIGHT CHAIN CDR3 OPTIMIZED VARIANT |
| SEQ ID NO: 39 | LIGHT CHAIN CDR3 OPTIMIZED VARIANT |
| SEQ ID NO: 40 | 10G5 HEAVY CHAIN CDR3 |
| SEQ ID NO: 41 | 10G5 LIGHT CHAIN CDR3 |
| SEQ ID NO: 42 | 10G5 VH SEQ W/ LEADER, & ADDITIONAL CONSTANT REGION - NUCLEIC ACID |
| SEQ ID NO: 43 | 10G5 VH SEQUENCE ONLY - NUCLEIC ACID |
| SEQ ID NO: 44 | 10G5 VH SEQ W/ LEADER, & ADDITIONAL CONSTANT REGION - PROTEIN |
| SEQ ID NO: 45 | 10G5 VH SEQUENCE ONLY - PROTEIN |
| SEQ ID NO: 46 | 10G5 VL SEQ W/ LEADER & ADDITIONAL CONSTANT REGION - NUCLEIC ACID |
| SEQ ID NO: 47 | 10G5 VL SEQUENCE ONLY - NUCLEIC ACID |
| SEQ ID NO: 48 | 10G5 VL SEQ W/ LEADER & ADDITIONAL CONSTANT REGION - PROTEIN |

TABLE 1-continued

| SEQ ID NO: | DESCRIPTION |
|---|---|
| SEQ ID NO: 49 | 10G5 VL SEQUENCE ONLY - PROTEIN |
| SEQ ID NO: 50 | 10G5-1,3 HEAVY CHAIN* |
| SEQ ID NO: 51 | 10G5-1,3 VH* |
| SEQ ID NO: 52 | 10G5-1,3 HEAVY CHAIN NUCLEIC ACID* |
| SEQ ID NO: 53 | 10G5-1,3 VH NUCLEIC ACID* |
| SEQ ID NO: 54 | 10G5-2 HEAVY CHAIN |
| SEQ ID NO: 55 | 10G5-2 VH |
| SEQ ID NO: 56 | 10G5-2 HEAVY CHAIN NUCLEIC ACID |
| SEQ ID NO: 57 | 10G5-2 VH NUCLEIC ACID |
| SEQ ID NO: 58 | 10G5-4,5 HEAVY CHAIN* |
| SEQ ID NO: 59 | 10G5-4,5 VH* |
| SEQ ID NO: 60 | 10G5-4,5 HEAVY CHAIN NUCLEIC ACID* |
| SEQ ID NO: 61 | 10G5-4,5 VH NUCLEIC ACID* |
| SEQ ID NO: 62 | 10G5-6, HEAVY CHAIN* |
| SEQ ID NO: 63 | 10G5-6, VH* |
| SEQ ID NO: 64 | 10G5-6, HEAVY CHAIN NUCLEIC ACID* |
| SEQ ID NO: 65 | 10G5-6, VH NUCLEIC ACID* |
| SEQ ID NO: 66 | 10G5-7, 8 HEAVY CHAIN |
| SEQ ID NO: 67 | 10G5-7, 8 VH |
| SEQ ID NO: 68 | 10G5-7, 8 HEAVY CHAIN NUCLEIC ACID |
| SEQ ID NO: 69 | 10G5-7, 8 VH NUCLEIC ACID |
| SEQ ID NO: 70 | 10G5-1,2,4,6,7 LIGHT CHAIN* |
| SEQ ID NO: 71 | 10G5-1,2,4,6,7 VL* |
| SEQ ID NO: 72 | 10G5-1,2,4,6,7 LIGHT CHAIN NUCLEIC ACID* |
| SEQ ID NO: 73 | 10G5-1,2,4,6,7 VL NUCLEIC ACID* |
| SEQ ID NO: 74 | 10G5-3 LIGHT CHAIN |
| SEQ ID NO: 75 | 10G5-3 VL |
| SEQ ID NO: 76 | 10G5-3 LIGHT CHAIN NUCLEIC ACID |
| SEQ ID NO: 77 | 10G5-3 VL NUCLEIC ACID |
| SEQ ID NO: 78 | 10G5-5,8 LIGHT CHAIN* |
| SEQ ID NO: 79 | 10G5-5,8 VL* |
| SEQ ID NO: 80 | 10G5-5,8 LIGHT CHAIN NUCLEIC ACID* |
| SEQ ID NO: 81 | 10G5-5,8 VL NUCLEIC ACID* |
| SEQ ID NO: 82 | 10G5 VH CDR1 |
| SEQ ID NO: 83 | 10G5 VH CDR2 |
| SEQ ID NO: 84 | 10G5 VL CDR1 |
| SEQ ID NO: 85 | 10G5 VL CDR2 |
| SEQ ID NO: 86 | PFAB3D-10G5H |
| SEQ ID NO: 87 | PFAB3D-10G5L |
| SEQ ID NO: 92 | CONSTANT OF IGG2M4 |
| SEQ ID NO: 93 | CONSTANT OF IGG2M4 NUCLEIC ACID |
| SEQ ID NO: 94 | 10G5-6 HEAVY CHAIN IGG2M4 |
| SEQ ID NO: 95 | 10G5-6 HEAVY CHAIN IGG2M4 NUCLEIC ACID |
| SEQ ID NO: 96 | 10G5H6 HEAVY CHAIN IGG2M4 |
| SEQ ID NO: 97 | IGG1 FC |
| SEQ ID NO: 98 | IGG2 FC |
| SEQ ID NO: 99 | IGG4 FC |
| SEQ ID NO: 100 | IGG2M4 FC |
| SEQ ID NO: 101 | Mature human IL-13 receptor α1 |
| SEQ ID NO: 103 | hIL-13Rα1.ECR |
| SEQ ID NO: 104 | Mature cynomolgus IL-13Rα1 sequence |
| SEQ ID NO: 105 | Mature murine IL-13Rα1 sequence |
| SEQ ID NO: 106 | VH CDR1 NUCLEIC ACID |
| SEQ ID NO: 107 | VH CDR2 NUCLEIC ACID |
| SEQ ID NO: 108 | VH CDR3 NUCLEIC ACID |
| SEQ ID NO: 109 | VL CDR1 NUCLEIC ACID |
| SEQ ID NO: 110 | VL CDR2 NUCLEIC ACID |
| SEQ ID NO: 111 | VL CDR3 NUCLEIC ACID |
| SEQ ID NO: 112 | VH CDR3 10G5-6 NUCLEIC ACID |
| SEQ ID NO: 113 | VL CDR3 10G5-6 NUCLEIC ACID |
| SEQ ID NO: 120 | Mutant human IL-13 receptor α1 |
| SEQ ID NO: 121 | VH CDR3 |
| SEQ ID NO: 122 | VL CDR3 |
| SEQ ID NO: 123 | VL CDR1 NUCLEIC ACID |

*Note:
Where a particular SEQ ID NO: is relevant to more than one designated antibody, the following format may be utilized as an abbreviation of the different antibodies: Antibody Base Designation-One Assigned No., Another Assigned No., etc. An example of this is as follows: 10G5-1,3 refers to both 10G5-1 and 10G5-3.

In specific embodiments, the present invention provides isolated antibody molecules including a heavy chain variable region of SEQ ID NO:45, equivalents thereof characterized as having one or more conservative amino acid substitutions, and homologs thereof. The disclosed antibodies exhibit at least one of the following functional properties: (i) inhibition of IL-13-induced eotaxin release in NHDF cells; (ii) inhibition of IL-4-induced eotaxin release in NHDF cells; (iii) inhibition of IL-13-induced STAT6 phosphorylation in NHDF cells; (iv) inhibition of IL-4-induced STAT6 phosphorylation in NHDF cells; or (v) inhibition of IL-13-stimulated release of TARC in blood or PBMCs. In specific embodiments, the present invention provides homologs of the disclosed antibody molecules characterized as being at least 90% homologous thereto and exhibiting at least one of the above functional properties. Specific antibodies provided will compete for binding to hIL-13Rα1 with an antibody as produced by the hybridoma cell line deposited as ATCC Deposit No. PTA-6933.

In specific embodiments, the present invention provides isolated antibody molecules including a light chain variable region of SEQ ID NO:49, equivalents thereof characterized as having one or more conservative amino acid substitutions, and homologs thereof. The disclosed antibodies exhibit at least one of the following functional properties: (i) inhibition of IL-13-induced eotaxin release in NHDF cells; (ii) inhibition of IL-4-induced eotaxin release in NHDF cells; (iii) inhibition of IL-13-induced STAT6 phosphorylation in NHDF cells; (iv) inhibition of IL-4-induced STAT6 phosphorylation in NHDF cells; and (v) inhibition of IL-13-stimulated release of TARC in blood or PBMCs. In specific embodiments, the present invention provides homologs of the disclosed antibody molecules characterized as being at least 90% homologous thereto and exhibiting at least one of the above functional properties. Specific antibodies provided will compete for binding to hIL-13Rα1 with an antibody as produced by the hybridoma cell line deposited as ATCC Deposit No. PTA-6933.

In specific embodiments, the present invention provides isolated antibody molecules which comprise a heavy chain variable region comprising SEQ ID NO:45 and light chain variable region comprising SEQ ID NO:49; or equivalent thereof characterized as having one or more conservative amino acid substitutions. Specific embodiments are said antibodies which exhibit at least one of the following functional properties: (i) inhibition of IL-13-induced eotaxin release in NHDF cells; (ii) inhibition of IL-4-induced eotaxin release in NHDF cells; (iii) inhibition of IL-13-induced STAT6 phosphorylation in NHDF cells; (iv) inhibition of IL-4-induced STAT6 phosphorylation in NHDF cells; and (v) inhibition of IL-13-stimulated release of TARC in blood or PBMCs.

In particular embodiments, the present invention provides isolated IL-13Rα1 antibody molecules that include the variable heavy CDR3 sequence, SEQ ID NO:40, and conservative modifications thereof, which exhibit at least one of the following functional properties: (i) inhibition of IL-13-induced eotaxin release in NHDF cells; (ii) inhibition of IL-4-induced eotaxin release in NHDF cells; (iii) inhibition of IL-13-induced STAT6 phosphorylation in NHDF cells; (iv) inhibition of IL-4-induced STAT6 phosphorylation in NHDF cells; and (v) inhibition of IL-13-stimulated release of TARC in blood or PBMCs. Heavy chain variable region CDR3 sequences particularly embraced by the present invention are listed in Table 2.

TABLE 2

| SEQ ID NO: | $V_H$ CDR3 Sequence |
|---|---|
| SEQ ID NO: 1 | FPNWGALDQ |
| SEQ ID NO: 2 | VPNWGSLDT |
| SEQ ID NO: 3 | FPNWGSMDA |
| SEQ ID NO: 4 | FPNWGSLDH |

TABLE 2 -continued

| SEQ ID NO: | $V_H$ CDR3 Sequence |
|---|---|
| SEQ ID NO: 5 | MPNWGSFDY |
| SEQ ID NO: 6 | MPNWGSFDT |
| SEQ ID NO: 7 | MPNWGSLDH |
| SEQ ID NO: 8 | MPNWGSFDS |
| SEQ ID NO: 9 | MPNWGSLDT |
| SEQ ID NO: 10 | MPNWGSLDA |
| SEQ ID NO: 11 | MPNWGSLDN |
| SEQ ID NO: 12 | MPNWGALDS |
| SEQ ID NO: 13 | MPNWGSFDN |
| SEQ ID NO: 14 | MPNWGSLDY |
| SEQ ID NO: 15 | MPNWGSFDH |
| SEQ ID NO: 16 | MPNWGSLDS |
| SEQ ID NO: 17 | MPNWGSLDG |
| SEQ ID NO: 18 | VPNWGSLDN |
| SEQ ID NO: 19 | CARFPNWGSLDHWGQGTLVTVSSASIKG |
| SEQ ID NO: 20 | CARMPNWGSLDHWGQGTLVTVSSASTKG |
| SEQ ID NO: 21 | CARMPNWGSFDYWGQGTLVTVSSASIKG |
| SEQ ID NO: 22 | VRMPNWGSLDHW |
| SEQ ID NO: 23 | VRMPNWGSLDHWGQGTLVTVSSASIKG |
| SEQ ID NO: 24 | ARMPNWGSLDHWGQGTLVTVSSASIKG |
| SEQ ID NO: 25 | FPNWGSFDYWGQGTLVTVSSASIKG |
| SEQ ID NO: 26 | VPNWGSLDA |

TABLE 3

| SEQ ID NO: | $V_L$ CDR3 Sequence |
|---|---|
| SEQ ID NO: 27 | QRYAT |
| SEQ ID NO: 28 | QRYST |
| SEQ ID NO: 29 | QMYST |
| SEQ ID NO: 30 | QQVGT |
| SEQ ID NO: 31 | QVYST |
| SEQ ID NO: 32 | QQYST |
| SEQ ID NO: 33 | QSYST |
| SEQ ID NO: 34 | QQYAT |
| SEQ ID NO: 35 | QQYSS |
| SEQ ID NO: 36 | QTYST |
| SEQ ID NO: 37 | QQYGS |
| SEQ ID NO: 38 | QQYAS |
| SEQ ID NO: 39 | QQYEA |

Specific embodiments provide isolated antibody molecules which include a heavy chain variable region wherein CDR1, CDR2, and/or CDR3 sequences are SEQ ID NO:82, SEQ ID NO:83 and/or SEQ ID NO:40, respectively; or equivalents thereof characterized as having one or more conservative amino acid substitutions in any one ore more of the CDR sequences. Additional select embodiments provide isolated antibody molecules that include a heavy chain variable region wherein CDR1, CDR2, and/or CDR3 sequences are SEQ ID NO:82, SEQ ID NO:102, and/or SEQ ID NO:40, respectively; or equivalents thereof characterized as having one or more conservative amino acid substitutions in any one or more of the CDR sequences.

In particular embodiments, the present invention provides isolated IL-13Rα1 antibody molecules which have a variable light CDR3 sequence of SEQ ID NO:41, and conservative modifications thereof, which exhibit at least one of the following functional properties: (i) inhibition of IL-13-induced eotaxin release in NHDF cells; (ii) inhibition of IL-4-induced eotaxin release in NHDF cells; (iii) inhibition of IL-13-induced STAT6 phosphorylation in NHDF cells; (iv) inhibition of IL-4-induced STAT6 phosphorylation in NHDF cells; and (v) inhibition of IL-13-stimulated release of TARC in blood or PBMCs. Light chain variable region CDR3 sequences particularly embraced by the present invention are listed in Table 3.

Specific embodiments provide isolated antibody molecules which include a light chain variable region wherein CDR1, CDR2, and/or CDR3 sequences are set forth in SEQ ID NO:84, SEQ ID NO:85, and/or SEQ ID NO:41, respectively; or an equivalent thereof characterized as having one or more conservative amino acid substitutions in any one or more of the CDR sequences.

In particular embodiments, the present invention provides isolated IL-13Rα1 antibody molecules which include heavy chain variable region CDR3 sequence and light chain variable region CDR3 sequence of SEQ ID NOs:40 and 41, respectively, or conservative modifications thereof in any one or more of the CDR3 sequences, that exhibit at least one of the following functional properties: (i) inhibition of IL-13-induced eotaxin release in NHDF cells; (ii) inhibition of IL-4-induced eotaxin release in NHDF cells; (iii) inhibition of IL-13-induced STAT6 phosphorylation in NHDF cells; (iv) inhibition of IL-4-induced STAT6 phosphorylation in NHDF cells; and (v) inhibition of IL-13-stimulated release of TARC in blood or PBMCs.

Specific embodiments provide isolated IL-13Rα1 antibody molecules which include heavy chain variable region CDR1, CDR2, and CDR3 sequences and light chain variable region CDR1, CDR2, and CDR3 sequences of SEQ ID NOs: 82, 83, 40, 84, 85 and 41, respectively; and equivalents thereof characterized as having one or more conservative amino acid substitutions in any one or more of the CDR sequences.

Conservative amino acid substitutions, as one of ordinary skill in the art will appreciate, are substitutions that replace an amino acid residue with one imparting similar or better (for the intended purpose) functional and/or chemical characteristics. For example, conservative amino acid substitutions are often ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagines, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Such modifications do not significantly reduce or alter the binding or functional inhibition characteristics of the antibody containing the amino acid sequence but may improve such properties. The purpose for making a substitution is not significant and can include, but is by no means limited to, replacing a residue with one better able to maintain or enhance the structure of the molecule, the charge or hydrophobicity of the molecule, or the size of the molecule. For instance, one may desire simply to substitute a less desired residue with one of the same polarity or charge. Such modifications can be introduced by standard techniques known in the art, such as site-directed mutagenesis and PCR-mediated mutagenesis. One specific means by which those of skill in the art accomplish conservative amino acid substitutions is alanine scanning mutagenesis as discussed in, for example, MacLennan et al., 1998 *Acta Physiol. Scand. Suppl.* 643:55-67, and Sasaki et al., 1998 *Adv. Biophys.* 35:1-24. The altered antibody molecules are then tested for retained or better function using functional assays available in the art or described herein. Antibody molecules possessing one or more such conservative amino acid substitutions which retain the ability to selectively bind to hIL-13Rα1 and antagonize IL-13Rα1 functioning at a level the same or better than the molecule not possessing such amino acid alterations are referred to herein as "functional equivalents" of the disclosed antibodies and form specific embodiments of the present invention.

In another aspect, the present invention provides antibody molecules which include heavy and/or light chain variable regions comprising amino acid sequences that are homologous to the corresponding amino acid sequences of the disclosed antibodies, wherein the antibody molecules exhibit an equilibrium dissociation constant ($K_D$) of less than 5 nM with human interleukin 13 receptor α1 (hIL-13Rα1) and antagonize hIL-13Rα1-mediated activity. Specific embodiments are antibody molecules which include heavy and/or light chain variable regions which are at least 90% homologous to disclosed heavy and/or light chain variable regions, respectively, that exhibit at least one of the following functional properties: (i) inhibition of IL-13-induced eotaxin release in NHDF cells; (ii) inhibition of IL-4-induced eotaxin release in NHDF cells; (iii) inhibition of IL-13-induced STAT6 phosphorylation in NHDF cells; (iv) inhibition of IL-4-induced STAT6 phosphorylation in NHDF cells; or (v) inhibition of IL-13-stimulated release of TARC in blood or PBMCs. Other embodiments of the present invention are antibody molecules which include heavy and/or light chain variable regions which are at least 90% homologous to disclosed heavy and/or light chain variable regions, respectively, that compete for binding to hIL-13Rα1 with an antibody as produced by the hybridoma cell line deposited as ATCC Deposit No. PTA-6933. Reference to "at least 90% homologous" in variable regions includes at least 90, 91, 92, 93, 94, 95, 96, 97, 98, 99 and 100% homologous sequences.

Antibodies with amino acid sequences homologous to the amino acid sequences of the specific antibody molecules described herein are typically produced to improve one or more of the properties of the antibody without changing its specificity for IL-13Rα1. One method of obtaining such sequences, which is not the only method available to the skilled artisan, is to mutate sequence encoding heavy and/or light chain variable regions disclosed herein by site-directed or random mutagenesis, express an antibody molecule comprising the mutated variable region(s), and test the encoded antibody molecule for retained function using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and length of each gap, which need to be introduced for optimal alignment of the two sequences. The comparison of sequences and determination of percent identity between sequences can be determined using methods generally known to those in the art and can be accomplished using a mathematical algorithm. For example, the percent identity between amino acid sequences and/or nucleotide sequences can be determined using the algorithm of Meyers and Miller, 1988 *Comput. Appl. Biosci.* 4:11-17, which has been incorporated into the ALIGN program (version 2.0). In addition, the percent identity between amino acid sequences or nucleotide sequences can be determined using the GAP program in the GCG software package available online from Accelrys, using its default parameters.

Specific antibodies of the present invention inhibit the binding of IL-13 to hIL-13Rα1. Specific antibodies of the present invention compete for binding to hIL-13Rα1 with any of the antibodies disclosed herein and, particularly, 10G5. Such competing antibodies can be identified based on their ability to cross-compete (e.g., to competitively inhibit the binding of, in a statistically significant manner) with 10G5 or its derivatives disclosed herein in standard IL-13Rα1 binding assays. The ability of a test antibody to inhibit the binding of 10G5 or derivative to human IL-13Rα1 demonstrates that the test antibody can compete with that antibody for binding to human IL-13Rα1. Such an antibody may, according to non-limiting theory, bind to the same or a related (e.g., a structurally similar or spatially proximal) epitope on human IL-13Rα1 as the antibody with which it competes. Antibodies that compete for binding with 10G5 or its disclosed derivatives may then be assessed for having at least one of the following functional properties: (i) inhibition of IL-13-induced eotaxin release in NHDF cells; (ii) inhibition of IL-4-induced eotaxin release in NHDF cells; (iii) inhibition of IL-13-induced STAT6 phosphorylation in NHDF cells; (iv) inhibition of IL-4-induced STAT6 phosphorylation in NHDF cells; and (v) inhibition of IL-13-stimulated release of TARC in blood or PBMCs. The antibodies can also then be assessed for binding sensitivity at the Phe233Ala residue of human IL-13Rα1 described herein.

In particular embodiments, the present invention provides isolated antibody molecules that antagonize IL-13Rα1 function (IL-13Rα1-mediated activity) and which exhibit an equilibrium dissociation constant ($K_D$) with hIL-13Rα1 which is less than 200 pM, and preferably less than 100 pM, as determined by surface plasmon resonance technologies readily available and understood by those of skill in the art, including but not limited to, BIACORE' (Upsala, Sweden) and KINEXA® (Sapidyne Instruments, Boise, Id.) or suitable equivalent thereof. In specific embodiments, the isolated antibody molecules exhibit the above $K_D$ as well as one of the following functional properties: (i) inhibition of IL-13-induced eotaxin release in NHDF cells; (ii) inhibition of IL-4-induced eotaxin release in NHDF cells; (iii) inhibition of IL-13-induced STAT6 phosphorylation in NHDF cells; (iv) inhibition of IL-4-induced STAT6 phosphorylation in NHDF cells; and (v) inhibition of IL-13-stimulated release of TARC in blood or PBMCs.

In specific embodiments, the present invention provides isolated antibody molecules which exhibit the above $K_D$, antagonize IL-13Rα1-mediated activity, and comprise a heavy chain variable region with a complementarity determining region 3 (CDR3) domain as set forth in SEQ ID NO:5 or an equivalent thereof characterized as having conservative amino acid substitutions at amino acid positions 1, 7, and/or 9 therein. In specific embodiments, the present invention provides isolated antibody molecules which exhibit the above $K_D$ and heavy chain variable region and further include a light chain variable region with a CDR3 domain as set forth in SEQ ID NO:38 or an equivalent thereof characterized as having conservative amino acid substitutions at amino acid positions 2, 4, and/or 5 therein. In specific embodiments, such conservative amino acid substitutions encompass the following:

in SEQ ID NO:5, position 1, a substitution selected from the group consisting of: a F, M, Q, L and V;

in SEQ ID NO:5, position 7, a substitution selected from the group consisting of: a F, L, A and M;

in SEQ ID NO:5, position 9, a substitution selected from the group consisting of: a Y, Q, K, R, W and H;

in SEQ ID NO:38, position 2, a substitution selected from the group consisting of: Q, R, M, S and T;

in SEQ ID NO:38, position 4, a substitution selected from the group consisting of: E, A, G and S; and/or in SEQ ID NO:38, position 5, a substitution selected from the group consisting of: T, A and S.

Accordingly, one embodiment of the present invention embraces an antibody molecule with a heavy chain variable region CDR3 having the sequence Xaa$_1$-Pro-Asn-Trp-Gly-Xaa$_2$-Xaa$_3$-Asp-Xaa$_4$ (SEQ ID NO:121), wherein Xaa$_1$ is Phe, Met, Gln, Leu or Val; Xaa$_2$ is Ser or Ala; Xaa$_3$ is Phe, Leu, Ala or Met; and Xaa$_4$ is Tyr, Gln, Lys, Arg, Trp, His, Ala, Thr, Ser, Asn or Gly. Another embodiment embraces an antibody molecule with a light chain variable region CDR3 having the sequence Gln-Xaa$_1$-Xaa$_2$-Xaa$_3$-Xaa$_4$ (SEQ ID NO:122), wherein Xaa$_1$ is Gln, Arg, Met, Ser, Thr or Val; Xaa$_2$ is Tyr or Val; Xaa$_3$ is Glu, Ala, Gly or Ser; and Xaa$_4$ is Thr, Ala or Ser.

One aspect of the present invention is an isolated antibody or antigen binding fragment that includes:

a heavy chain variable region with a CDR3 domain having a sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, and SEQ ID NO:26; or a heavy chain variable region with a sequence including a CDR3 domain, said sequence selected from the group consisting of: SEQ ID NO:19, SEQ ID NO:20, SEQ ID NO:21, SEQ ID NO:22, SEQ ID NO:23, SEQ ID NO:24, and SEQ ID NO:25; and/or a light chain variable region with a CDR3 domain having a sequence selected from the group consisting of: SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 and SEQ ID NO:39;

wherein specific embodiments thereof exhibit a $K_D$ with hIL-13Rα1 which is less than 200 pM.

Specific embodiments have a heavy chain including a sequence selected from the group consisting of: SEQ ID NO:50, SEQ ID NO:54, SEQ ID NO:58, SEQ ID NO:62, and SEQ ID NO:66. Specific embodiments have a heavy chain variable domain including a sequence selected from the group consisting of: SEQ ID NO:51, SEQ ID NO:55, SEQ ID NO:59, SEQ ID NO:63, and SEQ ID NO:67. Specific embodiments have a light chain having a sequence selected from the group consisting of: SEQ ID NO:70, SEQ ID NO:74, and SEQ ID NO:78. Specific embodiments have a light chain variable domain having a sequence selected from the group consisting of: SEQ ID NO:71, SEQ ID NO:75, and SEQ ID NO:79.

Another aspect of the present invention is an isolated antibody or antigen binding fragment in accordance with the present disclosure that possesses the following:

a light chain variable region including a CDR2 domain with the sequence set forth in SEQ ID NO:85;

a heavy chain variable region including a CDR2 domain with the sequence set forth in SEQ ID NO:83;

a light chain variable region including a CDR1 domain with the sequence set forth in SEQ ID NO:84; and/or a heavy chain variable region including a CDR1 domain with the sequence set forth in SEQ ID NO:82.

Accordingly, specific embodiments of the present invention provide antibody molecules specific for human IL-13 receptor which include an antigen binding region having heavy and light chain variable regions, and a set of CDRs (CDR1, CDR2, and CDR3) as described herein. The present invention also provides compositions including one and/or both of the following components (1) a heavy chain variable region having a set of CDRs, and (2) a light chain variable region having a set of CDRs.

In one aspect, the present invention provides isolated antibody molecules for human IL-13Rα1 which have therein at least one light chain variable domain and at least one heavy chain variable domain ($V_L$ and $V_H$, respectively).

In specific embodiments, an antibody molecule having a heavy chain variable chain region in accordance with the present description is expressed with a light chain variable region with CDR3 sequence as set forth in SEQ ID NO:41. In other embodiments, an antibody molecule having a light chain variable region in accordance with the present description is expressed with a heavy chain variable sequence with CDR3 sequence as set forth in SEQ ID NO:40. In specific embodiments, light and heavy chains of the formulas described above are used in combination. Specific embodiments of the present invention provide antibody molecules that further include the following:

a light chain variable region with a CDR2 domain as set forth in SEQ ID NO:85;

a heavy chain variable region with a CDR2 domain as set forth in SEQ ID NO:83;

a light chain variable region with a CDR1 domain as set forth in SEQ ID NO:84; and/or a heavy chain variable region with a CDR1 domain as set forth in SEQ ID NO:82, or suitable equivalents or derivatives thereof, including said domains containing conservative amino acid substitutions as described above.

Any antibody molecule including the disclosed heavy and/or light CDRs, variable regions or light or heavy chains, or any combination thereof is encompassed within the present invention including, but not limited to, the following antibody molecules: (1) an isolated antibody molecule having a heavy chain variable region having therein CDR3 sequence as set forth in SEQ ID NO:5, and a light chain variable region having therein CDR3 sequence as set forth in SEQ ID NO:38; (2) an isolated antibody molecule having a heavy chain variable region having therein CDR3 sequence as set forth in SEQ ID NO:5, and a light chain variable region having therein CDR3 sequence as set forth in SEQ ID NO:39; (3) an isolated antibody molecule having a heavy chain variable region having therein CDR3 sequence as set forth in SEQ ID NO:5, and a light chain variable region having therein CDR3 sequence as set forth in SEQ ID NO:41; (4) an isolated antibody molecule having a heavy chain variable region having therein CDR3 sequence as set forth in SEQ ID NO:22, and a light chain variable region having therein CDR3 sequence as set forth in SEQ ID NO:38; (5) an isolated antibody molecule having a heavy chain variable region having therein CDR3 sequence as set forth in SEQ ID NO:23, and a light chain variable region having therein CDR3 sequence as set forth in SEQ ID NO:38; and (6) an isolated antibody molecule having a heavy chain variable region having therein CDR3 sequence as set forth in SEQ ID NO:7, and a light chain variable region having therein CDR3 sequence as set forth in SEQ ID NO:38.

In some embodiments, an isolated antibody of the present invention has a light chain variable region including a CDR2 domain with the sequence set forth in SEQ ID NO:85; a heavy chain variable region including a CDR2 domain with the sequence set forth in SEQ ID NO:83; a light chain variable region including a CDR1 domain with the sequence set forth in SEQ ID NO:84; and a heavy chain variable region including a CDR1 domain with the sequence set forth in SEQ ID NO:82.

In other embodiments an isolated antibody molecule of the invention has a heavy chain variable region with CDR1, CDR2 and CDR3 sequences as set forth in SEQ ID NO:82, SEQ ID NO:83, and SEQ ID NO:7 respectively, and a light chain variable region including CDR1, CDR2 and CDR3 sequences as set forth in SEQ ID NO:84, SEQ ID NO:85, and SEQ ID NO:38 respectively.

Further encompassed herein are antibody molecules including (i) a heavy chain variable region as set forth in SEQ ID NO:63 and/or a light chain variable region as set forth in SEQ ID NO:71; (ii) a heavy chain as set forth in SEQ ID NO:62 and a light chain variable region as set forth in SEQ ID NO:71, and (iii) a heavy chain as set forth in SEQ ID NO:94 and a light chain variable region as set forth in SEQ ID NO:71.

Manipulation of monoclonal and other antibodies to produce other antibodies or chimeric molecules which retain the specificity of the original antibody is well within the realm of one skilled in the art. This can be accomplished, for example, using techniques of recombinant DNA technology. Such techniques may involve the introduction of DNA encoding the immunoglobulin variable region, or one or more of the CDRs, of an antibody to the variable region, constant region, or constant region plus framework regions, as appropriate, of a different immunoglobulin. Such molecules form important aspects of the present invention. Specific immunoglobulins, into which the disclosed sequences may be inserted or, in the alternative, form the essential part of, include but are not limited to the following antibody molecules which form particular embodiments of the present invention: a Fab (monovalent fragment with variable light ($V_L$), variable heavy ($V_H$), constant light ($C_L$) and constant heavy 1 ($C_{H1}$) domains), a F(ab')$_2$ (bivalent fragment comprising two Fab fragments linked by a disulfide bridge or alternative at the hinge region), a Fd ($V_H$ and $C_{H1}$ domains), a Fv ($V_L$ and $V_H$ domains), a scFv (a single chain Fv where $V_L$ and $V_H$ are joined by a linker, e.g., a peptide linker, see, e.g., Bird et al., 1988 Science 242:423-426, Huston et al., 1988 Proc. Natl. Acad. Sci. USA 85:5879-5883), a bispecific antibody molecule (an antibody molecule comprising an IL-13Rα1-specific antibody or antigen binding fragment as disclosed herein linked to a second functional moiety having a different binding specificity than the antibody, including, without limitation, another peptide or protein such as an antibody, or receptor ligand), a bispecific single chain Fv dimer (see, e.g., PCT/US92/09965), an isolated CDR3, a minibody (single chain-$C_{H3}$ fusion that self assembles into a bivalent dimer of about 80 kDa), a 'scAb' (an antibody fragment containing $V_H$ and $V_L$ as well as either $C_L$ or $C_{H1}$), a dAb fragment ($V_H$ domain, see, e.g., Ward et al., 1989 Nature 341:544-546, and McCafferty et al., 1990 Nature 348:552-554; or $V_L$ domain; Holt et al., 2003 Trends in Biotechnology 21:484-489), a diabody (see, e.g., Holliger et al., 1993 Proc. Natl. Acad. Sci. USA 90:6444-6448 and WO 94/13804), a triabody, a tetrabody, a minibody (a scFv joined to a $C_{H3}$; see, e.g., Hu et al., 1996 Cancer Res. 56:3055-3061), IgG, IgG1, IgG2, IgG3, IgG4, IgM, IgD, IgA, IgE or any derivatives thereof, and artificial antibodies based upon protein scaffolds, including but not limited to fibronectin type III polypeptide antibodies (see, e.g., U.S. Pat. No. 6,703,199 and WO 02/32925) or cytochrome B; see, e.g., Koide et al., 1998 J. Mol. Biol. 284:1141-1151, and Nygren et al., 1997 Current Opinion in Structural Biology 7:463-469. Certain antibody molecules including, but not limited to, Fv, scFv, and diabody molecules may be stabilized by incorporating disulfide bridges to line the $V_H$ and $V_L$ domains, see, e.g., Reiter et al., 1996 Nature Biotech. 14:1239-1245. Bispecific antibodies may be produced using conventional technologies (see, e.g., Holliger & Winter, 1993 Current Opinion Biotechnol. 4:446-449, specific methods of which include production chemically, or from hybrid hybridomas) and other technologies including, but not limited to, the BITE technology (molecules possessing antigen binding regions of different specificity with a peptide linker) and knobs-into-holes engineering (see, e.g., Ridgeway et al., 1996 Protein Eng. 9:616-621). Bispecific diabodies may be produced in E. coli, and these molecules as well as other antibody molecules, as one of skill in the art will appreciate, may be selected using phage display in the appropriate libraries (see, e.g., WO 94/13804).

Variable domains, into which CDRs of interest are inserted, may be obtained from any germ-line or rearranged human variable domain. Variable domains may also be synthetically produced. The CDR regions can be introduced into the respective variable domains using recombinant DNA technology. One means by which this can be achieved is described in Marks et al., 1992 Bio/Technology 10:779-783. Expression and selection may be achieved using suitable technologies including, but not limited to phage display (see, e.g., WO 92/01047, Kay et al., 1996 Phage Display of Peptides and Proteins: A Laboratory Manual, San Diego: Academic Press), yeast display, bacterial display, T7 display, and ribosome display (see, e.g., Lowe & Jermutus, 2004 Curr. Pharm. Biotech. 517-527). A variable heavy domain may be paired with a variable light domain to provide an antigen binding site. In addition, independent regions (e.g., a variable heavy domain alone) may be used to bind antigen. The artisan is well aware, as well, that two domains of an Fv fragment, $V_L$ and $V_H$, while perhaps coded by separate genes, may be joined, using recombinant methods, by a synthetic linker that enables them to be made as a single protein chain in which the $V_L$ and $V_H$ regions pair to form monovalent molecules (scFvs).

Specific embodiments provide the CDR(s) in germline framework regions. Specific embodiments herein provide heavy chain CDR(s) of interest into VH5-51 (JH4) in place of the relevant CDR(s); as, for example, in SEQ ID NOs:50, 54, 58, 62, and 66. Specific embodiments herein provide the light chain CDR(s) into Vκ3 A27 (JK1) in place of the relevant CDR(s); as, for example, in SEQ ID NOs:70, 74, and 78.

The present invention encompasses antibody molecules that are human, humanized, deimmunized, chimeric and primatized. The invention also encompasses antibodies produced by the process of veneering; see, e.g., Mark et al., 1994 Handbook of Experimental Pharmacology, vol. 113: The pharmacology of monoclonal Antibodies, Springer-Verlag, pp. 105-134 and U.S. Pat. No. 6,797,492. "Human" in reference to the disclosed antibody molecules specifically refers to antibody molecules having variable and/or constant regions derived from human germline immunoglobulin sequences, wherein said sequences may, but need not, be modified/altered to have certain amino acid substitutions or residues that are not encoded by human germline immunoglobulin sequence. Such mutations can be introduced by methods including, but not limited to, random or site-specific mutagenesis in vitro, or by somatic mutation in vivo. Specific examples of mutation techniques discussed in the literature are that disclosed in Gram et al., 1992 *Proc. Natl. Acad. Sci. USA* 89:3576-3580; Barbas et al., 1994 *Proc. Natl. Acad. Sci. USA* 91:3809-3813, and Schier et al., 1996 *J. Mol. Biol.* 263:551-567. These are only specific examples and do not represent the only available techniques. There are a plethora of mutation techniques in the scientific literature which are available to, and widely appreciated by, the skilled artisan. "Humanized" in reference to the disclosed antibody molecules refers specifically to antibody molecules wherein CDR sequences derived from another mammalian species, such as a mouse, are grafted onto human framework sequences. "Primatized" in reference to the disclosed antibody molecules refers to antibody molecules wherein CDR sequences of a non-primate are inserted into primate framework sequences, see, e.g., WO 93/02108 and WO 99/55369.

Specific antibodies of the present invention are monoclonal antibodies and, in particular embodiments, are in one of the following antibody formats: IgD, IgA, IgE, IgM, IgG1, IgG2, IgG3, IgG4 or any derivative of any of the foregoing. The language "derivatives thereof" or "derivatives" includes, inter alia, (i) antibodies and antibody molecules with modifications in the framework or CDR regions of one or both variable regions (i.e., $V_H$ and/or $V_L$), (ii) antibodies and antibody molecules with manipulations in the constant regions of the heavy and/or light chains, and (iii) antibodies and antibody molecules that contain additional chemical moieties which are not normally a part of the immunoglobulin molecule (e.g., pegylation).

Manipulations of the variable regions can be within one or more of the $V_H$ and/or $V_L$ CDR regions. Site-directed mutagenesis or random mutagenesis can be performed to introduce the mutation(s) and the effect on antibody functional property of interest can be evaluated using can be evaluated by available in vitro or in vivo assays including those described herein.

Antibodies of the present invention also include those in which modifications have been made to the framework residues within $V_H$ and/or $V_L$ to improve one or more properties of the antibody of interest. Typically, such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. Such "backmutated" antibodies are also intended to be encompassed by the invention. Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, where present, typically to alter one or more functional properties of the antibody, such as serum half-life, complement fixation, Fc receptor binding, and/or antigen-dependent cellular cytotoxicity.

In one embodiment, the hinge region of $C_{H1}$ is modified such that the number of cysteine residues in the hinge region is altered, e.g., increased or decreased, to, for example, facilitate assembly of the light and heavy chains or to increase or decrease the stability of the antibody. This approach is described further in U.S. Pat. No. 5,677,425 by Bodmer et al.

In another embodiment, the Fc hinge region of an antibody is mutated to decrease the biological half-life of the antibody. This approach is described in further detail in U.S. Pat. No. 6,165,745 by Ward et al.

In another embodiment, the antibody is modified to increase its biological half-life. Various approaches are possible. For example, one or more of the following mutations can be introduced: Thr252Leu, Thr254Ser, Thr256Phe, as described in U.S. Pat. No. 6,277,375 by Ward. Alternatively, to increase the biological half-life, the antibody can be altered within the $C_{H1}$ or CL region to contain a salvage receptor binding epitope taken from two loops of a $C_{H2}$ domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, see U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are modified to thereby alter the ability of the antibody to fix complement. This approach is described further in WO 94/29351 by Bodmer et al.

In yet another example, the Fc region is modified to increase the ability of the antibody to mediate antibody-dependent cellular cytotoxicity (ADCC) and/or to increase the affinity of the antibody for an Fcγ receptor by modifying one or more amino acids; see for example WO 00/42072 by Presta. Moreover, the binding sites on human IgG1 for FcγR1, FcγRII, FcγRIII and FcRn have been mapped and variants with improved binding have been described (see Shields et al, *J. Biol. Chem.* 276:6591-6604, 2001).

The concept of generating "hybrids" or "combinatorial" IgG forms comprising various antibody isotypes to hone in on desired effector functionality has generally been described; see, e.g., Tao et al., 1991 *J. Exp. Med.* 173:1025-1028. A specific embodiment of the present invention encompasses antibody molecules that possess specific manipulations in the Fc region which have been found to result in reduced binding to FcγR receptors or C1q on the part of the antibody. The present invention, therefore, encompasses antibodies in accordance with the present description that do not provoke (or provoke to a lesser extent) antibody-dependent cellular cytotoxicity (ADCC), complement-mediated cytotoxicity (CMC), or form immune complexes, while retaining normal pharmacokinetic (PK) properties. Specific embodiments of the present invention provide an antibody molecule as defined in accordance with the present invention which includes, as part of its immunoglobulin structure, the sequence set forth in SEQ ID NO:92. FIG. 16 illustrates a comparison of IgG2 m4 (as described in U.S. Patent Publication No. US20070148167 (A1)), which contains SEQ ID NO:92, with the amino acid sequence of IgG1, IgG2, and IgG4. One specific example of the above-described embodiment is an antibody molecule including SEQ ID NO:94 which possesses sequence based off of a 10G5-6 antibody. Another specific example of the above-described embodiment is an antibody molecule including SEQ ID NO:96 which possesses sequence based off of an 10G5H6 antibody.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation."

Specific antibody molecules may carry a detectable label, or may be conjugated to a toxin (e.g., a cytotoxin), a radioactive isotope, a radionuclide, a liposome, a targeting moiety, a biosensor, a cationic tail, or an enzyme (e.g., via a peptidyl bond or linker). Such antibody molecule compositions form an additional aspect of the present invention.

In another aspect, the present invention provides isolated nucleic acid encoding the disclosed antibody molecules. The nucleic acid may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, for example, using standard techniques, including without limitation, alkaline/SDS treatment, CsCl banding, column chromatography, agarose gel electrophoresis and other suitable methods known in the art. The nucleic acid may include DNA (inclusive of cDNA) and/or RNA. Nucleic acids of the present invention can be obtained using standard molecular biology techniques. For antibodies expressed by hybridomas (e.g., hybridomas prepared from transgenic mice carrying human immunoglobulin genes), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

The present invention encompasses isolated nucleic acid encoding the disclosed variable heavy and/or light chains and select components thereof, particularly the disclosed respective CDR3 regions. In specific embodiments hereof, the CDR(s) are provided within antibody framework regions. Specific embodiments provide isolated nucleic acid encoding the CDR(s) inserted into the germline framework regions. Specific embodiments herein provide isolated nucleic acid encoding the heavy chain CDR(s) inserted into a VH5-51 (JH4) germline in place of the nucleic acid encoding the corresponding CDR(s); as, for example, in SEQ ID NOs:52, 56, 60, 64 and 68. Specific embodiments herein provide isolated nucleic encoding the light chain CDR(s) inserted into Vκ3 A27 (JK1) germline in place of the nucleic acid encoding the corresponding CDR(s); as, for example, in SEQ ID NOs: 72, 76 and 80. The isolated nucleic acid encoding the variable regions can be provided within any desired antibody molecule format including, but not limited to, the following: F(ab')$_2$, a Fab, a Fv, a scFv, bispecific antibody molecules (antibody molecules comprising an IL-13Rα1-specific antibody or antigen binding fragment as disclosed herein linked to a second functional moiety having a different binding specificity than the antibody, including, without limitation, another peptide or protein such as an antibody, or receptor ligand), a bispecific single chain Fv dimer, a minibody, a dAb fragment, diabody, triabody or tetrabody, IgG, IgG1, IgG2, IgG3, IgG4, IgM, IgD, IgA, IgE or any derivatives thereof.

Specific embodiments provide isolated a nucleic acid encoding an antibody molecule including a heavy chain having a sequence selected from the group consisting of SEQ ID NO:52, SEQ ID NO:56, SEQ ID NO:60, SEQ ID NO:64, and SEQ ID NO:68. Specific embodiments provide isolated a nucleic acid encoding an antibody molecule including a heavy chain variable domain having a sequence selected from the group consisting of SEQ ID NO:43, SEQ ID NO:53, SEQ ID NO:57, SEQ ID NO:61, SEQ ID NO:65, and SEQ ID NO:69. Specific embodiments of the present invention provide an isolated nucleic acid encoding an antibody molecule including (i) heavy chain CDR1 nucleotide sequence SEQ ID NO:106, (ii) heavy chain CDR2 nucleotide sequence SEQ ID NO:107, and/or (iii) heavy chain CDR3 nucleotide sequence SEQ ID NO:108 or SEQ ID NO:112. Specific embodiments provide an isolated nucleic acid encoding an antibody molecule including a light chain having a sequence selected from the group consisting of SEQ ID NO:72, SEQ ID NO:76, and SEQ ID NO:80. Specific embodiments provide an isolated nucleic acid encoding an antibody molecule including a light chain variable domain having a sequence selected from the group consisting of SEQ ID NO:47, SEQ ID NO:73, SEQ ID NO:77, and SEQ ID NO:81. Specific embodiments of the present invention provide an isolated nucleic acid encoding an antibody molecule including (i) light chain CDR1 nucleotide sequence SEQ ID NO:109 or SEQ ID NO: 123, (ii) light chain CDR2 nucleotide sequence SEQ ID NO:110, and/or (iii) light chain CDR3 nucleotide sequence SEQ ID NO:111 or SEQ ID NO:113. Specific embodiments of the present invention encompass a nucleic acid encoding an antibody molecule that possesses manipulations in the Fc region which result in reduced binding to FcγR receptors or C1q on the part of the antibody. One specific embodiment of the present invention is an isolated nucleic acid which includes SEQ ID NO:93. One specific example of such embodiment is an antibody molecule including the sequence of SEQ ID NO:95, or nucleic acid encoding an antigen binding fragment of SEQ ID NO:94. In specific embodiments, synthetic antibody molecules can be produced by expression from nucleic acid generated from oligonucleotides synthesized and assembled within suitable expression vectors; see, e.g., Knappick et al., 2000 *J. Mol. Biol.* 296:57-86, and Krebs et al., 2001 *J. Immunol. Methods* 254:67-84.

Also included within the present invention are nucleic acids including nucleotide sequences which are at least about 90% identical and more preferably at least about 95% identical to the nucleotide sequences described herein, and which nucleotide sequences encode antibodies of the present invention. Sequence comparison methods to determine identity are known to those skilled in the art and include those discussed earlier. Reference to "at least about 90% identical" includes at least about 90, 91, 92, 93, 94, 95, 96, 97, 98, 99 or 100% identical.

The invention further provides nucleic acids that hybridize to the complement of nucleic acid disclosed herein (e.g., the complement of nucleic acid including (i) heavy chain nucleotide sequence SEQ ID NO:52, SEQ ID NO:56, SEQ ID NO:60, SEQ ID NO:64, SEQ ID NO:68 or SEQ ID NO:95, (ii) $V_H$ nucleotide sequence SEQ ID NO:43, SEQ ID NO:53, SEQ ID NO:57, SEQ ID NO:61, SEQ ID NO:65 or SEQ ID NO:69; (iii) heavy chain CDR1 nucleotide sequence SEQ ID NO:106, (iv) heavy chain CDR2 nucleotide sequence SEQ ID NO:107, (v) heavy chain CDR3 nucleotide sequence SEQ ID NO:108 or SEQ ID NO:112, (vi) light chain nucleotide sequence SEQ ID NO:72, SEQ ID NO:76 or SEQ ID NO:0, (vii) $V_L$ nucleotide sequence SEQ ID NO:47, SEQ ID NO:73, SEQ ID NO:77 or SEQ ID NO:81, (viii) light chain CDR1 nucleotide sequence SEQ ID NO:109 or SEQ ID NO: 123, (ix) light chain CDR2 nucleotide sequence SEQ ID NO:110, or (x) light chain CDR3 nucleotide sequence comprising SEQ ID NO:111 or SEQ ID NO:113) under particular hybridization conditions, which nucleic acids encode antibody molecules that bind specifically to hIL-13Rα1 and antagonize IL-13Rα1-mediated activity. Methods for hybridizing nucleic acids are well-known in the art; see, e.g., Ausubel, *Current Protocols in Molecular Biology*, John Wiley & Sons, N.Y., 6.3.1-6.3.6, 1989. As defined herein, moderately stringent hybridization conditions may use a prewashing solution containing 5× sodium chloride/sodium citrate (SSC), 0.5% w/v SDS, 1.0 mM EDTA (pH 8.0), hybridization buffer of about 50% v/v formamide, 6×SSC, and a hybridization temperature of 55° C. (or other similar hybridization solutions, such as one containing about 50% v/v formamide, with a hybridization temperature of 42° C.), and washing conditions of 60° C., in 0.5×SSC, 0.1% w/v SDS. A stringent hybridization condition may be at 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98, or 99% identical to each other typically remain hybridized to each other. The basic parameters affecting the choice of hybridization conditions and guidance for devising suitable conditions are set forth by Sambrook et al., *Molecular Cloning: A Laboratory Manual*, Cold Spring Harbor Laboratory Press, Cold Spring Harbor, N.Y., Chapters 9 and 11, 1989; and Ausubel et al. (eds), *Current Protocols in Molecular Biology*, John Wiley & Sons, Inc., sections 2.10 and 6.3-6.4, 1995, and can be readily determined by those having ordinary skill in the art based on, for example, the length and/or base composition of the DNA.

The present invention provides isolated antibodies which include a light and/or heavy chain variable domain that is encoded at least in part by a nucleotide sequence that hybridizes under moderately stringent conditions to the complement of a nucleic acid sequence encoding a light and/or heavy chain variable domain disclosed herein (e.g., selected from the group consisting of SEQ ID NO:43, SEQ ID NO:47, SEQ ID NO:53, SEQ ID NO:57, SEQ ID NO:61, SEQ ID NO:65, SEQ ID NO:69, SEQ ID NO:73, SEQ ID NO:77 and SEQ ID NO:81). In another embodiment, the present invention encompasses isolated antibodies which include a light and/or heavy chain variable domain that is encoded at least in part by a nucleotide sequence that hybridizes under stringent conditions to the complement of a nucleic acid sequence comprising a light and/or heavy chain variable domain disclosed herein.

In another aspect, the present invention provides vectors including said nucleic acid. Vectors in accordance with the present invention include, but are not limited to, plasmids and other expression constructs (e.g., phage or phagemid, as appropriate) suitable for the expression of the desired antibody molecule at the appropriate level for the intended purpose; see, e.g., Sambrook & Russell, *Molecular Cloning: A Laboratory Manual: 3rd Edition*, Cold Spring Harbor Laboratory Press. For most cloning purposes, DNA vectors may be used. Typical vectors include plasmids, modified viruses, bacteriophage, cosmids, yeast artificial chromosomes, and other forms of episomal or integrated DNA. It is well within the purview of the skilled artisan to determine an appropriate vector for a particular gene transfer, generation of a recombinant human antibody, or other use. In specific embodiments, in addition to a recombinant gene, the vector may also contain an origin of replication for autonomous replication in a host cell, appropriate regulatory sequences, such as a promoter, a termination sequence, a polyadenylation sequence, an enhancer sequence, a selectable marker, a limited number of useful restriction enzyme sites, other sequences as appropriate and the potential for high copy number. Examples of expression vectors for antibody and antibody fragment production are well-known in the art; see, e.g., Persic et al., 1997 *Gene* 187:9-18; Boel et al., 2000 *J. Immunol. Methods* 239: 153-166, and Liang et al., 2001 *J. Immunol. Methods* 247: 119-130. If desired, nucleic acid encoding an antibody may be integrated into the host chromosome using techniques well-known in the art; see, e.g., Ausubel, *Current Protocols in Molecular Biology*, John Wiley & Sons, 1999, and Marks et al., WO 95/17516. Nucleic acids may also be expressed on plasmids maintained episomally or incorporated into an artificial chromosome; see, e.g., Csonka et al., 2000 *J. Cell Science* 113:3207-3216; Vanderbyl et al., 2002 *Molecular Therapy* 5:10. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

Any technique available to the skilled artisan may be employed to introduce the nucleic acid into the host cell; see, e.g., Morrison, 1985 *Science,* 229:1202. Methods of subcloning nucleic acid molecules of interest into expression vectors, transforming or transfecting host cells containing the vectors, and methods of making substantially pure protein including the steps of introducing the respective expression vector into a host cell, and cultivating the host cell under appropriate conditions are well-known. The antibody so produced may be harvested from the host cells in conventional ways. Techniques suitable for the introduction of nucleic acid into cells of interest will depend on the type of cell being used. General techniques include, but are not limited to, calcium phosphate transfection, DEAE-Dextran, electroporation, liposome-mediated transfection and transduction using viruses appropriate to the cell line of interest (e.g., retrovirus, vaccinia, baculovirus, or bacteriophage).

In another aspect, the present invention provides isolated cell(s) including nucleic acid encoding the disclosed antibody molecules and components thereof as described. A variety of different cell lines can be used for recombinant production of antibody molecules, including but not limited to those from prokaryotic organisms (e.g., *E. coli, Bacillus,* and *Streptomyces*) and from eukaryotic (e.g., yeast, Baculovirus, and mammalian); see, e.g., Breitling et al., *Recombinant antibodies*, John Wiley & Sons, Inc. and Spektrum Akademischer Verlag, 1999. Plant cells, including transgenic plants, and animal cells, including transgenic animals (other than humans), including the nucleic acid or antibody molecules disclosed herein are also contemplated as part of the present invention. Suitable mammalian cell lines including, but not limited to, those derived from Chinese Hamster Ovary (CHO) cells, including but not limited to DHFR-CHO cells (described in Urlaub and Chasin, 1980 *Proc. Natl. Acad. Sci. USA* 77:4216-4220) used, for example, with a DHFR selectable marker (e.g., as described in Kaufman and Sharp, 1982 *Mol. Biol.* 159:601-621), NS0 myeloma cells (where a GS expression system as described in WO 87/04462, WO 89/01036, and EP 338,841 may be used), COS cells, SP2 cells, HeLa cells, baby hamster kidney cells, YB2/0 rat myeloma cells, human embryonic kidney cells, human embryonic retina cells, and others harboring the nucleic acid or antibody molecules disclosed herein form additional embodiments of the present invention. Specific embodiments of the present invention may employ *E. coli*; see, e.g., Plückthun, 1991 *Bio/Technology* 9:545-551, or yeast, such as *Pichia*, and recombinant derivatives thereof (see, e.g., Li et al., 2006 *Nat. Biotechnol.* 24:210-215). Additional specific embodiments of the present invention may employ eukaryotic cells for the production of antibody molecules, see, Chadd & Chamow, 2001 *Current Opinion in Biotechnology* 12:188-194, Andersen & Krummen, 2002 *Current Opinion in Biotechnology* 13:117, Larrick & Thomas, 2001 *Current Opinion in Biotechnology* 12:411-418. Specific embodiments of the present invention may employ mammalian cells able to produce antibody molecules with proper post-translational modifications. Post-translational modifications include, but are by no means limited to, disulfide bond formation and glycosylation. Another type of post-translational modification is signal peptide cleavage. Specific embodiments herein have the appropriate glycosylation; see, e.g., Yoo et al., 2002 *J. Immunol. Methods* 261:1-20. Naturally occurring antibodies contain at least one N-linked carbohydrate attached to a heavy chain. Id. Different types of mammalian host cells can be used to provide for efficient post-translational modifications. Examples of such host cells include Chinese Hamster Ovary (CHO), HeLa, C6, PC12, and myeloma cells; see, Yoo et al., 2002 *J. Immunol. Methods* 261:1-20, and Persic et al., 1997 *Gene* 187:9-18.

In another aspect, the present invention provides isolated cell(s) comprising a polypeptide of the present invention.

In another aspect, the present invention provides a method of making an antibody molecule of the present invention, which involves incubating a cell harboring a nucleic acid encoding a heavy and/or light chain (dictated by the desired antibody molecule) with specificity for human IL-13R$\alpha$1 under conditions that allow the expression and assembly of said heavy and/or light chains into an antibody molecule, and isolating said antibody molecule from the cell. One example by which to generate the desired heavy and/or light chain sequence is to first amplify (and modify) the germline heavy and/or light chain variable sequences using PCR. Germline sequence for human heavy and/or light variable regions are readily available to the skilled artisan, see, e.g., the "Vbase" human germline sequence database, and Kabat, E. A. et al., 1991 *Sequences of Proteins of Immunological Interest*, Fifth Edition, U.S. Department of Health and Human Services, NIH Publication No. 91-3242; Tomlinson, I. M. et al., 1992 "The Repertoire of Human Germline VH Sequences Reveals about Fifty Groups of VH Segments with Different Hypervariable Loops" *J. Mol. Biol.* 227:776-798; and Cox, J. P. L. et al., 1994 "A Directory of Human Germ-line V$\kappa$ Segments Reveals a Strong Bias in their Usage" *Eur. J. Immunol.* 24:827-836. Mutagenesis of the germline sequences may be carried out using standard methods, e.g., PCR-mediated mutagenesis where the mutations are incorporated into the PCR primers, or site-directed mutagenesis. If full-length antibodies are desired, sequence is available for the human heavy chain constant region genes; see, e.g., Kabat. E. A. et al., 1991 *Sequences of Proteins of Immunological Interest*, Fifth Edition, U.S. Department of Health and Human Services, NIH Publication No. 91-3242. Fragments containing these regions may be obtained, for example, by standard PCR amplification. Alternatively, the skilled artisan can avail him/herself of vectors already encoding heavy and/or light chain constant regions.

Available techniques exist to recombinantly produce other antibody molecules which retain the specificity of an original antibody. A specific example of this is where DNA encoding the immunoglobulin variable region or the CDRs is introduced into the constant regions, or constant regions and framework regions, of another antibody molecule; see, e.g., EP-184,187, GB 2188638, and EP-239400, and scientific literature in the area. Cloning and expression of antibody molecules, including chimeric antibodies, are described in the literature; see, e.g., EP 0120694 and EP 0125023, and other scientific literature in the area.

Additional antibodies in accordance with the present invention can be raised and then screened for the characteristics identified herein using known techniques. Basic techniques for the preparation of monoclonal antibodies are described in the literature, see, e.g., Kohler and Milstein (1975, *Nature* 256:495-497). Fully human monoclonal antibodies are produced by available methods. These methods include, but are by no means limited to, the use of genetically engineered mouse strains which possess an immune system whereby the mouse antibody genes have been inactivated and in turn replaced with a repertoire of functional human antibody genes, while leaving other components of the mouse immune system unchanged. Such genetically engineered mice allow for the natural in vivo immune response and affinity maturation process which results in high affinity, full human monoclonal antibodies. This technology is well-known in the art and is fully detailed in various publications including, but not limited to, U.S. Pat. Nos. 5,545,806; 5,569,825; 5,625,126; 5,633,425; 5,789,650; 5,877,397; 5,661,016; 5,814,318; 5,874,299; 5,770,249 (assigned to GenPharm International and available through Medarex, under the umbrella of the "UltraMab Human Antibody Development System"); as well as U.S. Pat. Nos. 5,939,598; 6,075,181; 6,114,598; 6,150,584 and related family members (assigned to Abgenix, disclosing their XENOMOUSE® technology). See also reviews from Kellerman and Green, 2002 *Curr. Opinion in Biotechnology* 13:593-597, and Kontermann & Stefan, 2001 *Antibody Engineering*, Springer Laboratory Manuals.

Alternatively, a library of antigen binding fragments in accordance with the present invention may be brought into contact with IL-13Rα1, and ones able to demonstrate binding at the prescribed level, e.g., exhibiting a $K_D$ with the antigen which is less than 200 pM and the ability to antagonize IL-13Rα1-mediated activity selected. Techniques are available to the artisan for the selection of antibody fragments from libraries using enrichment technologies including, but not limited to, phage display (e.g., see technology from Cambridge Antibody Technology (CAT) disclosed in U.S. Pat. Nos. 5,565,332; 5,733,743; 5,871,907; 5,872,215; 5,885,793; 5,962,255; 6,140,471; 6,225,447; 6,291,650; 6,492,160; 6,521,404; 6,544,731; 6,555,313; 6,582,915; 6,593,081, as well as other U.S. family members and/or applications which rely on priority filing GB 9206318, filed May 24, 1992; see also Vaughn et al., 1996, *Nature Biotechnology* 14:309-314), ribosome display (see, e.g., Hanes and Pluckthün, 1997 *Proc. Natl. Acad. Sci.* 94:4937-4942), bacterial display (see, e.g., Georgiou, et al., 1997 *Nature Biotechnology* 15:29-34) and/or yeast display (see, e.g., Kieke, et al., 1997 *Protein Engineering* 10:1303-1310). A library, for example, can be displayed on the surface of bacteriophage particles, with the nucleic acid encoding the antigen binding fragments expressed and displayed on its surface. Nucleic acids may then be isolated from bacteriophage particles exhibiting the desired level of activity and the nucleic acids used in the development of antibody molecules. Individual heavy or light chain clones in accordance with the present invention may also be used to screen for complementary heavy or light chains, respectively, capable of interaction therewith to form a molecule of the combined heavy and light chains; see, e.g., WO 92/01047. Phage display has been described in the literature; see, e.g., Kontermann & Stefan, supra, and WO 92/01047.

Monoclonal antibodies (MAbs) may be purified by techniques available to one of skill in the art. Antibody titers of the relevant ascites, hybridoma culture fluids, or test sample of interest can be determined by various serological or immunological assays which include, but are not limited to, precipitation, passive agglutination, enzyme-linked immunosorbent antibody (ELISA) techniques and radioimmunoassay (RIA) techniques.

In another aspect, the present invention provides a method for antagonizing the activity of IL-13Rα1, which involves contacting a cell expressing IL-13Rα1 with an antibody molecule disclosed herein under conditions that allow said antibody molecule to bind to IL-13Rα1. Specific embodiments of the present invention include such methods wherein the cell is a human cell.

In another aspect, the present invention provides a method for antagonizing the activity of IL-13Rα1 in a subject exhibiting a condition associated with IL-13Rα1 activity, which involves administering to the subject a therapeutically effective amount of an antibody molecule of the present invention. "Antagonizing" herein refers to the act of opposing, counteracting or curtailing one or more functions of the target, be that binding, signaling or other. Inhibition or antagonism of one or more of the IL-13Rα1 functional properties can be readily determined according to methodologies known to the art as well as those described herein. It will, furthermore, be understood that such inhibition or antagonism should effectuate a decrease in the particular activity relative to that seen in the absence of the antibody or, for example, that seen when a control antibody of irrelevant specificity is present. Preferably, an antibody molecule in accordance with the present invention antagonizes IL-13 and/or IL-4-mediated IL-13Rα1 functioning to the point that there is a decrease of at least 10%, of the measured parameter, and more preferably, a decrease of at least 20%, 30%, 40%, 50%, 60%, 70%, 80%, 90% and 95% of the measured parameter. Such inhibition/antagonism of IL-13Rα1 functioning is particularly effective in those instances where receptor functioning is contributing at least in part to a particular phenotype, disease, disorder or condition which is negatively impacting the subject.

Also contemplated are methods of using the disclosed antibody molecules in the manufacture of a medicament for treatment of an IL-13Rα1-mediated disease, disorder or condition. Thus, in another aspect, the present invention provides a pharmaceutically acceptable composition comprising an antibody molecule of the invention and a pharmaceutically acceptable carrier, excipient, diluent, stabilizer, buffer, or alternative designed to facilitate administration of the antibody molecule in the desired format and amount to the treated individual. Antibody molecules disclosed herein can be used in a method of treatment or diagnosis of a particular individual (human or primate). The method of treatment can be prophylactic or therapeutic in nature. Methods of treatment in accordance with the present invention include administering to an individual a therapeutically (or prophylactically) effective amount of an antibody molecule of the present invention. "Therapeutically effective" or "prophylactically effective" amount refers to the amount necessary at the intended dosage to achieve the desired therapeutic/prophylactic effect for the period of time desired. The desired effect may be, for example, amelioration of at least one symptom associated with the treated condition. These amounts will vary, as the skilled artisan will appreciate, according to various factors, including but not limited to the disease state, age, sex and weight of the individual, and the ability of the antibody molecule to elicit the desired effect in the individual. The response may be documented by in vitro assay, in vivo non-human animal studies, and/or further supported from clinical trials. The antibody-based pharmaceutical composition of the present invention may be formulated by any number of strategies known in the art, see, e.g., McGoff and Scher, 2000 *Solution Formulation of Proteins/Peptides*, In: McNally, E. J., ed. Protein Formulation and Delivery, New York, N.Y.: Marcel Dekker; pp. 139-158; Akers & Defilippis, 2000, *Peptides and Proteins as Parenteral Solutions*, In: Pharmaceutical Formulation Development of Peptides and Proteins, Philadelphia, Pa.: Taylor and Francis; pp. 145-177; Akers et al., 2002, *Pharm. Biotechnol.* 14:47-127. A pharmaceutically acceptable composition suitable for patient administration will contain an effective amount of the antibody molecule in a formulation which both retains biological activity while also promoting maximal stability during storage within an acceptable temperature range.

The antibody-based pharmaceutically acceptable composition may be in liquid or solid form. Any technique for production of liquid or solid formulations may be utilized. Such techniques are well within the realm of the abilities of the skilled artisan. Solid formulations may be produced by any available method including, but not limited to, lyophilization, spray drying, or drying by supercritical fluid technology. Solid formulations for oral administration may be in any form rendering the antibody molecule accessible to the patient in the prescribed amount and within the prescribed period of time. The oral formulation can take the form of a number of solid formulations including, but not limited to, a tablet, capsule, or powder. Solid formulations may alternatively be lyophilized and brought into solution prior to administration for either single or multiple dosing. Antibody compositions should generally be formulated within a biologically relevant pH range and may be buffered to maintain a proper pH range during storage. Both liquid and solid formulations generally require storage at lower temperatures (e.g., 2-8° C.) in order to retain stability for longer periods. Formulated antibody compositions, especially liquid formulations, may contain a bacteriostat to prevent or minimize proteolysis during storage, including but not limited to effective concentrations (e.g., ≤1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component. Additional components may be added to either a buffered liquid or solid antibody formulation, including but not limited to sugars as a cryoprotectant (including but not limited to polyhydroxy hydrocarbons such as sorbitol, mannitol, glycerol, and dulcitol and/or disaccharides such as sucrose, lactose, maltose, or trehalose) and, in some instances, a relevant salt (including but not limited to NaCl, KCl, or LiCl). Such antibody formulations, especially liquid formulations slated for long term storage, will rely on a useful range of total osmolarity to both promote long term stability at temperatures of, for example, 2-8° C. or higher, while also making the formulation useful for parenteral injection. As appropriate, preservatives, stabilizers, buffers, antioxidants and/or other additives may be included. The formulations may contain a divalent cation (including but not limited to $MgCl_2$, $CaCl_2$, and $MnCl_2$); and/or a non-ionic surfactant (including but not limited to Polysorbate-80 (TWEEN 80™), Polysorbate-60 (TWEEN 60™), Polysorbate-40 (TWEEN 40™), and Polysorbate-20 (TWEEN 20™), polyoxyethylene alkyl ethers, including but not limited to BRIJ 58™, BRIJ 35™, as well as others such as TRITON X-100™, TRITON X-114™, NP40™, Span 85 and the PLURONIC® series of non-ionic surfactants (e.g., PLURONIC® 121). Any combination of such components form specific embodiments of the present invention.

Pharmaceutical compositions in liquid format may include a liquid carrier, e.g., water, petroleum, animal oil, vegetable oil, mineral oil, or synthetic oil. The liquid format may also include physiological saline solution, dextrose or other saccharide solution or glycols, such as ethylene glycol, propylene glycol or polyethylene glycol.

The pharmaceutical composition may be in the form of a parenterally acceptable aqueous solution that is pyrogen-free with suitable pH, tonicity, and stability. Pharmaceutical compositions may be formulated for administration after dilution in isotonic vehicles, for example, Sodium Chloride Injection, Ringer's Injection, or Lactated Ringer's Injection.

Dosing of antibody therapeutics is well within the realm of the skilled artisan, see, e.g., Lederman et al., 1991 *Int. J. Cancer* 47:659-664; Bagshawe et al., 1991 *Antibody, Immunoconjugates and Radiopharmaceuticals* 4:915-922, and will vary based on a number of factors including but not limited to the antibody molecule utilized, the patient being treated, the condition of the patient, the area being treated, the route of administration, and the treatment desired. A physician or veterinarian of ordinary skill can readily determine and prescribe the effective therapeutic amount of the antibody. Dosage ranges may be from about 0.01 to 100 mg/kg, and more usually 0.05 to 25 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. For purposes of illustration, and not limitation, in specific embodiments, a dose of 5 mg to 2.0 g may be utilized to deliver the antibody molecule systemically. Optimal precision in achieving concentrations of antibody within a range that yields efficacy without toxicity requires a regimen based on the kinetics of the drug's availability to the target site(s). This involves a consideration of the distribution, equilibrium, and elimination of the antibody molecule. Antibodies described herein may be used alone at appropriate dosages. Alternatively, co-administration or sequential administration of other agents may be desirable. It will be possible to present a therapeutic dosing regime for the antibody molecules of the present invention in conjunction with alternative treatment regimes. Individuals (subjects) capable of treatment include primates, human and non-human, and include any non-human mammal or vertebrate of commercial or domestic veterinary importance.

The antibody molecule could be administered to an individual by any route of administration appreciated in the art, including but not limited to oral administration, administration by injection (specific embodiments of which include intravenous, subcutaneous, intraperitoneal or intramuscular injection), administration by inhalation, intranasal, or topical administration, either alone or in combination with other agents designed to assist in the treatment of the individual. The route of administration should be determined based on a number of considerations appreciated by the skilled artisan including, but not limited to, the desired physiochemical characteristics of the treatment. Treatment may be provided on a daily, weekly, biweekly, or monthly basis, or any other regimen that delivers the appropriate amount of antibody molecule to the individual at the prescribed times such that the desired treatment is effected and maintained. The formulations may be administered in a single dose or in more than one dose at separate times.

In particular embodiments, the condition treated is selected from the group consisting of asthma, allergy, allergic rhinitis, chronic sinusitis, hay fever, atopic dermatitis, chronic obstructive pulmonary disease (COPD), pulmonary fibrosis, esophageal eosinophilia, psoriasis, psoriatic arthritis, fibrosis, scleroderma, inflammatory bowel disease (particularly, ulcerative colitis), anaphylaxis, and cancer (particularly, Hodgkin's lymphoma, glioma, and renal carcinoma), and general Th2-mediated disorders/conditions.

The present invention further provides for the administration of the disclosed anti-hIL-13Rα1 antibody molecules for purposes of gene therapy. In such a method, the cells of a subject would be transformed with nucleic acid encoding the antibody molecules of the invention. Subjects comprising the nucleic acids will then produce the antibody molecules endogenously. Previously, Alvarez, et al, *Clinical Cancer Research* 6:3081-3087, 2000, introduced single-chain anti-ErbB2 antibodies to subjects using a gene therapy approach. The methods disclosed by Alvarez, et al, may be easily adapted for the introduction of nucleic acids encoding an anti-hIL-13Rα1 antibody of the invention to a subject.

Nucleic acids encoding any polypeptide or antibody molecule of the invention may be introduced to a subject. In specific embodiments, the antibody molecule is a human, single-chain antibody.

The nucleic acids may be introduced to the cells of a subject by any means known in the art. In specific embodiments, the nucleic acids are introduced as part of a viral vector. Examples of particular viruses from which the vectors may be derived include lentiviruses, herpes viruses, adenoviruses, adeno-associated viruses, vaccinia virus, baculovirus, alphavirus, influenza virus, and other recombinant viruses with desirable cellular tropism.

Various companies produce viral vectors commercially, including, but by no means limited to, AVIGEN, Inc. (Alameda, Calif.; AAV vectors), Cell Genesys (Foster City, Calif.; retroviral, adenoviral, AAV vectors, and lentiviral vectors), CLONTECH (retroviral and baculoviral vectors), Genovo, Inc. (Sharon Hill, Pa.; adenoviral and AAV vectors), GENVEC (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Methods for constructing and using viral vectors are known in the art (see, e.g., Miller, et al, *BioTechniques* 7:980-990, 1992). In specific embodiments, the viral vectors are replication defective, that is, they are unable to replicate autonomously, and thus are not infectious, in the target cell. The replication defective virus may be a minimal virus, i.e., it retains only the sequences of its genome which are necessary for encapsidating the genome to produce viral particles. Defective viruses which entirely or almost entirely lack viral genes may be used as well. Use of defective viral vectors allows for administration to cells in a specific, localized area, without concern that the vector can infect other cells. Thus, a specific tissue can be specifically targeted.

Examples of vectors comprising attenuated or defective DNA virus sequences include, but are not limited to, a defective herpes virus vector (Kanno et al, *Cancer Gen. Ther.* 6:147-154, 1999; Kaplitt et al, *J. Neurosci. Meth.* 71:125-132, 1997 and Kaplitt et al, *J. Neuro One.* 19:137-147, 1994).

Adenoviruses are eukaryotic DNA viruses that can be modified to efficiently deliver a nucleic acid of the invention to a variety of cell types. Attenuated adenovirus vectors, such as the vector described by Strafford-Perricaudet et al, *J. Clin. Invest.* 90:626-630, 1992 are desirable in some instances. Various replication defective adenovirus and minimum adenovirus vectors have been described (see, e.g., WO94/26914, WO94/28938, WO94/28152, WO94/12649, WO95/02697 and WO96/22378). The replication defective recombinant adenoviruses according to the invention can be prepared by any technique known to a person skilled in the art (Levrero et al, *Gene* 101:195, 1991; EP 185573; Graham, *EMBO J.* 3:2917, 1984; Graham et al, *J. Gen. Virol.* 36:59, 1977).

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The use of vectors derived from the AAVs for transferring genes in vitro and in vivo has been described (see Daly, et al, *Gene Ther.* 8:1343-1346, 2001, Larson et al, *Adv. Exp. Med. Bio.* 489:45-57, 2001; WO 91/18088 and WO 93/09239; U.S. Pat. Nos. 4,797,368 and 5,139,941 and EP 488528B1).

In another embodiment, the gene can be introduced in a retroviral vector, e.g., as described in U.S. Pat. Nos. 5,399,346, 4,650,764, 4,980,289, and 5,124,263; Mann et al, *Cell* 33:153, 1983; Markowitz et al, *J. Virol.,* 62:1120, 1988; EP 453242 and EP178220. The retroviruses are integrating viruses which infect dividing cells.

Lentiviral vectors can be used as agents for the direct delivery and sustained expression of nucleic acids encoding an antibody molecule of the invention in several tissue types, including brain, retina, muscle, liver and blood. The vectors can efficiently transduce dividing and nondividing cells in these tissues, and maintain long-term expression of the antibody molecule. For a review, see Zufferey et al, *J. Virol.* 72:9873-80, 1998 and Kafri et al, *Curr. Opin. Mol. Ther.* 3:316-326, 2001. Lentiviral packaging cell lines are available and known generally in the art. They facilitate the production of high-titer lentivirus vectors for gene therapy. An example is a tetracycline-inducible VSV-G pseudotyped lentivirus packaging cell line which can generate virus particles at titers greater than $10^6$ IU/ml for at least 3 to 4 days; see Kafri et al, *J. Virol.* 73:576-584, 1999. The vector produced by the inducible cell line can be concentrated as needed for efficiently transducing nondividing cells in vitro and in vivo.

Sindbis virus is a member of the alphavirus genus and has been studied extensively since its discovery in various parts of the world beginning in 1953. Gene transduction based on alphavirus, particularly Sindbis virus, has been well-studied in vitro (see Straus et al, *Microbiol. Rev.,* 58:491-562, 1994; Bredenbeek et al, *J. Virol.,* 67:6439-6446, 1993; Ijima et al, *Int. J. Cancer* 80:110-118, 1999 and Sawai et al, *Biochim. Biophyr. Res. Comm.* 248:315-323, 1998. Many properties of alphavirus vectors make them a desirable alternative to other virus-derived vector systems being developed, including rapid engineering of expression constructs, production of high-titered stocks of infectious particles, infection of nondividing cells, and high levels of expression (Strauss et al, 1994 supra). Use of Sindbis virus for gene therapy has been described. (Wahlfors et al, *Gene. Ther.* 7:472-480, 2000 and Lundstrom, *J. Recep. Sig. Transduct. Res.* 19(1-4):673-686, 1999.

In another embodiment, a vector can be introduced to cells by lipofection or with other transfection facilitating agents (peptides, polymers, etc.). Synthetic cationic lipids can be used to prepare liposomes for in vivo and in vitro transfection of a gene encoding a marker (Feigner et al, *Proc. Natl. Acad. Sci. USA* 84:7413-7417, 1987 and Wang et al, *Proc. Natl. Acad. Sci. USA* 84:7851-7855, 1987). Useful lipid compounds and compositions for transfer of nucleic acids are described in WO 95/18863 and WO 96/17823, and in U.S. Pat. No. 5,459,127.

It is also possible to introduce the vector in vivo as a naked DNA plasmid. Naked DNA vectors for gene therapy can be introduced into the desired host cells by methods known in the art, e.g., electroporation, microinjection, cell fusion, DEAE-dextran, calcium phosphate precipitation, use of a gene gun, or use of a DNA vector transporter (see, e.g., Wilson, et al, *J. Biol. Chem.* 267:963-967, 1992; Williams et al, *Proc. Natl. Acad. Sci. USA* 88:2726-2730, 1991). Receptor-mediated DNA delivery approaches can also be used (Wu et al, *J. Biol. Chem.* 263:14621-14624, 1988). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Vilquin et al, *Gene Ther.* 8:1097, 2001; Payen et al, *Exp. Hematol.* 29:295-300, 2001; Mir, *Bioelectrochemistry* 53:1-10, 2001; WO 99/01157, WO 99/01158 and WO 99/01175).

Pharmaceutical compositions suitable for such gene therapy approaches and comprising nucleic acids encoding an anti-hIL-13Rα1 antibody molecule of the present invention are included within the scope of the present invention.

In another aspect, the present invention provides a method for identifying, isolating, quantifying or antagonizing IL-13Rα1 in a sample of interest using an antibody molecule of the present invention. The antibody molecules may be utilized as a research tool in immunochemical assays, such as western blots, ELISAs, radioimmunoassay, immunohistochemical assays, immunoprecipitations, or other immunochemical assays known in the art (see, e.g., Immunological Techniques Laboratory Manual, ed. Goers, J. 1993, Academic Press) or various purification protocols. The antibody molecules may have a label to facilitate ready identification or measurement of the activities associated therewith. One skilled in the art is readily familiar with the various types of detectable labels (e.g., enzymes, dyes, or other suitable molecules which are either readily detectable or cause some activity/result that is readily detectable) useful in the above protocols.

Additional aspects of the present invention are kits including the antibody molecules or pharmaceutical compositions disclosed herein and instructions for use. Kits typically but need not include a label indicating the intended use of the contents of the kit. The term label includes any writing, or recorded material supplied on or with the kit, or which otherwise accompanies the kit.

Related to yet another aspect of the present invention, a critical contact point between the antibodies disclosed herein and the hIL-13Rα1 receptor was identified. This critical contact point was identified by introducing a specific mutation that impacted the binding of the receptor by the antibody. More specifically, it was found that substitution of the phenylalanine residue at position 233 of SEQ ID NO:101 with an alanine residue results in a loss of binding between the antibody and the mutant receptor compared with the binding between the antibody and wild type receptor. This is a very useful finding in characterizing 10G5 and its derivatives. Peptides exploiting the region surrounding amino acid 233 will be useful in the generation of additional monoclonal antibodies with similar specificity. Accordingly, the present invention encompasses isolated peptides including a hIL-13R sequence with a Phe233Ala mutation (i.e. SEQ ID NO:120), whether they be full-length or fragments thereof (e.g., 5 to 350 amino acid residue fragments) including the mutation. Additionally, the present invention also encompasses the use of said peptides in an assay to evaluate 10G5 or 10G5 derivatives, identify antibodies with specificity for a similar epitope or, alternatively, produce antibodies with similar specificity. In specific embodiments the present invention, therefore, provides a method of screening for antibody molecules that target the same region on hIL-13Rα1 as the antibody produced by the hybridoma cell line deposited as ATCC Deposit No. PTA-6933, which involves (a) analyzing binding of an antibody molecule of interest to (i) an isolated hIL-13Rα1 polypeptide of SEQ ID NO:101 or fragment thereof including the amino acid corresponding to residue 233 of SEQ ID NO:101; and (ii) an isolated polypeptide or fragment of an isolated hIL-13Rα1 polypeptide or fragment thereof wherein the amino acid corresponding to residue 233 of SEQ ID NO:101 is an alanine rather than a phenylalanine; (b) identifying those antibodies that bind to the isolated polypeptide or fragment of step (a)(i) but exhibit significantly reduced binding to the isolated polypeptide or fragment of step (a) (ii); and (c) recovering the antibodies identified in step (b). A significant decrease is typically more than a 10-fold reduction in binding between an antibody and the mutant receptor compared with the binding between the antibody and wild type receptor. Polypeptides that are useful in the method are those fragments of SEQ ID NO:101 including the amino acid corresponding to residue 233 of SEQ ID NO:101 that bind to the antibody produced by the hybridoma cell line deposited as ATCC Deposit No. PTA-6933, and the corresponding fragments wherein the amino acid corresponding to residue 233 of SEQ ID NO:101 is an alanine rather than a phenylalanine. For example, the extracellular region of human IL-13Rα1 (amino acids number 1 to 317 of SEQ ID NO:101) may be used along with its corresponding Phe233Ala mutant.

Another aspect of the invention includes an isolated antibody that (i) competes with the antibody produced by the hybridoma cell line deposited as ATCC Deposit No. PTA-6933 for binding to hIL-13Rα1; (ii) inhibits IL-13 signaling; and (iii) wherein a substitution in a hIL-13Rα1 peptide of the phenylalanine residue that corresponds to position 233 of SEQ ID NO:101 with an alanine residue leads to a loss of binding between said antibody and the resultant mutant hIL-13Rα1 peptide compared to the binding between said antibody and the hIL-13Rα1 peptide without said substitution.

The invention is described in greater detail by the following non-limiting examples.

Example 1

Production and Purification of a Recombinant Protein Based on the Human IL-13Rα1 Extracellular Region Using the protocol described herein, an N-terminal FLAG®-tagged fusion protein including most of the extracellular region of human IL-13Rα1 (amino acids number 3 to 317 of SEQ ID NO:101) was purified from culture media conditioned by a stably transfected (pEFBOS-S-FLAG® vector encoding IL-13Rα1.ECR) CHO cell clone. The purified hIL-13Rα1.ECR protein (SEQ ID NO:103) was concentrated and subsequently desalted into phosphate-buffered saline (PBS), 0.02% v/v TWEEN™ 20, followed by filter sterilization. Typical recovery was 0.4 mg protein per liter of conditioned media. Protein was stored at −80° C. until required.

Methods.

A pEFBOS-S-FLAG® expression vector incorporating a cDNA encoding the extracellular region (ECR) of human IL-13Rα1 with an IL-3 signal sequence and FLAG®-tag fusion was transfected into CHO cells for stable expression using standard procedures. CHO-derived conditioned media was then concentrated 10-fold by ultrafiltration using a 10 kDa cut-off membrane. Concentrated media was applied to an M2 (anti-FLAG®) affinity chromatography column and eluted with FLAG® peptide at a concentration of 100 µg/ml. The eluate was concentrated by lyophilization and then buffer exchanged into Tris pH 8.0 using GF50 SEPHAROSE™ resin packed into column (2.6 cm×40 cm). The buffer exchanged fraction was then subjected to anion exchange chromatography using a MONO™ Q 5/5 column. A proteolysed fragment of IL-13Rα1 was strongly retained and was separated from the full-length IL-13Rα1 which eluted at a lower salt concentration. Pooled fractions and filter sterilized final product was assessed by SDS-PAGE and western blot analysis. The sample was then quantitated using UV absorbance, where 1 absorbance unit was approximately 1 mg/ml.

Example 2

Generation of Hybridoma Cell Lines Producing Human Anti-Human IL-13Rα1 Monoclonal Antibodies Immunization of Transgenic Mice.

Male and female transgenic mice from the HCo7, HCo12 and HCo7×HCo12 strains (HUMAB™ mice, Medarex, USA) were immunized with hIL-13Rα1.ECR of Example 1. For the first immunization, 20-50 µg of hIL-13Rα1.ECR was emulsified in Complete Freund's Adjuvant (CFA) and administered via the intraperitoneal (i.p.) route. For a minimum of two and a maximum of three subsequent i.p. immunizations, 20-50 µg of hIL-13Rα1.ECR was emulsified in Incomplete Freund's Adjuvant (IFA). Following the second or third immunization with hIL-13Rα1.ECR in IFA, serum was sampled (retro-orbital plexus) and assayed for human antibodies against the hIL-13Rα1.ECR by ELISA as described herein. High-responder mice (serum titers generally >1:3200) were selected for hybridoma generation. In some cases, animals not used for hybridoma generation at this point received further i.p. immunizations with 20-50 µg of hIL-13Rα1.ECR in PBS. Serum from these animals was again assayed for human antibodies against the hIL-13Rα1.ECR by ELISA and high-responder mice were used for hybridoma generation. Mice selected for hybridoma generation were boosted intravenously with 20-50 µg of hIL-13Rα1.ECR 3-4 days prior to spleen cell fusion.

Antigen-Specific ELISA.

Mouse serum or hybridoma culture supernatant fluid (SNF) was assessed for mAbs able to bind to plate bound hIL-13Rα1.ECR using a standard ELISA format as follows. Flat bottom 96-well MAXISORP™ plates (NUNC, Invitro Technologies, #439454) were coated with 50 µl of a solution containing 2.5 µg/ml hIL-13Rα1.ECR diluted in PBS and incubated overnight at 4° C. After washing two times with PBS, plates were blocked with 2% w/v skim milk in PBS (blocking buffer, 200 µl/well) for 1 hour at 37° C., then washed a further two times with PBS containing 0.1% v/v TWEEN™ 20 (wash buffer). Fifty µl of test hybridoma SNF or mouse serum was added per well and plates were incubated at room temperature for 1 hour. Plates were washed three times. Bound human mAbs were detected using an anti-human IgG HRP-conjugated secondary reagent diluted 1:1000 in PBS containing 1% w/v skim milk powder and 0.1% v/v TWEEN™ 20. Fifty µl/well of the anti-human IgG HRP-conjugated secondary reagent was added to the plates for 1 hour at room temperature. The plates were then washed three times, developed with TMB substrate, and OD read at 450 nm.

Hybridoma Generation.

Selected high-responder mice were sacrificed and the spleen and relevant lymph nodes were collected. The fusion of spleen and lymph node cells with the fusion partner SP2/0 and subsequent HAT (hypoxanthine/aminopterin/thymidine) (GIBCO-BRL, #21060-017) selection of hybridomas were performed according to standard procedures (*Antibodies: A Laboratory Manual*, Harlow and Lane, Cold Spring Harbor Laboratory Press). Briefly, the centrifuge was adjusted to room temperature, with a water bath to 37° C. and a heat block to 37° C. Polyethylene glycol (PEG) was warmed to 37° C. Medium was prepared for culturing cells after the fusion was completed. The medium included hybridoma serum-free medium (HSFM) (GIBCO-BRL, #12045-084), 5% Ultra low IgG FBS (FBS) (GIBCO-BRL, #16250-078), 2 mM Glutamax-1 (GIBCO-BRL, #35050-061), 50 U/50 µg/ml Penicillin/Streptomycin (GIBCO-BRL, #15070-063) and 1×HAT. Media was warmed to 37° C. SP2/O cells were harvested and a viable cell count was performed. The cells were healthy, actively dividing and in log-phase. The viability was >95%. SP2/Os were cultured in HSFM/5% Ultra low IgG FBS prior to fusion, and split 1:2 or 1:3 on the day before the fusion. On the day of fusion, the animals were sacrificed and the spleen (and lymph nodes if required) were immediately removed into sterile medium (Dulbecco's modification of Eagles media (GIBCO-BRL, #11995-073) or DME) on ice. A single-cell suspension was prepared from the spleen, and washed twice (1800 rpm for 7 minutes) in DME, the second wash warm. The SP2/O cells were washed three times (1500 rpm, 7 minutes) with warm DME to remove all traces of serum. SP2/O cells ($10^8$) were used for one mouse spleen, done as two separate fusions. SP2/Os and spleen cells were pooled together in the same tube and centrifuged at 2100 rpm (400 g) for 5 minutes. All DME was removed, leaving only combined pellet. The DME was placed in 37° C. heat block. One ml of warm PEG was added drop-wise to the cell pellet over 1 minute whilst stirring the pellet gently with the pipette. Stirring continued gently for another minute. One ml warm DME was added, drop-wise, stirring, over 1 minute. Another 1 ml DME was added over 1 minute. Then 20 ml DME was added over 5 minutes while stirring slowly. This was then centrifuged for 5 minutes at 1500 rpm. All supernatant was removed, and cells were resuspended gently in culture medium as above. One mouse spleen was plated to 5 microtiter plates at 0.2 ml per well in HAT medium. The plates were fed by removing approximately 0.1 ml from each well and replacing with fresh HAT medium every 3 or 4 days. Wells were checked for growth of hybridomas at day 7-10 (routine screening 10-14 days after the fusion). Being sure that the medium had not been changed for at least 2-3 days beforehand, ~100 µl of supernatant was removed from each well for assay. Positives were transferred to 1 ml or 2 ml wells then gradually expanded to 6-well plates. Hybridomas were not clonal at this stage. After 14 days in HAT medium, hybridomas were cultured in HT (GIBCO-BLR, #11067-030) (HSFM, 5% Ultralow IgGFBS, 10 ng/ml rhIL-6 (R&D Systems, #206-IL-050) and HT) for approximately 2 more weeks, then without HT.

Culture of Hybridomas.

Hybridomas testing positive at primary and follow-up confirmation ELISA screens were cloned by limit dilution. Limit dilution wells containing single colonies were screened by ELISA and a positive well was selected for expansion. Further rounds of limit dilution cloning were carried out until 100% of wells test positive.

For production of supernatant fluid (SNF) for antibody purification, hybridomas were expanded into either T175 $cm^2$ flasks (Falcon, #3028) or roller bottles (900 $cm^2$) (CORNING, #430849). Media used for generation of hybridoma SNFs was HSFM supplemented with 5% Ultralow IgG FBS, 2 mM glutamine and 50 U/50 µg/ml penicillin/streptomycin. Hybridomas were allowed to grow to confluence and media was harvested by centrifugation approximately 5-10 days later when >90% of cells were dead. All conditioned media was filtered using a STERICUP™ filter apparatus (MILLIPORE, #SCGPU11RE) (0.45 µm) prior to mAb purification.

Production of Purified mAbs.

Monoclonal antibodies were purified from SNF using a standard Protein A affinity chromatography based strategy; see e.g., the following apparatus and reagents. HPLC: AKTA explorer (AMERSHAM Biosciences, Sweden); Column: Protein A (HITRAP™, 1 ml, Amersham Biosciences, Sweden); Buffer A: PBS, 0.02% TWEEN™ 20; Buffer B: 0.1 M Glycine pH 2.8; and Buffer C: 2 M Tris pH 8.0.

The column was prepared by washing with 5 volumes of buffer A. Conditioned media was loaded onto dedicated column. A wash was performed with 100 volumes of buffer A, and elution with 20 ml (10×2 ml) of buffer B. Collection was into tube containing 0.2 ml of buffer C. Column was washed with buffer A to store at 4° C. Desalting was performed using 10K cut-off dialysis membrane into PBS, 0.02% TWEEN™ 20. mAb purity was demonstrated by SDS-PAGE with COOMASSIE® Blue staining.

Antibody was quantitated by spectrophotometric analysis at 280 nm using an immunoglobulin extinction coefficient of 1.0 absorbance unit being equivalent to 1.34 mg/ml of antibody.

Example 3

Analysis of Anti-Human IL-13Rα1 Monoclonal Antibody 10G5 Affinity for Human IL-13Rα1

BIACORE™-Based Studies.

Human IL-13Rα1.ECR (40 µg/ml in 20 mM Sodium Acetate, pH 4.2) of Example 1 was immobilized to a sensorchip (CM5, Biosensor, Sweden) using standard NHS/EDC chemistry according to the manufacturer's instructions at a set immobilization value, for example, 1000 RU. Ethanolamine (1.0 M), pH 8.0 was used to quench residual active esters post hIL-13Rα1.ECR immobilization.

Analysis of binding of 10G5 (concentration range of 1.4 nM to 150 nM, two-fold dilutions) to the immobilized hIL-13Rα1.ECR was performed in duplicate. Sensorgrams generated were fitted to a bivalent ligand binding model to simultaneously derive association ($k_a$) and dissociation ($k_d$) rates and used to determine binding affinity ($K_D$, Biaevaluation software, BIACORE™, Sweden).

The binding affinity ($K_D$) of anti-IL-13Rα1 human mAb 10G5 was ~254 pM (n=8).

Example 4

Analysis of the Binding of Anti-Human IL-13Rα1 Monoclonal Antibody 10G5 to Cynomolgus Macaque and Mouse IL-13Rα1

A cDNA encoding the cynomolgus macaque IL-13Rα1 (cyIL-13Rα1) was cloned by PCR using mRNA extracted from cynomolgus spleen and bone marrow. The mature sequence was highly conserved between cynomolgus and human IL-13Rα1 with an amino acid identity of about 97% (see GENBANK accession No. AAP78901).

For production of purified cynomolgus IL-13Rα1.ECR protein, a cDNA encoding cynomolgus IL-13Rα1.ECR (amino acids 9 to 325 of GENBANK accession No. AAP78901 or amino acids 1 to 317 of SEQ ID NO:104) was cloned into the pEFBOS-S-FLAG® vector for expression as an N-terminal FLAG®-tagged fusion protein essentially as described above for the hIL-13Rα1.ECR.

Mouse IL-13Rα1.ECR (amino acids 27 to 344 of GENBANK accession No. O09030 or amino acids 1 to 318 of SEQ ID NO:105) was also expressed and purified as an N-terminal FLAG®-tagged fusion (mIL-13Rα1.ECR) essentially as described above.

The potential cross-reactivity of mAb 10G5 with mouse and cynomolgus IL-13Rα1.ECR was assessed using a BIACORE™-based approach. Purified mouse, human and cynomolgus IL-13Rα1.ECR were immobilized individually to three channels of a sensorchip (CMS, BIACORE™, Sweden) using standard immobilization chemistry. Monoclonal antibodies (concentration range of 312.5 nM down to 125 pM) were assessed for binding to the receptors simultaneously at a flow rate of 15 µl/minute. Analysis of the affinity of the mAb was performed as described in Example 3 above.

The results of this analysis indicated that MAb 10G5 showed a 10-fold lower affinity (~2.9 nM) for the cynomolgus receptor compared with the human receptor (~254 pM), and negligible binding to mouse receptor.

Example 5

Analysis of the Ability of 10G5 to Compete with IL-13 for Binding of Human IL-13Rα1

The ability of 10G5 to compete with IL-13 for binding to IL-13Rα1 was assessed by a competition assay on a BIACORE™ instrument. A sensorchip was prepared by immobilizing human IL-13 using standard NHS/EDC chemistry as per the manufacturer's instructions. hIL-13Rα1.ECR protein (8 µg/mL) was incubated with excess mAb (50 µg/mL) for 2 hours at room temperature, then injected over the sensorchip. The level of hIL-13Rα1.ECR protein bound to immobilized IL-13 was recorded at a fixed time point within the sensorgram and divided by the corresponding level of hIL-13Rα1.ECR protein bound in the absence of mAb ("relative IL-13 binding"). Binding ratios <1 were indicative of competition between mAb and IL-13 for binding to IL-13Rα1, while values 1 indicated the mAb bound to IL-13Rα1 at a site distinct from that binding IL-13.

mAb 10G5 was found to inhibit binding of the hIL-13Rα1.ECR protein to immobilized IL-13.

Example 6

Analysis of the Ability of Anti-Human IL-13Rα1 Monoclonal Antibodies to Antagonize IL-13- and IL-4-Mediated Cellular Responses Normal Human Dermal Fibroblast (NHDF) Eotaxin Assay.

NHDF cells have been demonstrated to produce eotaxin in response to IL-13 and mAbs directed against the IL-13Rα1 may inhibit this response. Furthermore, NHDF cells were demonstrated not to express the γc receptor, thus enabling an analysis of the ability of mAbs to inhibit IL-4 activity mediated through the IL-4 Type II receptor, i.e., IL-4Rα plus IL-13Rα1. Due to species cross-reactivity, both human and non-human primate (e.g., rhesus) IL-13 can be used to stimulate eotaxin production.

NHDF cells (Cambrex, #CC-2509) were cultured in FGM media (Cambrex, #CC3132) supplemented with the recommended additives according to the manufacturer's instructions (complete media). Cells were passaged 1:3 or 1:5 once a week and monitored for responsiveness to IL-13 prior to use. To assess antagonist activity of hIL-13Rα1 specific mAbs, cells were resuspended to $2\times10^6$/ml in complete media containing 20 ng/ml PMA (SIGMA, #P8139) and 20 µg/ml polymyxin (SIGMA, #P4932) and plated in 96-well flat bottom plates (COSTAR, #3595) at $1\times10^5$ cells/well. Antibody titrations were added to the cells and incubated for 30 minutes, at 37° C. with 5% $CO_2$ in humidified air. Recombinant IL-13 (human or non-human primate) was then added to plates at a final concentration of 30 ng/ml and incubated overnight at 37° C. with 5% $CO_2$ in humidified air. Supernatants were then removed and assayed for eotaxin content by ELISA. For IL-4-induced assays, recombinant IL-4 (PHARMINGEN) was added to plates at a final concentration of 0.5 ng/ml in place of IL-13.

Eotaxin ELISA Protocol.

IMMULON®-4 plates (DYNATECH, #3855) were coated with 4 µg/ml mouse anti-human eotaxin antibody (R&D Systems, MAB320) in PBS (INVITROGEN, #14190-144), overnight at 4° C. Plates were blocked (200 µl/well, TBS supplemented with 1% BSA and 0.05% TWEEN™ 20) for 1 hour at room temperature and washed three times (wash buffer, TBS plus 0.05% TWEEN™ 20). Test SNF's from the NHDF cells were added at 50 µl/well and plates were incubated for 2 hours at room temperature, then washed three times. Biotinylated anti-human eotaxin antibody (R&D Systems, BAF320) was added at 200 ng/ml in blocking buffer (60 ml/well) and incubated for 1 hour at room temperature, then washed three times. Streptavidin-Europium (Wallac, #1244-360) was added at 100 ng/ml in europium buffer (100 µl/well) and incubated for 20 minutes at room temperature, then washed three times. Enhancement solution (Wallac, #12244-105) was added, 150 µl/well, and incubated 1 hour at room temp. Time delayed fluorescence was read using a VICTOR (PERKIN-ELMER) plate reader.

Recombinant human eotaxin (R&D Systems, #320-EO) was used to establish a standard curve. The results of this analysis indicated that the $EC_{50}$ of 10G5 against IL-13 was 0.25 µg/ml, whereas the $EC_{50}$ against IL-4 was 2.7 µg/ml.

NHDF IL-13/IL-4-Induced STAT6 Phosphorylation Assay. The phosphorylation of STAT6 (pSTAT6) is an essential element of IL-13/IL-4 signal transduction and occurs within minutes of receptor dimerization. IL-13Rα1-specific mAbs may block the phosphorylation of STAT6 in response to IL-13 and/or IL-4.

To determine this, $2×10^6$ NHDF cells in 50 µl of RPMI media (#22400-071, INVITROGEN) were plated into 96-well V bottom polypropylene PCR plates (USA Scientific, #1442-9596). Anti-IL-13R mAbs were added to the required concentration in 25 µl and plates were incubated for 30 minutes at 4° C. Recombinant hIL-13 (100 ng/ml) or hIL-4 (PHARMINGEN, 0.5 ng/ml) was added in 25 µl and plates were warmed to 37° C. in a PCR machine for 20 minutes. After 20 minutes an equal volume of 2× lysis buffer (100 mM HEPES, 200 mM NaCl, 2% v/v TRITON® X100, 100 mM NaF, 10 mM DTT, protease inhibitors) was added and pSTAT6 was measured by ELISA.

STAT6 ELISA Protocol.

IMMULON®-4 plates (DYNATECH, #3855) were coated with anti-human phospho STAT6 (BD Transduction Labs, #621995) at 10 µg/ml in PBS (INVITROGEN, #14290-144) (50 µl/well) and incubated overnight at 4° C. Plates were blocked (200 µl/well, TBS supplemented with 1% BSA and 0.05% TWEEN™ 20) for 1 hour at room temperature and washed three times (wash buffer, TBS plus 0.05% v/v TWEEN™ 20). Test lysates were added at 50 µl/well and plates were incubated for 2 hours at room temperature, then washed three times. Biotin anti-STAT6 (BD Transduction Labs, #621141, conjugated to biotin, 20:1 molar ratio) was added at 2 µg/ml in blocking buffer (60 µl/well) and incubated for 1 hour at room temperature, then washed three times. Streptavidin-Europium (Wallac, #1244-360) was added at 100 ng/ml in europium buffer (100 µl/well) and incubated for 20 minutes at room temperature, then washed three times. Enhancement solution (Wallac, #12244-105) was added (150 µl/well) and incubated 1 hour at room temperature. Time-delayed fluorescence was read using a VICTOR (PERKIN-ELMER) plate reader.

The results of this analysis indicated that the $EC_{50}$ of 10G5 was 1.0 µg/ml against IL-13, whereas the $EC_{50}$ against IL-4 was 1.3 µg/ml.

Example 7

Cloning and Sequencing of the 10G5 Murine Antibody Variable Regions

Messenger RNA was prepared from hybridoma cells producing antibody 10G5 and reverse-transcribed using an oligo-dT primer to produce cDNA. Several independent PCR reactions were performed. The PCR reactions were performed at the following conditions: 94° C. for 2 minutes; 30 cycles of 94° C. for 30 seconds, 60° C. for 30 seconds and 68° C. for 1 minute; and 68° C. for 10 minutes. Two alternative PCR conditions were also developed in cloning antibody genes: 1) 94° C. for 2 minutes; 30 cycles of 94° C. for 30 seconds, 68° C. for 30 seconds, and 68° C. for 1 minute; and 68° C. for 10 minute; and 2) 30 cycles of 94° C. for 1 minute, 55° C. for 1 minute, and 72° C. for 1 minute. PCR amplicons were separated on 1.2% agarose gels. In terms of the heavy chain variable region, the following primer sets yielded a PCR product. For the 5' end of the heavy chain variable region, the primers were VH5,5'-G GGG TCA ACC GCC ATC CTY G-3' (SEQ ID NO:114), wherein Y was C or T (Degen 2); and VH6,5'-GTC TCC TTC CTC ATC TTC CTG CCC-3' (SEQ ID NO:115) (Degen 1); while the primer for the 3' end of $V_H$ was HA, 5'-CCCA TCG GTC TTC CCC CTG GCA C-3' (SEQ ID NO:116). In terms of the light chain variable region, four primer sets yielded a PCR product. The PCR products were cloned in plasmid TOPO® pCK2.1 (INVITROGEN). Sequence analysis of the heavy chain clone had the best match to germline, VH5-51. For the light chain variable region, the primers for the 5' end that yielded a sequence with the best match to germline, VL VKIII A27, were VK3,5'-YTC TTC CTC CTG CTA CTC TGG CTC-3' (SEQ ID NO:117), wherein Y was C/T (Degen 2); and VK4, 5'-ATG GTG TTG CAG ACC CAG GTC TTC-3' (SEQ ID NO:118) (Degen 1); while the primer for the 3' end of $V_L$ was KA, 5'-G AAA TCT GGA ACT GCC TCT GTT GTG TGC CTG C-3' (SEQ ID NO:119).

The initially identified nucleotide and amino acid sequences containing the heavy and light chain variable regions of 10G5 included both leader and some additional downstream sequence (see, SEQ ID NOs:42 and 44 for the heavy chain, and SEQ ID NOs:46 and 48 for the light chain). The nucleotide and amino acid sequences of the heavy chain variable region of 10G5 are shown in FIG. 1 and in SEQ ID NOs:43 and 45, respectively. The nucleotide and amino acid sequences of the light chain variable region of 10G5 are shown in FIG. 2 and in SEQ ID NOs:47 and 49, respectively.

Example 8

Analysis of mAb Binding to Phage Displayed Human IL-13Rα1 Peptides

Mutation of the phenylalanine at position 233 of the amino acid sequence of human IL-13Rα1 extracellular region to alanine effected a significant decrease in binding of antibody 10G5 as compared to binding of the antibody to wild-type human IL-13Rα1 extracellular region. Accordingly, Phe233 was identified as an important residue on the receptor for binding of antibody 10G5. Conveniently, the human IL-13Rα1 extracellular region or the corresponding Phe233Ala mutant were fused via the C-terminus to a fragment of the gene 3 protein (amino acids 249-406) generally in accordance with the procedure described by Lowman et al., 1991 *Biochem.* 30:10832-10838. These IL-13Rα1-derived peptides were then displayed on M13 bacteriophage and assayed by ELISA for binding to immobilized 10G5 or 1D9. Briefly, mAbs were passively adsorbed onto 96-well MAXISORP™ plates (NUNC) following overnight incubation of 100 μl/well of 2.5 μg/mL mAb diluted in PBS buffer. Coating solutions were discarded, plates were blocked by incubation with blocking buffer for hour at room temperature, then washed once with wash buffer. Phage samples serially diluted with 1% w/v skim milk powder in PBS (diluting buffer) were then transferred into mAb-coated plates (100 μL/well). Following incubation at room temperature for 2 hours, plates were washed 3 times, and bound phage labeled with anti-M13 IgG HRP-conjugated polyclonal antibody, and detected by addition of TMB substrate. TMB color development was quenched by addition of 2 M aqueous sulfuric acid, and absorbance at 450 nm was measured.

Example 9

Antibody Identification

Methods.

The variable heavy and the variable light sequences of antibody 10G5 (SEQ ID NOs:43 and 47, respectively) were cloned in a Fab phage-display vector, pFab3d (FIGS. 3, 4A, and 4B) with a 1929 bp XhoI/ApaI fragment from the PKS3 locus of the fungus *Glarea lozoyensis* cloned at the XhoI/ApaI site as a stuffer in the light chain construct, then randomly mutated in the variable heavy and light CDR3 regions (each library possessing ≥$10^8$ functional diversity). The resultant mutants were then panned against biotinylated human and primate (rhesus and cynomologous monkey) IL-13Rα1 in solution using standard phage display protocols (see, e.g., *Phage Display: A Laboratory Manual,* 2001, Cold Spring Harbor Laboratory Press). Human and primate sequences have been disclosed in the literature; see, e.g., GENBANK Accession Nos. U62858, CAA70508, and AAP78901. By lowering the concentration of target in each subsequent round of panning (e.g., 10 nM, 1 nM, 0.1 nM, and 0.01 nM), the stringency of panning was effectively increased, thereby enriching for higher and higher affinity phage with each subsequent round. Phage ELISA was used as the primary assay to determine the ability of the phage-bound recombinant Fabs to recognize the biotinylated IL-13Rα1 immobilized on streptavidin plates (see, e.g., *Phage Display: A Laboratory Manual,* supra). Myc-capture ELISA and dissociation assays (general protocols described herein) were used as secondary screening tools. BIACORE™ surface plasmon resonance and KINEXA™ kinetic exclusion assays were performed to characterize the binding kinetics of the antibodies identified. These assays were performed in accordance with the published manufacturers' protocols. Specific antibodies were converted into full-length antibodies of subclass IgG4 for expression, production and characterization in mammalian cells (general protocol described below).

Myc Capture and Dissociation Assays.

Two assays are run in parallel. The first (I) measured the amount of antibody captured from peripreps. This assured that data was collected only from wells that had sufficient and equivalent amounts of antibody. The second (II) measured the dissociation of IL-13 receptor from the plate-bound antibody.

Assay (I):

IMMULON®-4 plates (DYNATECH, #3855) were coated with polyclonal anti-human kappa antibody (Immunology Consultants Lab, #GKBF-80A-K116) at 5 μg/ml in PBS (INVITROGEN, #14290-144) (50 μl/well) and incubated overnight at 4° C. Blocking buffer (200 μl/well) was added and the plates were incubated for 1 hour at room temperature. The plates were washed three times with wash buffer. Neat periprep was added, 50 μl/well, and left for 2 hours at room temperature. The plates were washed three times with wash buffer. Fifty μg/ml of human gamma globulin (Pierce, #31879) was added in block buffer and left to incubate overnight at 4° C. The plates were washed three times with wash buffer in the morning and afternoon followed by the addition of 150 μl/well of block buffer while incubating at 37° C. throughout. The plates were washed three times with wash buffer. Bound antibody was detected with biotin anti-Myc (Upstate, #16-212) at 1 μg/ml in blocking buffer (60 μl/well) for 1 hour at room temperature. The plates were washed three times with wash buffer. Streptavidin-europium (Wallac, #1244-360) was added at 100 ng/ml in Europium buffer (100 μl/well) for 20 minutes at room temperature. A final wash step (three times) was performed and enhancement solution (Wallac, #1244-105) at 150 μl/well was added for 1 hour at room temperature. Plates were read by time-delayed fluorescence on a VICTOR (PERKIN-ELMER) plate reader.

Assay (II):

IMMULON®-4 plates (DYNATECH, #3855) were coated with polyclonal anti-human kappa antibody (Immunology Consultants Lab, #GKBF-80A-K116) at 5 μg/ml in PBS (INVITROGEN, #14290-144) (50 μl/well) and incubated overnight at 4° C. Blocking buffer (200 μl/well) was added and the plates were incubated for 1 hour at room temperature. The plates were washed three times with wash buffer. Neat periprep was added, 50 μl/well, and left for 2 hours at room temperature. The plates were washed three times with wash buffer. Sixty μl/ml of 400 ng/ml FLAG®-tagged human IL13 receptor was added with 50 μg/ml of human gamma globulin (Pierce, #31879) in block buffer and left to incubate overnight at 4° C. The plates were washed three times with wash buffer at two, six-hour intervals followed by the addition of 150 μl/well of block buffer. Incubations were carried out at 37° C. The plates were washed three times with wash buffer. Residual IL-13 receptor was detected with biotin anti-FLAG® (IBI, #3081/6H2411) at 1 μg/ml in blocking buffer (60 μl/well) for 1 hour at room temperature. The plates were washed three times with wash buffer. Streptavidin-europium (Wallac, #1244-360) was added at 100 ng/ml in Europium buffer (100 μl/well) for 20 minutes at room temperature. A final wash step (three times) was performed and enhancement solution (Wallac, #1244-105), 150 μl/well, was added for 1 hour at room temperature. Plates were read by time-delayed fluorescence on a Victor (Perkin-Elmer) plate reader.

Conversion to Full-Length IgGs.

Anti-IL13Rα1 monoclonal antibodies were converted into whole antibody of subclass IgG4 for expression and production in mammalian cells. Their variable regions were PCR-amplified from the corresponding Fab vectors and in-frame cloned into a LONZA pCON antibody expression vector with leader sequences in front of the antibody sequences. In the vector, genomic DNA sequences for all constant regions for light and heavy chains were already engineered in the vectors. The expression is driven by a human cytomegalovirus (CMV) early promoter and followed by an SV40 polyadenylation signal. The plasmids have bacterial sequence for plasmid replication and ampicillin selection marker and the plasmid for the light chain, pCONKAPPA, has the GS gene for glutamine synthetase as a selection marker in mammalian cells. In-frame fusion of variable regions allows the proper expression of whole antibody. By design, leader sequences from mouse light and heavy chains were included in front of the antibody open reading frames. A consensus Kozak sequence (italics only) was also included surrounding the ATG start codon to improve protein expression level. Forward and reverse primers were designed for PCR amplification of four variable regions. For 10G5 light chain variable region, forward primer, 5'-ATC G<u>AAGCTT</u>GC CGC CAC CAT G <u>AGTGTGCCCACTCAGGTCCTGGGGTTGCTGCTGC TGTGGCTTACAGATGCCAGATGTGA</u> AAT TGT GTT GAC GCA GTC T-3' (SEQ ID NO:88) and reverse primer, 5'-CCA <u>CCGTACGTT</u> TGA TTT CCA C-3' (SEQ ID NO:89) were employed. For 10G5 heavy chain variable region, forward primer, 5'-ACT GAAGCTTGC CGC CAC CAT GGAATGGAGCTGGGTCTTTCTCTTCTTCCTG TCAGTAACTACAGGTGTCCACTCCGA GGT GCA GCT GGT GCA GTC T-3' (SEQ ID NO:90) and reverse primer, 5'-ACC GAT GGGCCC TTG GTG GAG GCT-3' (SEQ ID NO:91) were employed. The leader sequences are in bold and underlined and the cloning sites (HindIII in the forward primers for both light and heavy chains, in the reverse primers, BsiWI for the light chain and ApaI for the heavy chain) are given in underlining and italics.

The variable regions were PCR-amplified for 20 cycles using these pairs of primers and Fab vectors carrying 10G5 variable region sequences. PCR products were digested with HindIII and BsiWI for light chains and HindIII and ApaI for heavy chains. Enzyme-digested PCR fragments were cloned into Lonza's vectors (pCONKAPPA for light chain and pCONGAMMA4 for heavy chain). The entire expression cassette of respective heavy chain from pCONGAMMA4 vectors digested with NotI and SaiI was then inserted into the corresponding light chain vector digested with the same enzymes. The entire open reading frames for both light chain and heavy chain were verified by DNA sequence analysis.

Antibody Expression, Purification and Characterization.

Either combined light chain and heavy chain plasmid DNA or a 1:1 ratio mixture of corresponding light and heavy chain plasmid DNA were transfected in 293-derived cell lines. For pCON vectors, 293 FREESTYLE™ suspension cell line from INVITROGEN was used along with its transfection reagents. For 200 ml of 293 FREESTYLE™ cells, 100 μg each of heavy and light chain plasmid DNA and 300 μl of reagents were used for transfection. The transfected cells were incubated at 37° C./5% $CO_2$ for 7-8 days before harvest. Culture medium was harvested, filtered and concentrated using by low speed MILLIPORE CENTRICON® centrifugation (concentrator, MILLIPORE).

Results.

Figure 5:
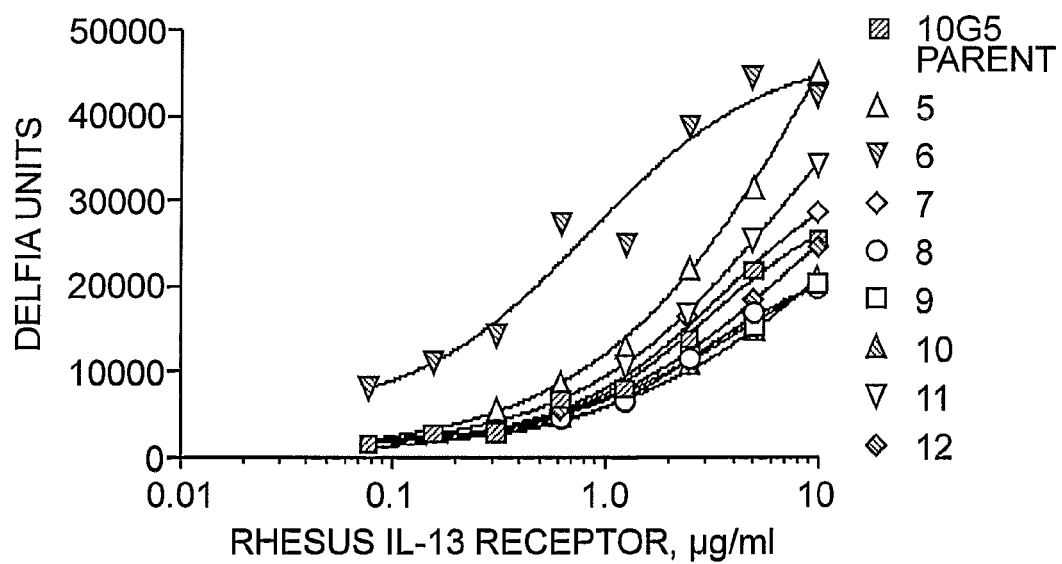
FIG. 5 illustrates binding of mutated Fabs from periplasmic preparations to rhesus IL-13Rα1.
Figure 6:
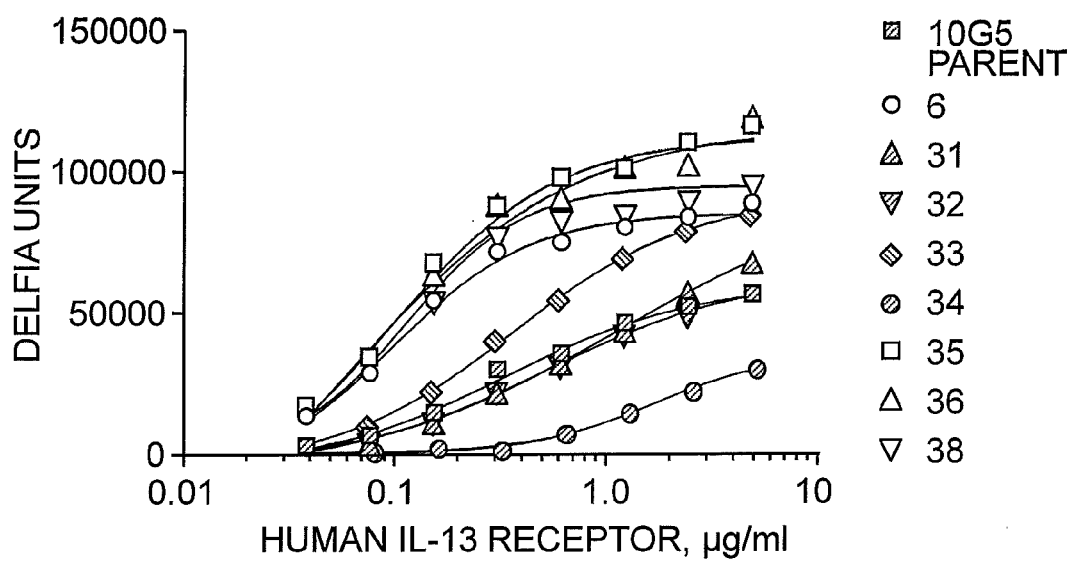
FIG. 6 illustrates ELISA analysis of binding of periplasmic preparations of 10G5 mutants to human IL-13Rα1.
Figure 7:
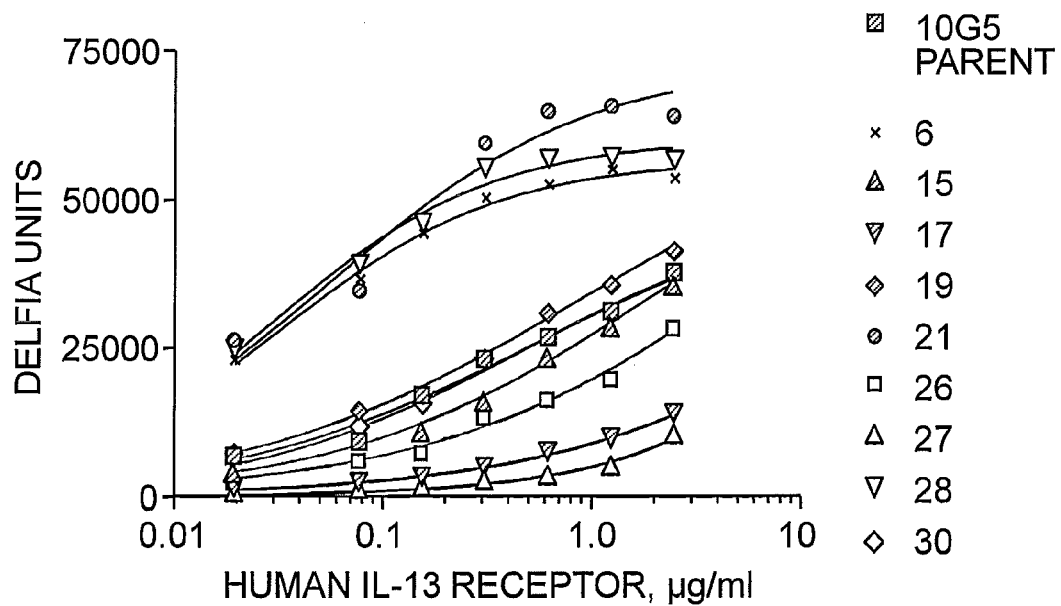
FIG. 7 illustrates ELISA analysis of binding of periplasmic preparations of 10G5 mutants to human IL-13Rα1.
Figure 8:
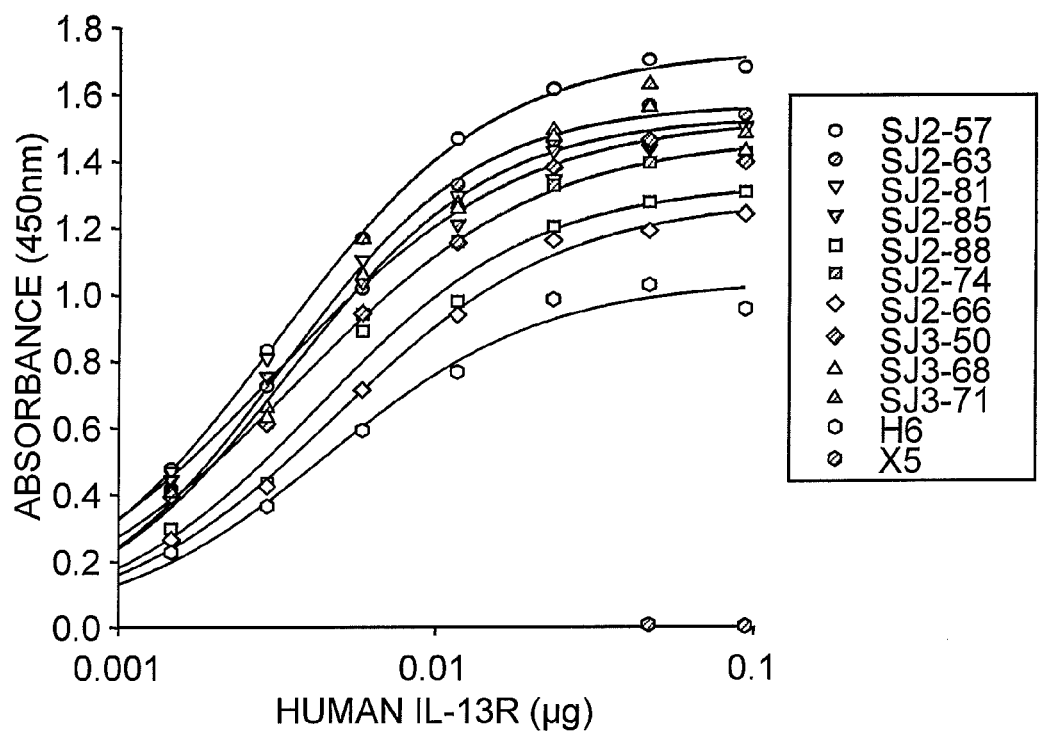
FIG. 8 illustrates Myc-capture ELISA data for light chain variant clones.

ELISA analyses are presented in FIGS. 5-8. In FIGS. 5-7, the mutants significantly distinguished by their activity were 10G5H6 (VHCDR3: SEQ ID NO:5; VLCDR3: SEQ ID NO:41); 10G5H5 (VHCDR3: SEQ ID NO:4; VLCDR3: SEQ ID NO:41); 10G5H11 (VHCDR3: SEQ ID NO:3; VLCDR3: SEQ ID NO:41); and 10G5H33 (VHCDR3: SEQ ID NO:25 (involving a The=>Ile residue change in the third to last amino acid residue therein); VLCDR3: SEQ ID NO:41). FIG. 8 illustrates ten mutants highlighted as functioning more effectively than 10G5H6. The mutants tested in FIG. 8 have $EC_{50}$ values and possess the heavy and light CDR3 regions as listed in Table 4.

TABLE 4

| Antibody | VHCDR3 | VLCDR3 | $EC_{50}$ (μM) |
|---|---|---|---|
| SJ2-66 | SEQ ID NO: 5 | SEQ ID NO: 28 | 1.757 |
| 10G5H6 | SEQ ID NO: 5 | SEQ ID NO: 41 | 1.636 |
| SJ2-88 | SEQ ID NO: 5 | SEQ ID NO: 27 | 1.536 |
| SJ3-50 | SEQ ID NO: 5 | SEQ ID NO: 29 | 1.341 |
| SJ2-74 | SEQ ID NO: 5 | SEQ ID NO: 32 | 1.308 |
| SJ2-63 | SEQ ID NO: 5 | SEQ ID NO: 33 | 1.248 |
| SJ3-68 | SEQ ID NO: 5 | SEQ ID NO: 34 | 1.24 |
| SJ3-71 | SEQ ID NO: 5 | SEQ ID NO: 35 | 1.186 |
| SJ2-57 | SEQ ID NO: 5 | SEQ ID NO: 36 | 1.14 |
| SJ2-85 | SEQ ID NO: 5 | SEQ ID NO: 37 | 1.123 |
| SJ2-81 | SEQ ID NO: 5 | SEQ ID NO: 38 | 0.9334 |

KINEXA® analyses were performed on select antibodies. The data for specific full-length antibodies is illustrated in the Tables 5 and 6 containing data from two different experiments.

TABLE 5

| Antibody | VHCDR3 | VLCDR3 | $K_D$ |
|---|---|---|---|
| 10G5-1 | SEQ ID NO: 5 | SEQ ID NO: 38 | 54.84 pM |
| 10G5-2 | SEQ ID NO: 22 | SEQ ID NO: 38 | 45.44 pM |
| 10G5-4 | SEQ ID NO: 23 | SEQ ID NO: 38 | 66.93 pM |

TABLE 6

| Antibody | VHCDR3 | VLCDR3 | $K_D$ |
|---|---|---|---|
| 10G5 WT | SEQ ID NO: 40 | SEQ ID NO: 41 | 861 pM |
| 10G5H6 | SEQ ID NO: 5 | SEQ ID NO: 41 | 99.43 pM |
| 10G5-2 | SEQ ID NO: 22 | SEQ ID NO: 38 | 31.44 pM |
| 10G5-4 | SEQ ID NO: 23 | SEQ ID NO: 38 | 20.35 pM |
| 10G5-6 | SEQ ID NO: 7 | SEQ ID NO: 38 | 26.8 pM |

BIACORE™ analyses were performed on various antibodies in Fab format. Tables 7 and 8 illustrate data from two different experiments:

TABLE 7

| Antibody | VHCDR3 | VLCDR3 | $K_D$ |
|---|---|---|---|
| 10G5 WT | SEQ ID NO: 40 | SEQ ID NO: 41 | 4.5 nM |
| 10G5H6 | SEQ ID NO: 5 | SEQ ID NO: 41 | 0.6 nM |

TABLE 8

| Antibody | VHCDR3 | VLCDR3 | $K_D$ |
|---|---|---|---|
| 10G5 WT | SEQ ID NO: 40 | SEQ ID NO: 41 | 1.35 nM |
| 10G5H11 | SEQ ID NO: 3 | SEQ ID NO: 41 | 106 pM |
| 10G5R4-10 | SEQ ID NO: 15 | SEQ ID NO: 41 | 196 pM |
| 10G5R4-11 | SEQ ID NO: 16 | SEQ ID NO: 41 | 233 pM |
| 10G5R4-2A | SEQ ID NO: 7 | SEQ ID NO: 41 | 817 pM |
| 10G5R4-2B | SEQ ID NO: 23 | SEQ ID NO: 41 | 116 pM |
| 10G5SJ2-81 | SEQ ID NO: 5 | SEQ ID NO: 38 | 43 pM |

The data provided illustrate that antibodies could be identified, through the various screens and analyses conducted, with significantly enhanced affinity for IL-13Rα1. The antibodies uncovered demonstrated quite frequently a general consensus in their sequence. More specifically, it was concluded from these studies that (1) three residues in the heavy chain variable region CDR3 domain were more apt to positively effect function upon mutation, namely, residues 1, 7 and 9 of SEQ ID NO:40, and (2) three residues in the light chain variable region CDR3 domain were more apt to positively effect function upon mutation, namely, residues 2, 4 and 5 in SEQ ID NO:41.

Antibodies with a manipulated Fc region were also developed. The manipulations in the Fc region allowed for an antibody that exhibits reduced binding to FcγR receptors or C1q. Binding to FcRn (also known as the neonatal receptor or Brambell receptor) is not substantially modified nor is the antibody half-life. The purpose of the modifications was to generate antibodies that do not provoke (or provoke to a lesser extent) antibody-dependent cellular cytotoxicity (ADCC), complement-mediated cytotoxicity (CMC), or form immune complexes, while retaining normal pharmacokinetic (PK) properties. As will be acknowledged by the skilled artisan, the disclosed human antibody IgG structure (that encompasses SEQ ID NO:92) can be used in conjunction with any variety of $V_H$ and $V_L$ sequences disclosed herein, with the appropriate Cκ or Cλ, in the development of full-length antibodies.

KINEXA® analyses were performed on select antibodies with the manipulated Fc. Amino acid and nucleotide sequences for 10G5-6 in the manipulated IgG format are set forth in SEQ ID NOs:94 and 95, respectively. Table 9 summarizes data obtained for select full-length antibodies upon 2-curve $K_d$ analysis using KINEXA®.

TABLE 9

| Antibody | VHCDR3 | VLCDR3 | $K_D$ |
|---|---|---|---|
| 10G5-6 IgG4 | SEQ ID NO: 7 | SEQ ID NO: 38 | 44.36 pM |
| 10G5-6 IgG2m4 | SEQ ID NO: 7 | SEQ ID NO: 38 | 30.79 pM |
| 10G5 WT IgG2m4 | SEQ ID NO: 40 | SEQ ID NO: 41 | 2.06 nM |
| 10G5H6 IgG2m4 | SEQ ID NO: 5 | SEQ ID NO: 41 | 94.64 pM |

Antibodies manipulated in this manner have been found to exhibit several advantages over the native IgG isotypes. The first is that they do not bind C1q as strongly as IgG2, rendering it less effective in activating the complement cascade. The manipulated antibodies also do not bind, or exhibit significantly reduced binding, to Fcγ receptors at physiologically relevant levels, in particular FcγRI, which eliminates (or significantly reduces) any undesired NK-cell or T-cell activation; significantly impedes the antibody's ability to mediate ADCC; and eliminates (or significantly reduces) a potential alternative sink for the antibody in vivo. The resultant antibodies also retain the half-life and basic structure of an IgG2, which is highly desirable. The blood half-life of 10G5-6 IgG2 m4 was found in a separate study to be in the order of 306 hours when tested in SCID mice. This half-life is comparable with the numbers reported for IgG2; see, e.g., Zuckier et al., 1994 *Cancer Suppl.* 73:794-799.

Example 10

Functional Studies—Eotaxin Release

NHDF Eotaxin Release Assay.

NHDF cells were purchased from Cambrex (#CC-2509) and were cultured in FGM media (Cambrex, #CC-3132) supplemented with additives provided, referred to below as complete media. Cells were passaged 1:3 or 1:5 once a week and were monitored for responsiveness to IL-13 prior to use. To assess antagonistic activity of IL-13Rα1 antibodies, cells were resuspended to $2 \times 10^6$/ml in complete media containing 20 ng/ml PMA (SIGMA, #P8139) and 20 μg/ml polymyxin (SIGMA, #P4932) and plated in 96-well flat bottom plates (COSTAR, #3595) at $1 \times 10^5$ cell/well. Antibody titrations were added to the cells and incubated for 30 minutes at 37° C. in a 5% $CO_2$ incubator. Recombinant rhesus IL-13 or recombinant human IL4 (BD PHARMINGEN, #554605) was then used at the respective $EC_{50}$ for each cytokine and incubated overnight at 37° C. in a 5% $CO_2$ incubator. Supernatants were removed and assayed for eotaxin content by immunoassay. Briefly, IMMULON®-4 plates (DYNATECH, #3855) were coated with 2 μg/ml anti-human eotaxin antibody (PHARMINGEN, #555035) in PBS (INVITROGEN, #14190-144) overnight at 4° C. The plates were blocked with blocking buffer for 1 hour at room temperature and washed three times with wash buffer. Supernatants from the NHDF cells were added to the plates along with a recombinant human eotaxin standard (R&D Systems, #320-EO). The samples were captured for 2 hours at room temperature, washed and biotinylated anti-human Eotaxin detection antibody (PHARMINGEN, #555060) was added at 200 ng/ml for 1 hour at room temperature. Plates were washed and streptavidin-europium (Wallac, #1244-360) was added at a concentration of 100 ng/ml for 20 minutes at room temperature. A final wash step was performed and enhancement solution (Wallac, #1244-105) was added for 1 hour at room temperature. Plates were read by time-delayed fluorescence on a VICTOR (PERKIN-ELMER) plate reader.

Results.

Figure 9:
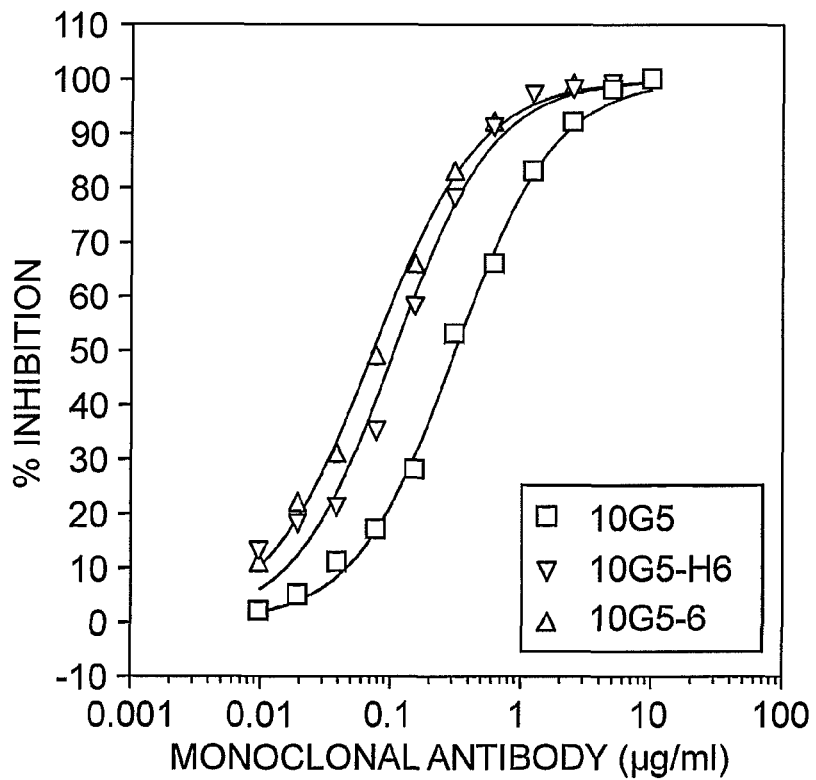
FIG. 9 illustrates the functioning of 10G5, 10G5H6, and 10G5-6 in a NHDF eotaxin release assay.
Figure 10:
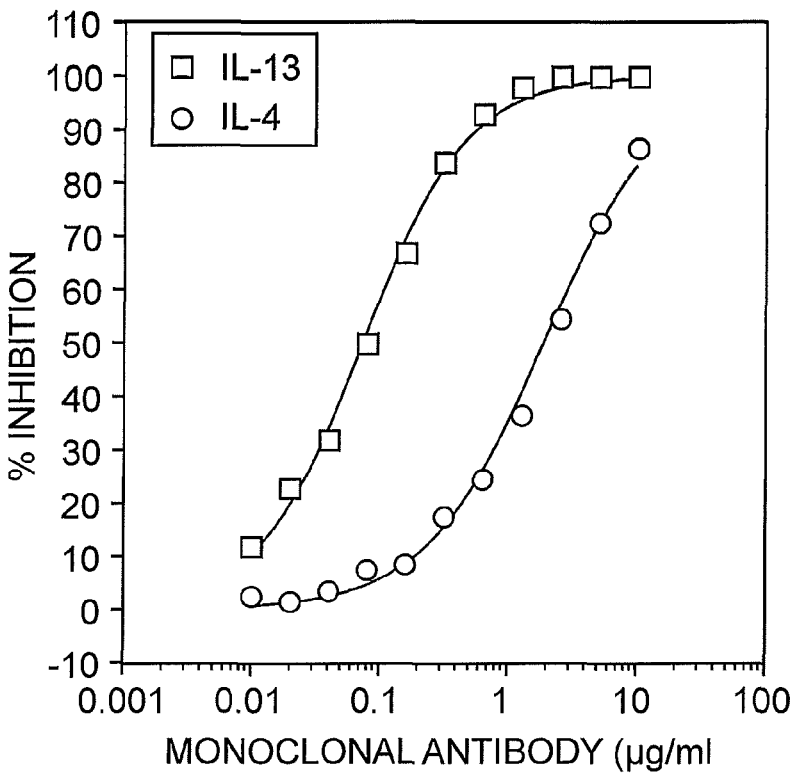
FIG. 10 illustrates the functioning of 10G5-6 in blocking IL-13- and IL-4-stimulated eotaxin release in NHDF cells.

Eotaxin release from normal human dermal fibroblast (NHDF) cells upon contact with IL-13Rα1-specific antibodies was analyzed. The assays were carried out using either IL-13 and/or IL-4 as a stimulant. When IL-13 was used as the inducing agent, the optimized antibodies were at least 2-fold more potent in these types of assays than the parental form, 10G5. An example of the fold-difference in functioning is illustrated in FIG. 9, where $IC_{50}$ values for 10G5, 10G5H6, and 10G5-6 were determined to be 310 ng/mL (~2 nM), 110 ng/mL (~730 pM), and 70 ng/mL (~467 pM), respectively, with IL-13 as the stimulant. FIG. 10 illustrates antibody inhibition of the formation of eotaxin by NHDF cells where IL-4 is used as the stimulant. An experiment was performed with a number of full-length antibodies of the present description. Data concerning inhibition of eotaxin release from NHDF cells upon stimulation by IL-13 is summarized in Table 10.

TABLE 10

| Antibody | VHCDR3 | VLCDR3 | $EC_{50}$ |
|---|---|---|---|
| 10G5 WT | SEQ ID NO: 40 | SEQ ID NO: 41 | 2.309 μg/ml |
| 10G5-1 | SEQ ID NO: 5 | SEQ ID NO: 38 | 0.497 μg/ml |
| 10G5-2 | SEQ ID NO: 22 | SEQ ID NO: 38 | 0.456 μg/ml |
| 10G5-3 | SEQ ID NO: 5 | SEQ ID NO: 39 | 0.614 μg/ml |
| 10G5-4 | SEQ ID NO: 23 | SEQ ID NO: 38 | 0.330 μg/ml |
| 10G5-5 | SEQ ID NO: 23 | SEQ ID NO: 41 | 0.939 μg/ml |
| 10G5H6 | SEQ ID NO: 5 | SEQ ID NO: 41 | 0.474 μg/ml |

Data concerning inhibition of eotaxin release from NHDF cells upon stimulation by IL-4 is summarized in Table 11.

TABLE 11

| Antibody | VHCDR3 | VLCDR3 | $EC_{50}$ |
|---|---|---|---|
| 10G5 WT | SEQ ID NO: 40 | SEQ ID NO: 41 | 4.533 μg/ml |
| 10G5-1 | SEQ ID NO: 5 | SEQ ID NO: 38 | 0.907 μg/ml |
| 10G5-2 | SEQ ID NO: 22 | SEQ ID NO: 38 | 0.730 μg/ml |
| 10G5-3 | SEQ ID NO: 5 | SEQ ID NO: 39 | 0.983 μg/ml |
| 10G5-4 | SEQ ID NO: 23 | SEQ ID NO: 38 | 0.660 μg/ml |
| 10G5-5 | SEQ ID NO: 23 | SEQ ID NO: 41 | 2.267 μg/ml |
| 10G5H6 | SEQ ID NO: 5 | SEQ ID NO: 41 | 1.438 μg/ml |

Example 11

Functional Studies—STAT6 Phosphorylation

NHDF STAT6 Phosphorylation Assay.

NHDF cells were purchased from Cambrex (#CC-2509) and were cultured in FGM media (Cambrex, #CC-3132) supplemented with additives provided. Plate NHDF cells at 2e6/ml in 50 μl volume in 96-well V-bottom polypropylene PCR plates (USA Scientific, #1442-9596) in RPMI Media (INVITROGEN, #22400-071). Anti-IL-13R antibodies were added in 25 μl volume and incubated for 30 minutes at 4° C. Recombinant rhesus IL-13 or recombinant human IL-4 (PHARMINGEN) was added in 25 μl volume. The plates were warmed to 37° C. in PCR machine for 20 minutes and, immediately, equal volume of 2× lysis buffer (100 μl) was added. pSTAT6 was measured by immunoassay. IMMULON®-4 plates (DYNATECH, #3855) were coated with anti-human phospho STAT6 (BD Transduction Labs, 621995) at 10 μg/ml in PBS (INVITROGEN, #14290-144) (50 μl/well) overnight at 4° C. Blocking buffer (200 μl/well) was added for 1 hour at room temperature. The plates were washed three times with wash buffer. Fifty μl/well lysate was added and incubated for 2 hours at room temperature. The plates were washed three times with wash buffer. Detection was enabled with biotin anti-STAT6 (BD Transduction Labs, conjugated 20:1 molar ratio) at 2 μg/ml in blocking buffer (60 μl/well) added for 1 hour at room temperature. The plates were washed three times with wash buffer. Streptavidin-Europium (Wallac, #1244-360) at 100 ng/ml was added in europium buffer (100 μl/well) for 20 minutes at room temperature. The plates were washed three times with wash buffer. Enhancement solution (Wallac, #12244-105) was added (150 μl/well) for 1 hour at room temperature, and plates were read by time-delayed fluorescence on a VICTOR (PERKIN-ELMER) reader.

Results.

Figure 11:
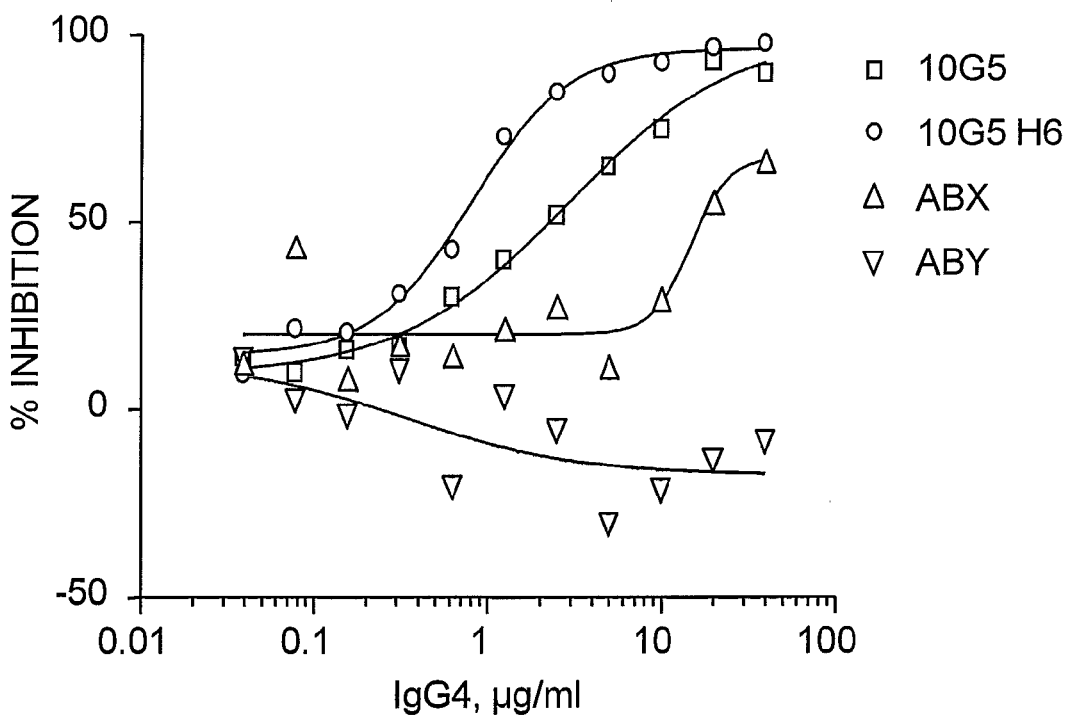
FIG. 11 illustrates the functioning of 10G5 and 10G5H6 in an IL-13-induced STAT6 assay.
Figure 12:
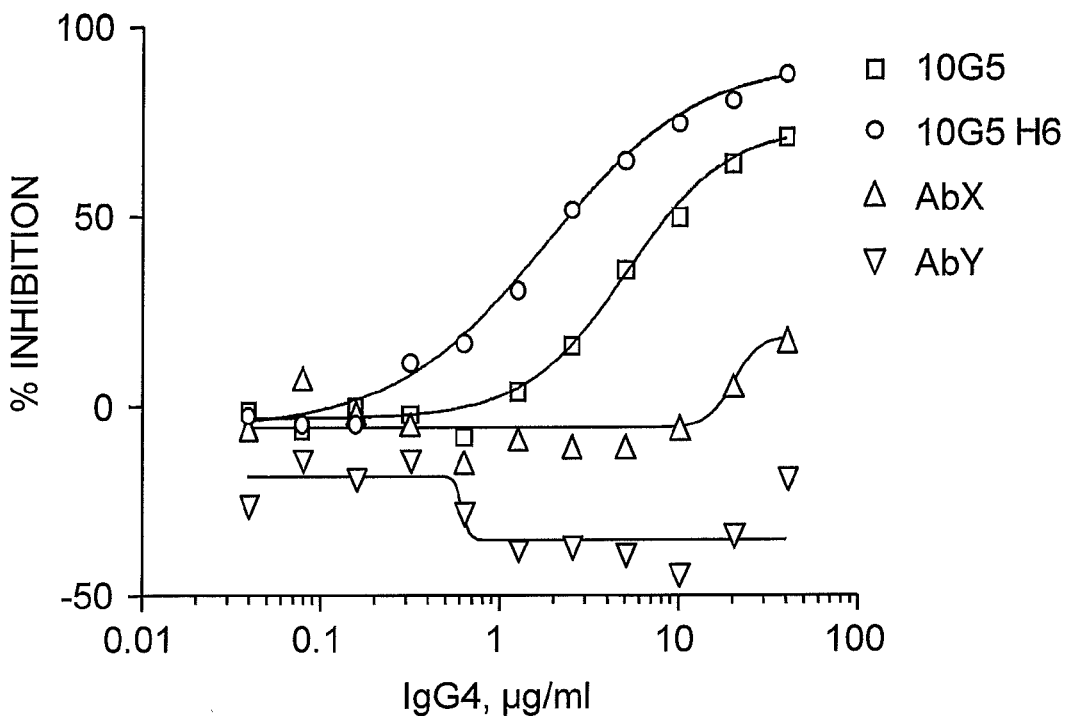
FIG. 12 illustrates the functioning of 10G5 and 10G5H6 in an IL-4-induced STAT6 assay.

Antibody inhibition of IL-13- and IL-4-induced STAT6 phosphorylation was studied in NHDF cells. When IL-13 was used as the inducing agent, the optimized antibodies were at least 3-fold more potent in these types of assays than the parental form, 10G5. An example of the fold-difference in functioning is illustrated in FIG. 11, where the $EC_{50}$s for 10G5 and 10G5H6 were determined to be 2.9 μg/ml and 0.8 μg/ml, respectively, with IL-13 as the stimulant. FIG. 12 illustrates antibody inhibition of STAT6 phosphorylation in NHDF cells, where IL-4 is used as the stimulant. Results of this analysis indicated $EC_{50}$s of 5.0 μg/ml and 1.8 μg/ml for 10G5 and 10G5H6, respectively.

Example 12

Functional Studies—TARC Release

Thymus and Activation-Regulated Chemokine (TARC) Release Assay (Dog, Rhesus or Human).

Blood was collected in heparinized VACUTAINER® tubes (VWR, VT6480). PBMCs were isolated over Lymphocyte Separation Media (ICN, 50494x). PBMCs or whole blood was plated in 96-well flat bottom plates (COSTAR, #2595). Antibodies were added and incubated for 30 minutes at room temperature. Recombinant rhesus IL-13 was added at 10 ng/ml final concentration and incubated for 24-72 hours at 37° C. with $CO_2$ in a humidified chamber. Supernate or plasma was collected (TARC can be detected as early as 24 hours but levels continue to increase). TARC was measured by immunoassay. IMMULON®-4 plates (DYNATECH, 3855) were coated with anti-human TARC (R&D, #AF364) at 2 μg/ml in PBS (INVITROGEN, #14290-144), 50 μl/well. The plates were incubated overnight at 4° C. Blocking buffer (200 μl/well) was added and incubated for 1 hour at room temperature. The plates were washed three times with wash buffer. Plasma or supernate was added, 50 μl/well, and incubated for 2 hours at room temperature (plasma diluted 1:2). A standard curve was included starting at 20 ng/ml recombinant human TARC diluted 2-fold. The plates were washed three times with wash buffer. Detection was carried out with biotin anti-human TARC (RDI, #RDI-TarcabrP1, conjugated to biotin 20:1 molar ratio) at 250 ng/ml in blocking buffer (60 μl/well) for 1 hour at room temperature. The plates were washed three times with wash buffer. Streptavidin-Europium (Wallac, #1244-360) was added 100 μl/well at 100 ng/ml in europium buffer for 20 minutes at room temperature. The plates were washed three times with wash buffer. Enhancement solution (Wallac, #12244-105), 150 μl/well, was added and incubated for 1 hour at room temperature. Time-delayed fluorescence was read in a VICTOR (PERKIN-ELMER) reader.

Results.

Figure 13:
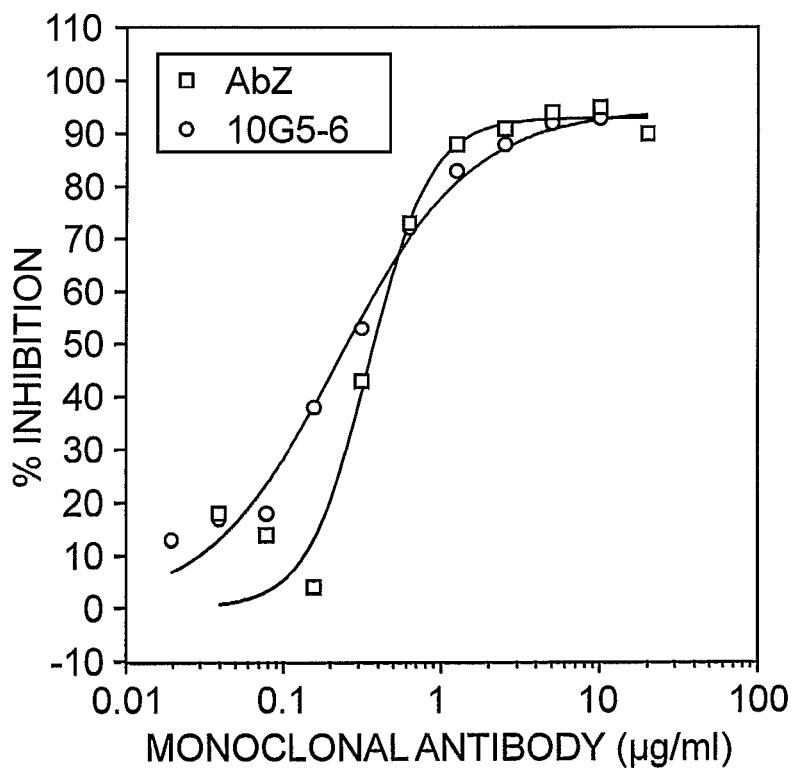
FIG. 13 illustrates the functioning of 10G5-6 in blocking IL-13-stimulated release of TARC(CCL17) in whole human blood.
Figure 14:
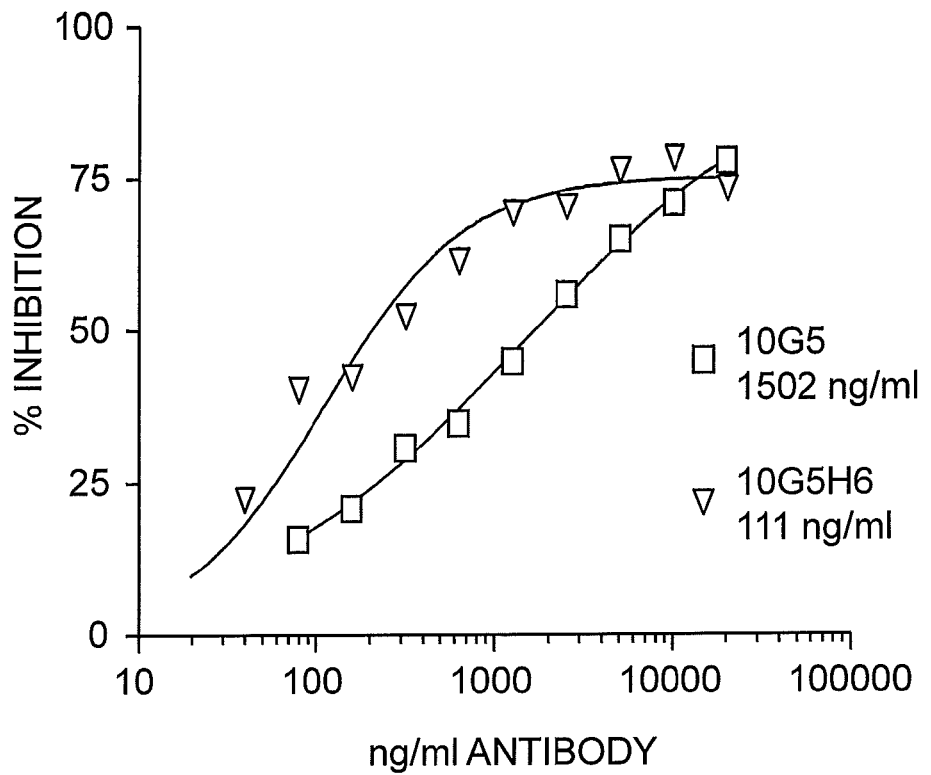
FIG. 14 illustrates the functioning of 10G5 and 10G5H6 in an IL-13-stimulated TARC release assay in whole human blood.
Figure 15:
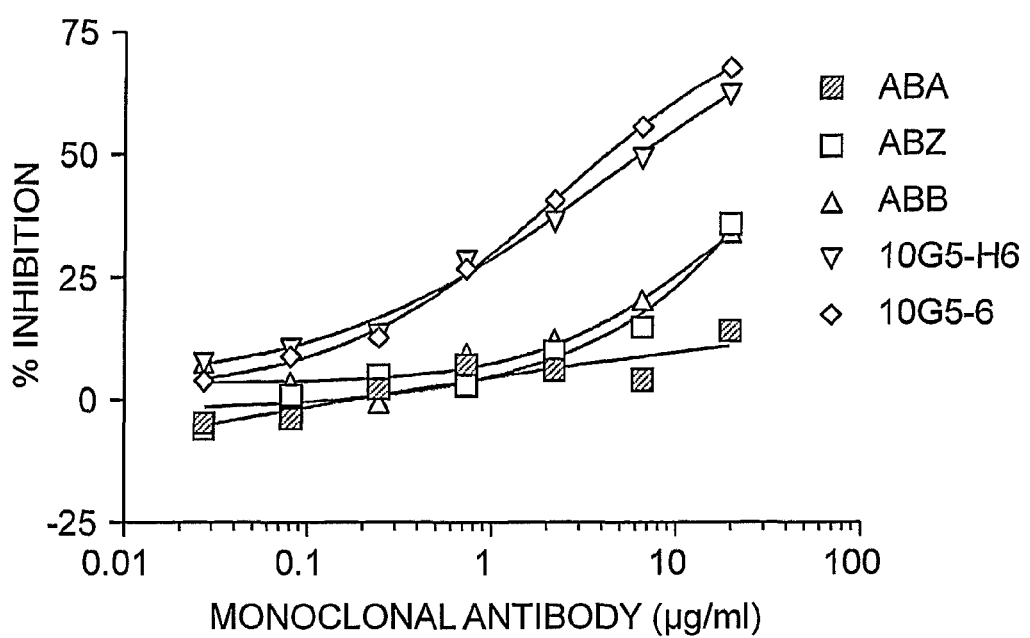
FIG. 15 illustrates the functioning of 10G5H6 and 10G5-6 in blocking rhesus IL-13-stimulated release of TARC in whole rhesus blood.

The effect of the present antibodies on TARC release following stimulation with 10 ng/mL of IL-13 was examined. FIG. 13 illustrates, for example, the ability of 10G5-6 to block the IL-13-stimulated release of TARC(CCL17) in whole human blood. The antibody yielded an $IC_{50}$ of ~112 ng/mL, 746 pM. FIG. 14 illustrates functioning of another antibody, 10G5H6, versus 10G5 WT (wild-type) in an IL-13-stimulated TARC release assay from whole human blood. FIG. 15 illustrates the effect of 10G5-6 alongside 10G5H6 in blocking the release of TARC after stimulation of whole rhesus blood with rhesus IL-13.

Example 13

Functional Studies—Inhibition of Cell Proliferation of Hodgkin's Disease

Methods.

10G5, 10G5H6 and 10G5-6 were assayed to determine whether the antibodies were effective in inhibiting cell proliferation of Hodgkin's disease cell line L1236. Hodgkin's and Reed-Sternberg cells have been studied previously with regard to the cytokine IL-13; see, e.g., Kapp et al., 1999 *J. Exp. Med.* 189:1939-1945; Skinnider et al., 2001 *Blood* 97:250-255; Skinnider et al., 2002 *Blood* 99:618-626; and in U.S. Pat. No. 6,468,528, and the methods of analyzing same are discussed therein.

Results.

Figure 17:
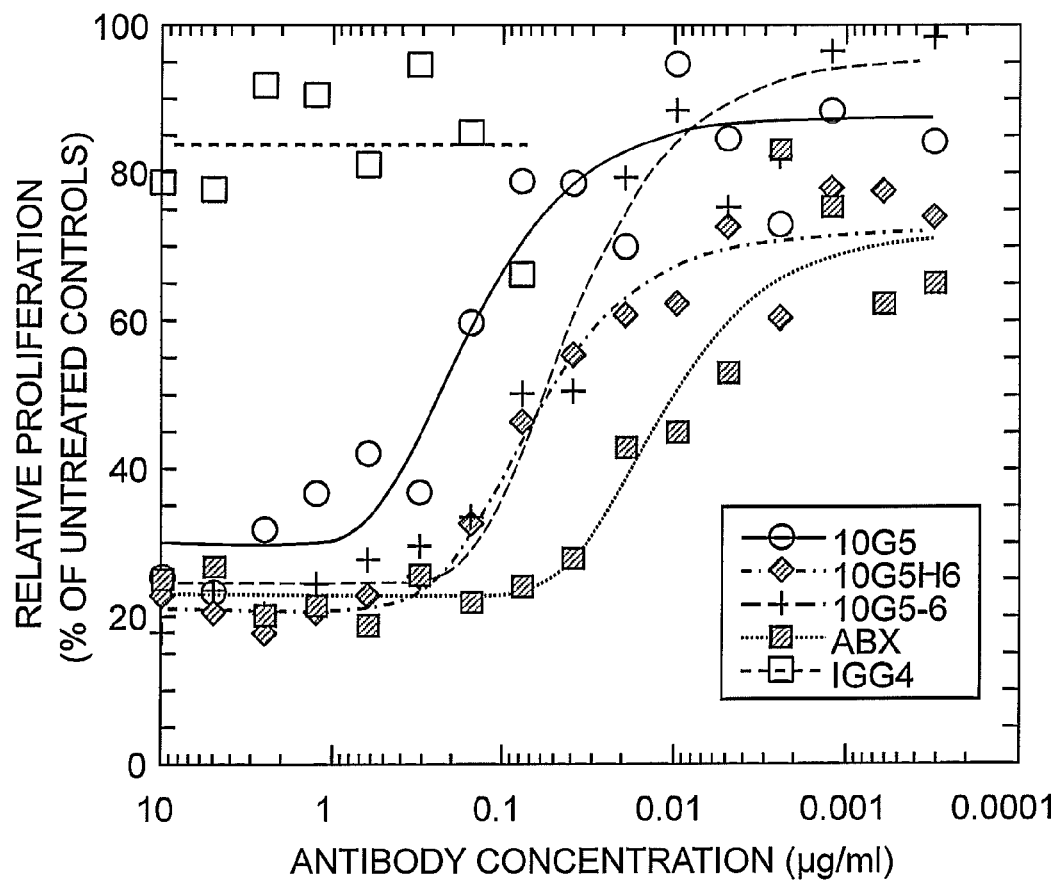
FIG. 17 illustrates inhibition of cell proliferation of Hodgkin's Disease cell line L1236 by 10G5, 10G5H6, and 10G5-6.

In this assay, 10G5 gave an $IC_{50}$ of about 300 ng/mL (2 nM), whereas both 10G5H6 and 10G5-6 yielded $IC_{50}$s of about 50 ng/ml (~330 pM) which for both represented a ca. 6-fold improvement over that of the parent 10G5 IgG. See FIG. 17.

What is claimed is:

1. An isolated antibody that binds to human interleukin 13 receptor alpha 1, comprising:
   (a) a heavy chain variable region comprising CDR1, CDR2, and CDR3 amino acid sequences as set forth in SEQ ID NO:82, SEQ ID NO:83, and SEQ ID NO:7, respectively; and
   (b) a light chain variable region comprising CDR1, CDR2, and CDR3 amino acid sequences as set forth in SEQ ID NO:84, SEQ ID NO:85, and SEQ ID NO:38, respectively.

2. The isolated antibody of claim 1, wherein the heavy chain variable region has the amino acid sequence as set forth in SEQ ID NO:63 and the light chain variable region has the amino acid sequence set forth in SEQ ID NO:71.

3. A composition comprising the antibody of claim 1 and a pharmaceutically acceptable carrier.

4. A composition comprising the antibody of claim 2 and a pharmaceutically acceptable carrier.

* * * * *

SEQUENCE LISTING

<160> NUMBER OF SEQ ID NOS: 123

<210> SEQ ID NO 1
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 1

Phe Pro Asn Trp Gly Ala Leu Asp Gln
1               5

```
<210> SEQ ID NO 2
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 2

Val Pro Asn Trp Gly Ser Leu Asp Thr
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 3

Phe Pro Asn Trp Gly Ser Met Asp Ala
1               5

<210> SEQ ID NO 4
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 4

Phe Pro Asn Trp Gly Ser Leu Asp His
1               5

<210> SEQ ID NO 5
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 5

Met Pro Asn Trp Gly Ser Phe Asp Tyr
1               5

<210> SEQ ID NO 6
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 6

Met Pro Asn Trp Gly Ser Phe Asp Thr
1               5

<210> SEQ ID NO 7
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 7

Met Pro Asn Trp Gly Ser Leu Asp His
1               5
```

```
<210> SEQ ID NO 8
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 8

Met Pro Asn Trp Gly Ser Phe Asp Ser
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 9

Met Pro Asn Trp Gly Ser Leu Asp Thr
1               5

<210> SEQ ID NO 10
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 10

Met Pro Asn Trp Gly Ser Leu Asp Ala
1               5

<210> SEQ ID NO 11
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 11

Met Pro Asn Trp Gly Ser Leu Asp Asn
1               5

<210> SEQ ID NO 12
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 12

Met Pro Asn Trp Gly Ala Leu Asp Ser
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 13

Met Pro Asn Trp Gly Ser Phe Asp Asn
1               5
```

```
<210> SEQ ID NO 14
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 14

Met Pro Asn Trp Gly Ser Leu Asp Tyr
1               5

<210> SEQ ID NO 15
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 15

Met Pro Asn Trp Gly Ser Phe Asp His
1               5

<210> SEQ ID NO 16
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 16

Met Pro Asn Trp Gly Ser Leu Asp Ser
1               5

<210> SEQ ID NO 17
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 17

Met Pro Asn Trp Gly Ser Leu Asp Gly
1               5

<210> SEQ ID NO 18
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 18

Val Pro Asn Trp Gly Ser Leu Asp Asn
1               5

<210> SEQ ID NO 19
<211> LENGTH: 28
<212> TYPE: PRT
<213> ORGANISM: Artificial sequence
<220> FEATURE:
<223> OTHER INFORMATION: Synthetic variant sequence with optimized CDR3

<400> SEQUENCE: 19

Cys Ala Arg Phe Pro Asn Trp Gly Ser Leu Asp His Trp Gly Gln Gly
1               5                   10                  15

Thr Leu Val Thr Val Ser Ser Ala Ser Ile Lys Gly
            20                  25
```

```
<210> SEQ ID NO 20
<211> LENGTH: 28
<212> TYPE: PRT
<213> ORGANISM: Artificial sequence
<220> FEATURE:
<223> OTHER INFORMATION: Synthetic variant sequence with optimized CDR3

<400> SEQUENCE: 20

Cys Ala Arg Met Pro Asn Trp Gly Ser Leu Asp His Trp Gly Gln Gly
1               5                   10                  15

Thr Leu Val Thr Val Ser Ser Ala Ser Thr Lys Gly
            20                  25

<210> SEQ ID NO 21
<211> LENGTH: 28
<212> TYPE: PRT
<213> ORGANISM: Artificial sequence
<220> FEATURE:
<223> OTHER INFORMATION: Synthetic variant sequence with optimized CDR3

<400> SEQUENCE: 21

Cys Ala Arg Met Pro Asn Trp Gly Ser Phe Asp Tyr Trp Gly Gln Gly
1               5                   10                  15

Thr Leu Val Thr Val Ser Ser Ala Ser Ile Lys Gly
            20                  25

<210> SEQ ID NO 22
<211> LENGTH: 12
<212> TYPE: PRT
<213> ORGANISM: Artificial sequence
<220> FEATURE:
<223> OTHER INFORMATION: Synthetic variant sequence with optimized CDR3

<400> SEQUENCE: 22

Val Arg Met Pro Asn Trp Gly Ser Leu Asp His Trp
1               5                   10

<210> SEQ ID NO 23
<211> LENGTH: 27
<212> TYPE: PRT
<213> ORGANISM: Artificial sequence
<220> FEATURE:
<223> OTHER INFORMATION: Synthetic variant sequence with optimized CDR3

<400> SEQUENCE: 23

Val Arg Met Pro Asn Trp Gly Ser Leu Asp His Trp Gly Gln Gly Thr
1               5                   10                  15

Leu Val Thr Val Ser Ser Ala Ser Ile Lys Gly
            20                  25

<210> SEQ ID NO 24
<211> LENGTH: 27
<212> TYPE: PRT
<213> ORGANISM: Artificial sequence
<220> FEATURE:
<223> OTHER INFORMATION: Synthetic variant sequence with optimized CDR3

<400> SEQUENCE: 24

Ala Arg Met Pro Asn Trp Gly Ser Leu Asp His Trp Gly Gln Gly Thr
1               5                   10                  15

Leu Val Thr Val Ser Ser Ala Ser Ile Lys Gly
            20                  25
```

```
<210> SEQ ID NO 25
<211> LENGTH: 25
<212> TYPE: PRT
<213> ORGANISM: Artificial sequence
<220> FEATURE:
<223> OTHER INFORMATION: Synthetic variant sequence with optimized CDR3

<400> SEQUENCE: 25

Phe Pro Asn Trp Gly Ser Phe Asp Tyr Trp Gly Gln Gly Thr Leu Val
1               5                   10                  15

Thr Val Ser Ser Ala Ser Ile Lys Gly
            20                  25

<210> SEQ ID NO 26
<211> LENGTH: 9
<212> TYPE: PRT
<213> ORGANISM: Artificial sequence
<220> FEATURE:
<223> OTHER INFORMATION: Synthetic heavy chain CDR3 optimized variant

<400> SEQUENCE: 26

Val Pro Asn Trp Gly Ser Leu Asp Ala
1               5

<210> SEQ ID NO 27
<211> LENGTH: 5
<212> TYPE: PRT
<213> ORGANISM: Artificial sequence
<220> FEATURE:
<223> OTHER INFORMATION: Synthetic light chain CDR3 optimized variant

<400> SEQUENCE: 27

Gln Arg Tyr Ser Thr
1               5

<210> SEQ ID NO 28
<211> LENGTH: 5
<212> TYPE: PRT
<213> ORGANISM: Artificial sequence
<220> FEATURE:
<223> OTHER INFORMATION: Synthetic light chain CDR3 optimized variant

<400> SEQUENCE: 28

Gln Arg Tyr Ala Thr
1               5

<210> SEQ ID NO 29
<211> LENGTH: 5
<212> TYPE: PRT
<213> ORGANISM: Artificial sequence
<220> FEATURE:
<223> OTHER INFORMATION: Synthetic light chain CDR3 optimized variant

<400> SEQUENCE: 29

Gln Met Tyr Ser Thr
1               5

<210> SEQ ID NO 30
<211> LENGTH: 5
<212> TYPE: PRT
<213> ORGANISM: Artificial sequence
<220> FEATURE:
<223> OTHER INFORMATION: Synthetic light chain CDR3 optimized variant

<400> SEQUENCE: 30

Gln Gln Val Gly Thr
1               5
```

```
<210> SEQ ID NO 31
<211> LENGTH: 5
<212> TYPE: PRT
<213> ORGANISM: Artificial sequence
<220> FEATURE:
<223> OTHER INFORMATION: Synthetic light chain CDR3 optimized variant

<400> SEQUENCE: 31

Gln Val Tyr Ser Thr
1               5

<210> SEQ ID NO 32
<211> LENGTH: 5
<212> TYPE: PRT
<213> ORGANISM: Artificial sequence
<220> FEATURE:
<223> OTHER INFORMATION: Synthetic light chain CDR3 optimized variant

<400> SEQUENCE: 32

Gln Gln Tyr Ser Thr
1               5

<210> SEQ ID NO 33
<211> LENGTH: 5
<212> TYPE: PRT
<213> ORGANISM: Artificial sequence
<220> FEATURE:
<223> OTHER INFORMATION: Synthetic light chain CDR3 optimized variant

<400> SEQUENCE: 33

Gln Ser Tyr Ser Thr
1               5

<210> SEQ ID NO 34
<211> LENGTH: 5
<212> TYPE: PRT
<213> ORGANISM: Artificial sequence
<220> FEATURE:
<223> OTHER INFORMATION: Synthetic light chain CDR3 optimized variant

<400> SEQUENCE: 34

Gln Gln Tyr Ala Thr
1               5

<210> SEQ ID NO 35
<211> LENGTH: 5
<212> TYPE: PRT
<213> ORGANISM: Artificial sequence
<220> FEATURE:
<223> OTHER INFORMATION: Synthetic light chain CDR3 optimized variant

<400> SEQUENCE: 35

Gln Gln Tyr Ser Ser
1               5

<210> SEQ ID NO 36
<211> LENGTH: 5
<212> TYPE: PRT
<213> ORGANISM: Artificial sequence
<220> FEATURE:
<223> OTHER INFORMATION: Synthetic light chain CDR3 optimized variant

<400> SEQUENCE: 36

Gln Thr Tyr Ser Thr
1               5
```

<210> SEQ ID NO 37
<211> LENGTH: 5
<212> TYPE: PRT
<213> ORGANISM: Artificial sequence
<220> FEATURE:
<223> OTHER INFORMATION: Synthetic light chain CDR3 optimized variant

<400> SEQUENCE: 37

Gln Gln Tyr Gly Ser
1               5

<210> SEQ ID NO 38
<211> LENGTH: 5
<212> TYPE: PRT
<213> ORGANISM: Artificial sequence
<220> FEATURE:
<223> OTHER INFORMATION: Synthetic light chain CDR3 optimized variant

<400> SEQUENCE: 38

Gln Gln Tyr Ala Ser
1               5

<210> SEQ ID NO 39
<211> LENGTH: 5
<212> TYPE: PRT
<213> ORGANISM: Artificial sequence
<220> FEATURE:
<223> OTHER INFORMATION: Synthetic light chain CDR3 optimized variant

<400> SEQUENCE: 39

Gln Gln Tyr Glu Ala
1               5

<210> SEQ ID NO 40
<211> LENGTH: 9
<212> TYPE: PRT
<213> ORGANISM: Artificial sequence
<220> FEATURE:
<223> OTHER INFORMATION: Synthetic 10G5 heavy chain CDR3

<400> SEQUENCE: 40

Phe Pro Asn Trp Gly Ser Phe Asp Tyr
1               5

<210> SEQ ID NO 41
<211> LENGTH: 5
<212> TYPE: PRT
<213> ORGANISM: Artificial sequence
<220> FEATURE:
<223> OTHER INFORMATION: Synthetic 10G5 light chain CDR3

<400> SEQUENCE: 41

Gln Gln Tyr Glu Thr
1               5

<210> SEQ ID NO 42
<211> LENGTH: 414
<212> TYPE: DNA
<213> ORGANISM: Artificial sequence
<220> FEATURE:
<223> OTHER INFORMATION: Synthetic 10G5 VH sequence with leader and
      additional constant region

<400> SEQUENCE: 42
tttgccctcg tccctggctt gttcctccaa ggagtctgtg ccgaggtgca gctggtgcag    60
tctggagcag aggtgaaaaa gcccggggag tctctgaaga tctcctgtaa gggttctgga   120

```
tacagcttta ccagctactg gatcggctgg gtgcgccaga tgcccgggaa aggcctggag    180
tggatggggg tcatctatcc tggtgactct tataccagat acagcccgtc cttccaaggc    240
caggtcacca tctcagccga caagtccatc agcaccgcct acctgcagtg gagcagcctg    300
aaggcctcgg acaccgccat gtattactgt gcgagattcc ccaactgggg ctcatttgac    360
tactggggcc agggaaccct ggtcaccgtc tcctcagcct ccaccaaggg ccca          414
```

<210> SEQ ID NO 43
<211> LENGTH: 354
<212> TYPE: DNA
<213> ORGANISM: Artificial sequence
<220> FEATURE:
<223> OTHER INFORMATION: Synthetic 10G5 VH sequence only

<400> SEQUENCE: 43

```
gaggtgcagc tggtgcagtc tggagcagag gtgaaaaagc ccggggagtc tctgaagatc    60
tcctgtaagg gttctggata cagctttacc agctactgga tcggctgggt gcgccagatg    120
cccgggaaag gcctggagtg gatggggtc atctatcctg gtgactctta taccagatac     180
agcccgtcct tccaaggcca ggtcaccatc tcagccgaca gtccatcag caccgcctac     240 ctgcagtgga gcagcctgaa ggcctcggac accgccatgt attactgtgc gagattcccc    300
aactggggct catttgacta ctggggccag ggaaccctgg tcaccgtctc ctca          354
```

<210> SEQ ID NO 44
<211> LENGTH: 138
<212> TYPE: PRT
<213> ORGANISM: Artificial sequence
<220> FEATURE:
<223> OTHER INFORMATION: Synthetic 10G5 VH sequence with leader and
      additional constant region

<400> SEQUENCE: 44

```
Phe Ala Leu Val Pro Gly Leu Phe Leu Gln Gly Val Cys Ala Glu Val
1               5                   10                  15

Gln Leu Val Gln Ser Gly Ala Glu Val Lys Lys Pro Gly Glu Ser Leu
            20                  25                  30

Lys Ile Ser Cys Lys Gly Ser Gly Tyr Ser Phe Thr Ser Tyr Trp Ile
        35                  40                  45

Gly Trp Val Arg Gln Met Pro Gly Lys Gly Leu Glu Trp Met Gly Val
    50                  55                  60

Ile Tyr Pro Gly Asp Ser Tyr Thr Arg Tyr Ser Pro Ser Phe Gln Gly
65                  70                  75                  80

Gln Val Thr Ile Ser Ala Asp Lys Ser Ile Ser Thr Ala Tyr Leu Gln
                85                  90                  95

Trp Ser Ser Leu Lys Ala Ser Asp Thr Ala Met Tyr Tyr Cys Ala Arg
            100                 105                 110

Phe Pro Asn Trp Gly Ser Phe Asp Tyr Trp Gly Gln Gly Thr Leu Val
        115                 120                 125

Thr Val Ser Ser Ala Ser Thr Lys Gly Pro
    130                 135
```

<210> SEQ ID NO 45
<211> LENGTH: 118
<212> TYPE: PRT
<213> ORGANISM: Artificial sequence
<220> FEATURE:
<223> OTHER INFORMATION: Synthetic 10G5 VH sequence only

<400> SEQUENCE: 45

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Val Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Phe Pro Asn Trp Gly Ser Phe Asp Tyr Trp Gly Gln Gly Thr
            100                 105                 110

Leu Val Thr Val Ser Ser
        115

<210> SEQ ID NO 46
<211> LENGTH: 369
<212> TYPE: DNA
<213> ORGANISM: Artificial sequence
<220> FEATURE:
<223> OTHER INFORMATION: Synthetic 10G5 VL sequence with leader and
      additional constant region

<400> SEQUENCE: 46
ttcttcctcc tgctactctg gctcccagat accaccggag aaattgtgtt gacgcagtct      60
ccaggcaccc tgtctttgtc tccaggggaa agagccaccc tctcctgcag ggccagtcag     120
agtattagca gcagctactt agcctggtac cagcagaaac ctggccaggc tcccaggctc     180
ctcatctatg gtgcatccag cagggccact ggcatcccag acaggttcag tggcagtggg     240
tctgggacag acttcactct caccatcagc agactggagc ctgaagattt tgcagtgtat     300
tactgtcagc agtatgagac gttcggccaa gggaccaagg tggaaatcaa acgaactgtg     360
gctgcacca                                                              369

<210> SEQ ID NO 47
<211> LENGTH: 312
<212> TYPE: DNA
<213> ORGANISM: Artificial sequence
<220> FEATURE:
<223> OTHER INFORMATION: Synthetic 10G5 VL sequence only

<400> SEQUENCE: 47
gaaattgtgt tgacgcagtc tccaggcacc ctgtctttgt ctccagggga aagagccacc      60
ctctcctgca gggccagtca gagtattagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatgaga cgttcggcca agggaccaag     300
gtggaaatca aa                                                          312

<210> SEQ ID NO 48
<211> LENGTH: 123
<212> TYPE: PRT
<213> ORGANISM: Artificial sequence
<220> FEATURE:

<223> OTHER INFORMATION: Synthetic 10G5 VL sequence with leader and
      additional constant region

<400> SEQUENCE: 48

Phe Phe Leu Leu Leu Leu Trp Leu Pro Asp Thr Thr Gly Glu Ile Val
1               5                   10                  15

Leu Thr Gln Ser Pro Gly Thr Leu Ser Leu Ser Pro Gly Glu Arg Ala
            20                  25                  30

Thr Leu Ser Cys Arg Ala Ser Gln Ser Ile Ser Ser Tyr Leu Ala
        35                  40                  45

Trp Tyr Gln Gln Lys Pro Gly Gln Ala Pro Arg Leu Leu Ile Tyr Gly
    50                  55                  60

Ala Ser Ser Arg Ala Thr Gly Ile Pro Asp Arg Phe Ser Gly Ser Gly
65                  70                  75                  80

Ser Gly Thr Asp Phe Thr Leu Thr Ile Ser Arg Leu Glu Pro Glu Asp
                85                  90                  95

Phe Ala Val Tyr Tyr Cys Gln Gln Tyr Glu Thr Phe Gly Gln Gly Thr
            100                 105                 110

Lys Val Glu Ile Lys Arg Thr Val Ala Ala Pro
        115                 120

<210> SEQ ID NO 49
<211> LENGTH: 104
<212> TYPE: PRT
<213> ORGANISM: Artificial sequence
<220> FEATURE:
<223> OTHER INFORMATION: Synthetic 10G5 VL sequence only

<400> SEQUENCE: 49

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Glu Thr Phe Gly
                85                  90                  95

Gln Gly Thr Lys Val Glu Ile Lys
            100

<210> SEQ ID NO 50
<211> LENGTH: 445
<212> TYPE: PRT
<213> ORGANISM: Artificial sequence
<220> FEATURE:
<223> OTHER INFORMATION: Synthetic 10G5-1,3 heavy chain

<400> SEQUENCE: 50

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Val Ile Tyr Pro Gly Asp Ser Tyr Thr Arg Tyr Ser Pro Ser Phe
 50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                 85                  90                  95

Ala Arg Met Pro Asn Trp Gly Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 51
<211> LENGTH: 118
<212> TYPE: PRT

<213> ORGANISM: Artificial sequence
<220> FEATURE:
<223> OTHER INFORMATION: Synthetic 10G5-1,3 VH

<400> SEQUENCE: 51

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Val Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Met Pro Asn Trp Gly Ser Phe Asp Tyr Trp Gly Gln Gly Thr
            100                 105                 110

Leu Val Thr Val Ser Ser
        115

<210> SEQ ID NO 52
<211> LENGTH: 1338
<212> TYPE: DNA
<213> ORGANISM: Artificial sequence
<220> FEATURE:
<223> OTHER INFORMATION: Synthetic 10G5-1,3 heavy chain

<400> SEQUENCE: 52

```
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatggggggtc atctatcctg gtgactctta taccagatac     180
agcccgtcct tccaaggcca ggtcaccatc tcagccgaca gtccatcag caccgcctac      240
ctccagtgga gcagcctgaa ggcctcggac accgccatgt attactgtgc gagaatgcct     300
aattggggct catttgacta ctggggccag ggaaccctgg tcaccgtctc ctcagcctcc     360
accaagggcc catccgtctt ccccctggcg ccctgctcca ggagcacctc cgagagcaca     420
gccgccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcacgaa gacctacacc     600
tgcaacgtag atcacaagcc cagcaacacc aaggtggaca gagagttga gtccaaatat     660
ggtcccccat gcccaccatg cccagcacct gagttcctgg ggggaccatc agtcttcctg     720
ttcccccaa acccaaggga cactctcatg atctcccgga cccctgaggt cacgtgcgtg     780
gtggtggacg tgagccagga agaccccgag gtccagttca actggtacgt ggatggcgtg     840
gaggtgcata atgccaagac aaagccgcgg gaggagcagt tcaacagcac gtaccgtgtg     900
gtcagcgtcc tcaccgtcct gcaccaggac tggctgaacg gcaaggagta caagtgcaag     960
gtctccaaca aaggcctccc gtcctccatc gagaaaacca tctccaaagc caaagggcag    1020
ccccgagagc cacaggtgta cacactgccc ccatcccagg aggagatgac caagaaccag    1080
gtcagcctga cctgcctggt caaaggcttc taccccagcg acatcgccgt ggagtgggag    1140
agcaatgggc agccggagaa caactacaag accacgcctc ccgtgctgga ctccgacggc    1200
```

```
tccttcttcc tctacagcag gctaaccgtg gacaagagca ggtggcagga ggggaatgtc    1260
ttctcatgct ccgtgatgca tgaggctctg cacaaccact acacacagaa gagcctctcc    1320
ctgtctctgg gtaaatga                                                  1338
```

<210> SEQ ID NO 53
<211> LENGTH: 354
<212> TYPE: DNA
<213> ORGANISM: Artificial sequence
<220> FEATURE:
<223> OTHER INFORMATION: Synthetic 10G5-1,3 VH

<400> SEQUENCE: 53

```
gaggtgcagc tggtgcagtc tggagcagag gtgaaaaagc ccggggagtc tctgaagatc     60
tcctgtaagg gttctggata cagctttacc agctactgga tcggctgggt gcgccagatg    120
cccgggaaag gcctggagtg gatggggggtc atctatcctg gtgactctta taccagatac    180
agcccgtcct tccaaggcca ggtcaccatc tcagccgaca gtccatcag caccgcctac    240 ctccagtgga gcagcctgaa ggcctcggac accgccatgt attactgtgc gagaatgcct    300
aattggggct catttgacta ctggggccag ggaaccctgg tcaccgtctc ctca          354
```

<210> SEQ ID NO 54
<211> LENGTH: 445
<212> TYPE: PRT
<213> ORGANISM: Artificial sequence
<220> FEATURE:
<223> OTHER INFORMATION: Synthetic 10G5-2 heavy chain

<400> SEQUENCE: 54

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Val Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Val Arg Met Pro Asn Trp Gly Ser Leu Asp His Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
```

```
                    210                 215                 220
Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                    245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 55
<211> LENGTH: 118
<212> TYPE: PRT
<213> ORGANISM: Artificial sequence
<220> FEATURE:
<223> OTHER INFORMATION: Synthetic 10G5-2 VH

<400> SEQUENCE: 55

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Val Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Val Arg Met Pro Asn Trp Gly Ser Leu Asp His Trp Gly Gln Gly Thr
            100                 105                 110

Leu Val Thr Val Ser Ser
        115
```

<210> SEQ ID NO 56
<211> LENGTH: 1338
<212> TYPE: DNA
<213> ORGANISM: Artificial sequence
<220> FEATURE:
<223> OTHER INFORMATION: Synthetic 10G5-2 heavy chain

<400> SEQUENCE: 56

```
gaggtgcagc tggtgcagtc tggagcagag gtgaaaaagc cggggagtc tctgaagatc      60
tcctgtaagg gttctggata cagctttacc agctactgga tcggctgggt gcgccagatg    120
cccgggaaag gcctggagtg gatgggggtc atctatcctg gtgactctta taccagatac    180
agcccgtcct tccaaggcca ggtcaccatc tcagccgaca gtccatcag caccgcctac    240
ctgcagtgga gcagcctgaa ggcctcggac accgccatgt attactgtgt gagaatgccc    300
aactggggct cactggacca ttggggccag ggaaccctgg tcaccgtctc ctcagcctcc    360
accaagggcc catccgtctt ccccctggcg ccctgctcca ggagcacctc cgagagcaca    420
gccgccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcacgaa gacctacacc    600
tgcaacgtag atcacaagcc cagcaacacc aaggtggaca gagagttga gtccaaatat    660
ggtcccccat gcccaccatg cccagccct gagttcctgg ggggaccatc agtcttcctg    720
ttccccccaa acccaagga cactctcatg atctcccgga cccctgaggt cacgtgcgtg    780
gtggtggacg tgagccagga agaccccgag gtccagttca actggtacgt ggatggcgtg    840
gaggtgcata atgccaagac aaagccgcgg gaggagcagt tcaacagcac gtaccgtgtg    900
gtcagcgtcc tcaccgtcct gcaccaggac tggctgaacg gcaaggagta caagtgcaag    960
gtctccaaca aaggcctccc gtcctccatc gagaaaacca tctccaaagc caaagggcag   1020
ccccgagagc cacaggtgta caccctgccc ccatcccagg aggagatgac caagaaccag   1080
gtcagcctga cctgcctggt caaaggcttc taccccagcg acatcgccgt ggagtgggag   1140
agcaatgggc agccggagaa caactacaag accacgcctc ccgtgctgga ctccgacggc   1200
tccttcttcc tctacagcag gctaaccgtg gacaagagca ggtggcagga ggggaatgtc   1260
ttctcatgct ccgtgatgca tgaggctctg cacaaccact acacacagaa gagcctctcc   1320
ctgtctctgg gtaaatga                                                  1338
```

<210> SEQ ID NO 57
<211> LENGTH: 354
<212> TYPE: DNA
<213> ORGANISM: Artificial sequence
<220> FEATURE:
<223> OTHER INFORMATION: Synthetic 10G5-2 VH

<400> SEQUENCE: 57

```
gaggtgcagc tggtgcagtc tggagcagag gtgaaaaagc cggggagtc tctgaagatc      60
tcctgtaagg gttctggata cagctttacc agctactgga tcggctgggt gcgccagatg    120
cccgggaaag gcctggagtg gatgggggtc atctatcctg gtgactctta taccagatac    180
agcccgtcct tccaaggcca ggtcaccatc tcagccgaca gtccatcag caccgcctac    240
ctgcagtgga gcagcctgaa ggcctcggac accgccatgt attactgtgt gagaatgccc    300
aactggggct cactggacca ttggggccag ggaaccctgg tcaccgtctc ctca           354
```

<210> SEQ ID NO 58

<211> LENGTH: 445
<212> TYPE: PRT
<213> ORGANISM: Artificial sequence
<220> FEATURE:
<223> OTHER INFORMATION: Synthetic 10G5-4,5 heavy chain

<400> SEQUENCE: 58

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Val Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Val Arg Met Pro Asn Trp Gly Ser Leu Asp His Trp Gly Gln Gly Thr
            100                 105                 110

Leu Val Thr Val Ser Ser Ala Ser Ile Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380
```

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 59
<211> LENGTH: 118
<212> TYPE: PRT
<213> ORGANISM: Artificial sequence
<220> FEATURE:
<223> OTHER INFORMATION: Synthetic 10G5-4,5 VH

<400> SEQUENCE: 59

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Val Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Val Arg Met Pro Asn Trp Gly Ser Leu Asp His Trp Gly Gln Gly Thr
            100                 105                 110

Leu Val Thr Val Ser Ser
        115

<210> SEQ ID NO 60
<211> LENGTH: 1338
<212> TYPE: DNA
<213> ORGANISM: Artificial sequence
<220> FEATURE:
<223> OTHER INFORMATION: Synthetic 10G5-4,5 heavy chain

<400> SEQUENCE: 60
gaggtgcagc tggtgcagtc tggagcagag gtgaaaaagc cgggggagtc tctgaagatc         60
tcctgtaagg gttctggata cagctttacc agctactgga tcggctgggt gcgccagatg        120
cccgggaaag cctggagtg atgggggtc atctatcctg gtgactctta taccagatac          180
agcccgtcct tccaaggcca ggtcaccatc tcagccgaca agtccatcag caccgcctac        240
ctgcagtgga gcagcctgaa ggcctcggac accgccatgt attactgtgt gagaatgccc        300
aactggggct cactggacca ttggggccag ggaaccctgg tcaccgtctc ctcagcctcc        360
atcaagggcc catccgtctt ccccctggcg ccctgctcca ggagcacctc cgagagcaca        420
gccgccctgg gctgcctggt caaggactac ttccccgaac cggtgacggt gtcgtggaac        480
tcaggcgccc tgaccagcgg cgtgcacacc ttcccggctg tcctacagtc ctcaggactc        540
tactccctca gcagcgtggt gaccgtgccc tccagcagct tgggcacgaa gacctacacc        600
tgcaacgtag atcacaagcc cagcaacacc aaggtggaca gagagttga gtccaaatat        660

| | | |
|---|---|---|
| ggtcccccat gcccaccatg cccagcacct gagttcctgg ggggaccatc agtcttcctg | 720 | |
| ttccccccaa aacccaagga cactctcatg atctcccgga cccctgaggt cacgtgcgtg | 780 | |
| gtggtggacg tgagccagga agaccccgag gtccagttca actggtacgt ggatggcgtg | 840 | |
| gaggtgcata atgccaagac aaagccgcgg gaggagcagt tcaacagcac gtaccgtgtg | 900 | |
| gtcagcgtcc tcaccgtcct gcaccaggac tggctgaacg gcaaggagta caagtgcaag | 960 | |
| gtctccaaca aaggcctccc gtcctccatc gagaaaacca tctccaaagc caaagggcag | 1020 | |
| ccccgagagc cacaggtgta caccctgccc ccatcccagg aggagatgac caagaaccag | 1080 | |
| gtcagcctga cctgcctggt caaaggcttc taccccagcg acatcgccgt ggagtgggag | 1140 | |
| agcaatgggc agccggagaa caactacaag accacgcctc ccgtgctgga ctccgacggc | 1200 | |
| tccttcttcc tctacagcag gctaaccgtg gacaagagca ggtggcagga ggggaatgtc | 1260 | |
| ttctcatgct ccgtgatgca tgaggctctg cacaaccact acacacagaa gagcctctcc | 1320 | |
| ctgtctctgg gtaaatga | 1338 | |

```
<210> SEQ ID NO 61
<211> LENGTH: 354
<212> TYPE: DNA
<213> ORGANISM: Artificial sequence
<220> FEATURE:
<223> OTHER INFORMATION: Synthetic 10G5-4,5 VH

<400> SEQUENCE: 61
```

| | | |
|---|---|---|
| gaggtgcagc tggtgcagtc tggagcagag gtgaaaaagc ccggggagtc tctgaagatc | 60 | |
| tcctgtaagg gttctggata cagctttacc agctactgga tcggctgggt gcgccagatg | 120 | |
| cccgggaaag gcctggagtg gatgggggtc atctatcctg gtgactctta taccagatac | 180 | |
| agcccgtcct tccaaggcca ggtcaccatc tcagccgaca gtccatcagc accgcctac | 240 | |
| ctgcagtgga gcagcctgaa ggcctcggac accgccatgt attactgtgt gagaatgccc | 300 | |
| aactggggct cactggacca ttggggccag ggaaccctgg tcaccgtctc ctca | 354 | |

```
<210> SEQ ID NO 62
<211> LENGTH: 445
<212> TYPE: PRT
<213> ORGANISM: Artificial sequence
<220> FEATURE:
<223> OTHER INFORMATION: Synthetic 10G5-6,8 heavy chain

<400> SEQUENCE: 62
```

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Val Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Met Pro Asn Trp Gly Ser Leu Asp His Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
         130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                 165                 170                 175

Ser Ser Gly Leu Tyr Ser Leu Ser Ser Val Val Thr Val Pro Ser Ser
             180                 185                 190

Ser Leu Gly Thr Lys Thr Tyr Thr Cys Asn Val Asp His Lys Pro Ser
         195                 200                 205

Asn Thr Lys Val Asp Lys Arg Val Glu Ser Lys Tyr Gly Pro Pro Cys
     210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                 245                 250                 255

Val Thr Cys Val Val Val Asp Val Ser Gln Glu Asp Pro Glu Val Gln
             260                 265                 270

Phe Asn Trp Tyr Val Asp Gly Val Glu Val His Asn Ala Lys Thr Lys
         275                 280                 285

Pro Arg Glu Glu Gln Phe Asn Ser Thr Tyr Arg Val Val Ser Val Leu
     290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                 325                 330                 335

Ala Lys Gly Gln Pro Arg Glu Pro Gln Val Tyr Thr Leu Pro Pro Ser
             340                 345                 350

Gln Glu Glu Met Thr Lys Asn Gln Val Ser Leu Thr Cys Leu Val Lys
         355                 360                 365

Gly Phe Tyr Pro Ser Asp Ile Ala Val Glu Trp Glu Ser Asn Gly Gln
     370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                 405                 410                 415

Glu Gly Asn Val Phe Ser Cys Ser Val Met His Glu Ala Leu His Asn
             420                 425                 430

His Tyr Thr Gln Lys Ser Leu Ser Leu Ser Leu Gly Lys
         435                 440                 445

<210> SEQ ID NO 63
<211> LENGTH: 118
<212> TYPE: PRT
<213> ORGANISM: Artificial sequence
<220> FEATURE:
<223> OTHER INFORMATION: Synthetic 10G5-6,8 VH

<400> SEQUENCE: 63

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
         35                  40                  45

Gly Val Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Met Pro Asn Trp Gly Ser Leu Asp His Trp Gly Gln Gly Thr
            100                 105                 110

Leu Val Thr Val Ser Ser
        115

<210> SEQ ID NO 64
<211> LENGTH: 1338
<212> TYPE: DNA
<213> ORGANISM: Artificial sequence
<220> FEATURE:
<223> OTHER INFORMATION: Synthetic 10G5-6,8 heavy chain

<400> SEQUENCE: 64

```
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatggggtc atctatcctg gtgactctta taccagatac     180
agcccgtcct ccaaggcca gtcaccatc tcagccgaca gtccatcag caccgcctac       240
ctgcagtgga gcagcctgaa ggcctcggac accgccatgt attactgtgc gagaatgccc     300
aactggggct cacttgacca ttgggggcag ggaaccctgg tcaccgtctc ctcagcctcc     360
accaagggcc catccgtctt ccccctggcg ccctgctcca ggagcacctc cgagagcaca     420
gccgccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct tgggcacgaa gacctacacc     600
tgcaacgtag atcacaagcc cagcaacacc aaggtggaca gagagttga gtccaaatat     660
ggtccccat gccaccatg cccagcacct gagttcctgg ggggaccatc agtcttcctg       720
ttccccccaa aacccaagga cactctcatg atctcccgga cccctgaggt cacgtgcgtg     780
gtggtggacg tgagccagga agaccccgag gtccagttca actggtacgt ggatggcgtg     840
gaggtgcata atgccaagac aaagccgcgg gaggagcagt tcaacagcac gtaccgtgtg     900
gtcagcgtcc tcaccgtcct gcaccaggac tggctgaacg gcaaggagta caagtgcaag     960
gtctccaaca aaggcctccc gtcctccatc gagaaaacca tctccaaagc caaagggcag    1020
ccccgagagc cacaggtgta caccctgccc ccatcccagg aggagatgac caagaaccag    1080
gtcagcctga cctgcctggt caaaggcttc taccccagcg acatcgccgt ggagtgggag    1140
agcaatgggc agccggagaa caactacaag accacgcctc ccgtgctgga ctccgacggc    1200
tccttcttcc tctacagcag gctaaccgtg gacaagagca ggtggcagga ggggaatgtc    1260
ttctcatgct ccgtgatgca tgaggctctg cacaaccact acacacagaa gagcctctcc    1320
ctgtctctgg gtaaatga                                                  1338
```

<210> SEQ ID NO 65
<211> LENGTH: 354
<212> TYPE: DNA
<213> ORGANISM: Artificial sequence
<220> FEATURE:
<223> OTHER INFORMATION: Synthetic 10G5-6,8 VH -continued

```
<400> SEQUENCE: 65
gaggtgcagc tggtgcagtc tggagcagag gtgaaaaagc cggggagtc tctgaagatc        60 tcctgtaagg gttctggata cagctttacc agctactgga tcggctgggt gcgccagatg      120
cccgggaaag gcctggagtg gatggggggtc atctatcctg gtgactctta taccagatac     180
agcccgtcct tccaaggcca ggtcaccatc tcagccgaca gtccatcag caccgcctac       240 ctgcagtgga gcagcctgaa ggcctcggac accgccatgt attactgtgc gagaatgccc      300 aactgggggct cacttgacca ttggggccag ggaaccctgg tcaccgtctc ctca            354

<210> SEQ ID NO 66
<211> LENGTH: 445
<212> TYPE: PRT
<213> ORGANISM: Artificial sequence
<220> FEATURE:
<223> OTHER INFORMATION: Synthetic 10G5-7 heavy chain

<400> SEQUENCE: 66
```

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Val Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Met Pro Asn Trp Gly Ser Leu Asp His Trp Gly Gln Gly Thr
            100                 105                 110

Leu Val Thr Val Ser Ser Ala Ser Ile Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

```
Pro Arg Glu Glu Gln Phe Asn Ser Thr Tyr Arg Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
                325                 330                 335
Ala Lys Gly Gln Pro Arg Glu Pro Gln Val Tyr Thr Leu Pro Pro Ser
                340                 345                 350
Gln Glu Glu Met Thr Lys Asn Gln Val Ser Leu Thr Cys Leu Val Lys
                355                 360                 365
Gly Phe Tyr Pro Ser Asp Ile Ala Val Glu Trp Glu Ser Asn Gly Gln
        370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
                420                 425                 430
His Tyr Thr Gln Lys Ser Leu Ser Leu Ser Leu Gly Lys
        435                 440                 445

<210> SEQ ID NO 67
<211> LENGTH: 118
<212> TYPE: PRT
<213> ORGANISM: Artificial sequence
<220> FEATURE:
<223> OTHER INFORMATION: Synthetic 10G5-7 VH

<400> SEQUENCE: 67

Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Ser Tyr
                20                  25                  30
Trp Ile Gly Trp Val Arg Gln Met Pro Gly Lys Gly Leu Glu Trp Met
            35                  40                  45
Gly Val Ile Tyr Pro Gly Asp Ser Tyr Thr Arg Tyr Ser Pro Ser Phe
        50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Met Pro Asn Trp Gly Ser Leu Asp His Trp Gly Gln Gly Thr
                100                 105                 110
Leu Val Thr Val Ser Ser
        115

<210> SEQ ID NO 68
<211> LENGTH: 1338
<212> TYPE: DNA
<213> ORGANISM: Artificial sequence
<220> FEATURE:
<223> OTHER INFORMATION: Synthetic 10G5-7 heavy chain

<400> SEQUENCE: 68
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatgggggtc atctatcctg gtgactctta taccagatac     180
```

```
agcccgtcct tccaaggcca ggtcaccatc tcagccgaca agtccatcag caccgcctac      240
ctgcagtgga gcagcctgaa ggcctcggac accgccatgt attactgtgc gagaatgccc      300
aactggggct cacttgacca ttggggccag gaaccctgg  tcaccgtctc ctcagcctcc      360
atcaagggcc catccgtctt ccccctggcg ccctgctcca ggagcacctc cgagagcaca      420
gccgccctgg gctgcctggt caaggactac ttccccgaac cggtgacggt gtcgtggaac      480
tcaggcgccc tgaccagcgg cgtgcacacc ttcccggctg tcctacagtc ctcaggactc      540
tactccctca gcagcgtggt gaccgtgccc tccagcagct gggcacgaa  gacctacacc      600 tgcaacgtag atcacaagcc cagcaacacc aaggtggaca gagagttga  gtccaaatat      660 ggtccccat  gccaccatg  cccagcacct gagttcctgg ggggaccatc agtcttcctg      720
ttccccccaa aacccaagga cactctcatg atctcccgga cccctgaggt cacgtgcgtg      780
gtggtggacg tgagccagga agaccccgag gtccagttca actggtacgt ggatggcgtg      840
gaggtgcata atgccaagac aaagccgcgg gaggagcagt tcaacagcac gtaccgtgtg      900
gtcagcgtcc tcaccgtcct gcaccaggac tggctgaacg gcaaggagta caagtgcaag      960
gtctccaaca aaggcctccc gtcctccatc gagaaaacca tctccaaagc caaagggcag     1020
ccccgagagc cacaggtgta caccctgccc ccatcccagg aggagatgac caagaaccag     1080
gtcagcctga cctgcctggt caaaggcttc taccccagcg acatcgccgt ggagtgggag     1140
agcaatgggc agccggagaa caactacaag accacgcctc ccgtgctgga ctccgacggc     1200
tccttcttcc tctacagcag gctaaccgtg gacaagagca ggtggcagga ggggaatgtc     1260
ttctcatgct ccgtgatgca tgaggctctg cacaaccact acacacagaa gagcctctcc     1320
ctgtctctgg gtaaatga                                                    1338

<210> SEQ ID NO 69
<211> LENGTH: 354
<212> TYPE: DNA
<213> ORGANISM: Artificial sequence
<220> FEATURE:
<223> OTHER INFORMATION: Synthetic 10G5-7 VH

<400> SEQUENCE: 69
gaggtgcagc tggtgcagtc tggagcagag gtgaaaaagc ccggggagtc tctgaagatc       60
tcctgtaagg gttctggata cagctttacc agctactgga tcggctgggt gcgccagatg      120
cccgggaaag gcctggagtg gatgggggtc atctatcctg gtgactctta taccagatac      180
agcccgtcct tccaaggcca ggtcaccatc tcagccgaca agtccatcag caccgcctac      240
ctgcagtgga gcagcctgaa ggcctcggac accgccatgt attactgtgc gagaatgccc      300
aactggggct cacttgacca ttggggccag gaaccctgg  tcaccgtctc ctca            354

<210> SEQ ID NO 70
<211> LENGTH: 211
<212> TYPE: PRT
<213> ORGANISM: Artificial sequence
<220> FEATURE:
<223> OTHER INFORMATION: Synthetic 10G5-1,2,4,6,7 light chain

<400> SEQUENCE: 70

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30
```

```
Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                      55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ala Ser Phe Gly
                 85                  90                  95

Gln Gly Thr Lys Val Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
            115                 120                 125

Val Val Cys Leu Leu Asn Asn Phe Tyr Pro Arg Glu Ala Lys Val Gln
130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
            195                 200                 205

Gly Glu Cys
    210

<210> SEQ ID NO 71
<211> LENGTH: 104
<212> TYPE: PRT
<213> ORGANISM: Artificial sequence
<220> FEATURE:
<223> OTHER INFORMATION: Synthetic 10G5-1,2,4,6,7 VL

<400> SEQUENCE: 71

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Ile Ser Ser Ser
             20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                      55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ala Ser Phe Gly
                 85                  90                  95

Gln Gly Thr Lys Val Glu Ile Lys
            100

<210> SEQ ID NO 72
<211> LENGTH: 636
<212> TYPE: DNA
<213> ORGANISM: Artificial sequence
<220> FEATURE:
<223> OTHER INFORMATION: Synthetic 10G5-1,2,4,6,7 light chain

<400> SEQUENCE: 72
gaaattgtgt tgacgcagtc tccaggcacc ctgtctttgt ctccagggga aagagccacc    60
```

```
ctctcctgca gggccagtca gagtattagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatgctt cgttcggcca agggaccaag    300
gtggaaatca aacgtacggt ggctgcacca tctgtcttca tcttcccgcc atctgatgag    360
cagttgaaat ctggaactgc ctctgttgtg tgcctgctga ataacttcta tcccagagag    420
gccaaagtac agtggaaggt ggataacgcc ctccaatcgg gtaactccca ggagagtgtc    480
acagagcagg acagcaagga cagcacctac agcctcagca gcaccctgac gctgagcaaa    540
gcagactacg agaaacacaa agtctacgcc tgcgaagtca cccatcaggg cctgagctcg    600
cccgtcacaa agagcttcaa caggggagag tgttag                              636
```

<210> SEQ ID NO 73
<211> LENGTH: 312
<212> TYPE: DNA
<213> ORGANISM: Artificial sequence
<220> FEATURE:
<223> OTHER INFORMATION: Synthetic 10G5-1,2,4,6,7 VL

<400> SEQUENCE: 73

```
gaaattgtgt tgacgcagtc tccaggcacc ctgtctttgt ctccagggga aagagccacc     60
ctctcctgca gggccagtca gagtattagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatgctt cgttcggcca agggaccaag    300
gtggaaatca aa                                                        312
```

<210> SEQ ID NO 74
<211> LENGTH: 211
<212> TYPE: PRT
<213> ORGANISM: Artificial sequence
<220> FEATURE:
<223> OTHER INFORMATION: Synthetic 10G5-3 light chain

<400> SEQUENCE: 74

```
Glu Ile Val Leu Thr Gln Ser Pro Gly Thr Leu Ser Leu Ser Pro Gly
1               5                  10                  15

Glu Arg Ala Thr Leu Ser Cys Arg Ala Ser Gln Ser Ile Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Glu Ala Phe Gly
                85                  90                  95

Gln Gly Thr Lys Val Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140
```

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
            165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
            195                 200                 205

Gly Glu Cys
    210

<210> SEQ ID NO 75
<211> LENGTH: 104
<212> TYPE: PRT
<213> ORGANISM: Artificial sequence
<220> FEATURE:
<223> OTHER INFORMATION: Synthetic 10G5-3 VL

<400> SEQUENCE: 75

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Glu Ala Phe Gly
                85                  90                  95

Gln Gly Thr Lys Val Glu Ile Lys
            100

<210> SEQ ID NO 76
<211> LENGTH: 636
<212> TYPE: DNA
<213> ORGANISM: Artificial sequence
<220> FEATURE:
<223> OTHER INFORMATION: Synthetic 10G5-3 light chain

<400> SEQUENCE: 76
gaaattgtgt tgacgcagtc tccaggcacc ctgtctttgt ctccagggga aagagccacc      60
ctctcctgca gggccagtca gagtattagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatgagg cgttcggcca agggaccaag     300
gtggaaatca aacgtacggt ggctgcacca tctgtcttca tcttcccgcc atctgatgag     360
cagttgaaat ctggaactgc ctctgttgtg tgcctgctga ataacttcta tcccagagag     420
gccaaagtac agtggaaggt ggataacgcc ctccaatcgg gtaactccca ggagagtgtc     480
acagagcagg acagcaagga cagcacctac agcctcagca gcaccctgac gctgagcaaa     540
gcagactacg agaaacacaa agtctacgcc tgcgaagtca cccatcaggg cctgagctcg     600
cccgtcacaa agagcttcaa caggggagag tgttag                               636

<210> SEQ ID NO 77
<211> LENGTH: 312
<212> TYPE: DNA
<213> ORGANISM: Artificial sequence
<220> FEATURE:
<223> OTHER INFORMATION: Synthetic 10G5-3 VL

<400> SEQUENCE: 77

```
gaaattgtgt tgacgcagtc tccaggcacc ctgtctttgt ctccagggga aagagccacc    60
ctctcctgca gggccagtca gagtattagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatgagg cgttcggcca agggaccaag   300
gtggaaatca aa                                                       312
```

<210> SEQ ID NO 78
<211> LENGTH: 211
<212> TYPE: PRT
<213> ORGANISM: Artificial sequence
<220> FEATURE:
<223> OTHER INFORMATION: Synthetic 10G5-5,8 light chain

<400> SEQUENCE: 78

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Glu Thr Phe Gly
                85                  90                  95

Gln Gly Thr Lys Val Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210
```

<210> SEQ ID NO 79
<211> LENGTH: 104
<212> TYPE: PRT
<213> ORGANISM: Artificial sequence
<220> FEATURE:

<223> OTHER INFORMATION: Synthetic 10G5-5,8 VL

<400> SEQUENCE: 79

| Glu | Ile | Val | Leu | Thr | Gln | Ser | Pro | Gly | Thr | Leu | Ser | Leu | Ser | Pro | Gly |
|---|---|---|---|---|---|---|---|---|---|---|---|---|---|---|---|
| 1 | | | | 5 | | | | | 10 | | | | | 15 | |

| Glu | Arg | Ala | Thr | Leu | Ser | Cys | Arg | Ala | Ser | Gln | Ser | Ile | Ser | Ser | Ser |
|---|---|---|---|---|---|---|---|---|---|---|---|---|---|---|---|
| | | | 20 | | | | | 25 | | | | | 30 | | |

| Tyr | Leu | Ala | Trp | Tyr | Gln | Gln | Lys | Pro | Gly | Gln | Ala | Pro | Arg | Leu | Leu |
|---|---|---|---|---|---|---|---|---|---|---|---|---|---|---|---|
| | | 35 | | | | | 40 | | | | | 45 | | | |

| Ile | Tyr | Gly | Ala | Ser | Ser | Arg | Ala | Thr | Gly | Ile | Pro | Asp | Arg | Phe | Ser |
|---|---|---|---|---|---|---|---|---|---|---|---|---|---|---|---|
| | 50 | | | | | 55 | | | | | 60 | | | | |

| Gly | Ser | Gly | Ser | Gly | Thr | Asp | Phe | Thr | Leu | Thr | Ile | Ser | Arg | Leu | Glu |
|---|---|---|---|---|---|---|---|---|---|---|---|---|---|---|---|
| 65 | | | | | 70 | | | | | 75 | | | | | 80 |

| Pro | Glu | Asp | Phe | Ala | Val | Tyr | Tyr | Cys | Gln | Gln | Tyr | Glu | Thr | Phe | Gly |
|---|---|---|---|---|---|---|---|---|---|---|---|---|---|---|---|
| | | | | 85 | | | | | 90 | | | | | 95 | |

| Gln | Gly | Thr | Lys | Val | Glu | Ile | Lys |
|---|---|---|---|---|---|---|---|
| | | | 100 | | | | |

<210> SEQ ID NO 80
<211> LENGTH: 636
<212> TYPE: DNA
<213> ORGANISM: Artificial sequence
<220> FEATURE:
<223> OTHER INFORMATION: Synthetic 10G5-5,8 light chain

<400> SEQUENCE: 80

```
gaaattgtgt tgacgcagtc tccaggcacc ctgtctttgt ctccagggga aagagccacc      60
ctctcctgca gggccagtca gagtattagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatgaga cgttcggcca agggaccaag     300
gtggaaatca aacgtacggt ggctgcacca tctgtcttca tcttcccgcc atctgatgag     360
cagttgaaat ctggaactgc ctctgttgtg tgcctgctga ataacttcta tcccagagag     420
gccaaagtac agtggaaggt ggataacgcc ctccaatcgg gtaactccca ggagagtgtc     480
acagagcagg acagcaagga cagcacctac agcctcagca gcaccctgac gctgagcaaa     540
gcagactacg agaaacacaa agtctacgcc tgcgaagtca cccatcaggg cctgagctcg     600
cccgtcacaa agagcttcaa caggggagag tgttag                              636
```

<210> SEQ ID NO 81
<211> LENGTH: 312
<212> TYPE: DNA
<213> ORGANISM: Artificial sequence
<220> FEATURE:
<223> OTHER INFORMATION: Synthetic 10G5-5,8 VL

<400> SEQUENCE: 81

```
gaaattgtgt tgacgcagtc tccaggcacc ctgtctttgt ctccagggga aagagccacc      60
ctctcctgca gggccagtca gagtattagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatgaga cgttcggcca agggaccaag     300
gtggaaatca aa                                                         312
```

<210> SEQ ID NO 82
<211> LENGTH: 10
<212> TYPE: PRT
<213> ORGANISM: Artificial sequence
<220> FEATURE:
<223> OTHER INFORMATION: Synthetic 10G5 VH CDR1

<400> SEQUENCE: 82

Gly Tyr Ser Phe Thr Ser Tyr Trp Ile Gly
1               5                   10

<210> SEQ ID NO 83
<211> LENGTH: 10
<212> TYPE: PRT
<213> ORGANISM: Artificial sequence
<220> FEATURE:
<223> OTHER INFORMATION: Synthetic 10G5 VH CDR2

<400> SEQUENCE: 83

Val Ile Tyr Pro Gly Asp Ser Tyr Thr Arg
1               5                   10

<210> SEQ ID NO 84
<211> LENGTH: 12
<212> TYPE: PRT
<213> ORGANISM: Artificial sequence
<220> FEATURE:
<223> OTHER INFORMATION: Synthetic 10G5 VL CDR1

<400> SEQUENCE: 84

Arg Ala Ser Gln Ser Ile Ser Ser Ser Tyr Leu Ala
1               5                   10

<210> SEQ ID NO 85
<211> LENGTH: 7
<212> TYPE: PRT
<213> ORGANISM: Artificial sequence
<220> FEATURE:
<223> OTHER INFORMATION: Synthetic 10G5 VL CDR2

<400> SEQUENCE: 85

Gly Ala Ser Ser Arg Ala Thr
1               5

<210> SEQ ID NO 86
<211> LENGTH: 487
<212> TYPE: PRT
<213> ORGANISM: Artificial sequence
<220> FEATURE:
<223> OTHER INFORMATION: Synthetic pFAB3D-10G5H construct

<400> SEQUENCE: 86

Met Lys Lys Thr Ala Ile Ala Ile Ala Val Ala Leu Ala Gly Phe Ala
1               5                   10                  15

Thr Val Ala Gln Ala Ala Leu Glu Val Gln Leu Val Gln Ser Gly
            20                  25                  30

Ala Glu Val Lys Lys Pro Gly Glu Ser Leu Lys Ile Ser Cys Lys Gly
        35                  40                  45

Ser Gly Tyr Ser Phe Thr Ser Tyr Trp Ile Gly Trp Val Arg Gln Met
    50                  55                  60

Pro Gly Lys Gly Leu Glu Trp Met Gly Val Ile Tyr Pro Gly Asp Ser
65                  70                  75                  80

Tyr Thr Arg Tyr Ser Pro Ser Phe Gln Gly Gln Val Thr Ile Ser Ala
                85                  90                  95

Asp Lys Ser Ile Ser Thr Ala Tyr Leu Gln Trp Ser Ser Leu Lys Ala
            100                 105                 110

Ser Asp Thr Ala Met Tyr Tyr Cys Ala Arg Phe Pro Asn Trp Gly Ser
            115                 120                 125

Phe Asp Tyr Trp Gly Gln Gly Thr Leu Val Thr Val Ser Ser Ala Ser
            130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
            195                 200                 205

Ser Val Val Thr Val Pro Ser Ser Ser Leu Gly Thr Gln Thr Tyr Ile
        210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Thr
                245                 250                 255

Ser Gly His His His His His His Gly Gly Glu Gln Lys Leu Ile Ser
            260                 265                 270

Glu Glu Asp Leu Gly Gly Pro Phe Val Cys Glu Tyr Gln Gly Gln Ser
            275                 280                 285

Ser Asp Leu Pro Gln Pro Pro Val Asn Ala Gly Gly Gly Ser Gly Gly
        290                 295                 300

Gly Ser Gly Gly Gly Ser Glu Gly Gly Gly Ser Glu Gly Gly Gly Ser
305                 310                 315                 320

Glu Gly Gly Gly Ser Glu Gly Gly Ser Gly Gly Gly Ser Gly Ser
                325                 330                 335

Gly Asp Phe Asp Tyr Glu Lys Met Ala Asn Ala Asn Lys Gly Ala Met
            340                 345                 350

Thr Glu Asn Ala Asp Glu Asn Ala Leu Gln Ser Asp Ala Lys Gly Lys
            355                 360                 365

Leu Asp Ser Val Ala Thr Asp Tyr Gly Ala Ala Ile Asp Gly Phe Ile
        370                 375                 380

Gly Asp Val Ser Gly Leu Ala Asn Gly Asn Gly Ala Thr Gly Asp Phe
385                 390                 395                 400

Ala Gly Ser Asn Ser Gln Met Ala Gln Val Gly Asp Gly Asp Asn Ser
                405                 410                 415

Pro Leu Met Asn Asn Phe Arg Gln Tyr Leu Pro Ser Leu Pro Gln Ser
            420                 425                 430

Val Glu Cys Arg Pro Tyr Val Phe Gly Ala Gly Lys Pro Tyr Glu Phe
            435                 440                 445

Ser Ile Asp Cys Asp Lys Ile Asn Leu Phe Arg Gly Val Phe Ala Phe
        450                 455                 460

Leu Leu Tyr Val Ala Thr Phe Met Tyr Val Phe Ser Thr Phe Ala Asn
465                 470                 475                 480

Ile Leu Arg Asn Lys Glu Ser
                485

<210> SEQ ID NO 87
<211> LENGTH: 235

<212> TYPE: PRT
<213> ORGANISM: Artificial sequence
<220> FEATURE:
<223> OTHER INFORMATION: Synthetic pFAB3D-10G5L construct

<400> SEQUENCE: 87

```
Met Lys Tyr Leu Leu Pro Thr Ala Ala Ala Gly Leu Leu Leu Leu Ala
1               5                   10                  15
Ala Gln Pro Ala Met Ala Ser Arg Glu Ile Val Leu Thr Gln Ser Pro
            20                  25                  30
Gly Thr Leu Ser Leu Ser Pro Gly Glu Arg Ala Thr Leu Ser Cys Arg
        35                  40                  45
Ala Ser Gln Ser Ile Ser Ser Ser Tyr Leu Ala Trp Tyr Gln Gln Lys
    50                  55                  60
Pro Gly Gln Ala Pro Arg Leu Leu Ile Tyr Gly Ala Ser Ser Arg Ala
65                  70                  75                  80
Thr Gly Ile Pro Asp Arg Phe Ser Gly Ser Gly Ser Gly Thr Asp Phe
                85                  90                  95
Thr Leu Thr Ile Ser Arg Leu Glu Pro Glu Asp Phe Ala Val Tyr Tyr
            100                 105                 110
Cys Gln Gln Tyr Glu Thr Phe Gly Gln Gly Thr Lys Val Glu Ile Lys
        115                 120                 125
Arg Thr Val Ala Ala Pro Ser Val Phe Ile Phe Pro Pro Ser Asp Glu
    130                 135                 140
Gln Leu Lys Ser Gly Thr Ala Ser Val Val Cys Leu Leu Asn Asn Phe
145                 150                 155                 160
Tyr Pro Arg Glu Ala Lys Val Gln Trp Lys Val Asp Asn Ala Leu Gln
                165                 170                 175
Ser Gly Asn Ser Gln Glu Ser Val Thr Glu Gln Asp Ser Lys Asp Ser
            180                 185                 190
Thr Tyr Ser Leu Ser Ser Thr Leu Thr Leu Ser Lys Ala Asp Tyr Glu
        195                 200                 205
Lys His Lys Val Tyr Ala Cys Glu Val Thr His Gln Gly Leu Ser Ser
    210                 215                 220
Pro Val Thr Lys Ser Phe Asn Arg Gly Glu Cys
225                 230                 235
```

<210> SEQ ID NO 88
<211> LENGTH: 100
<212> TYPE: DNA
<213> ORGANISM: Artificial sequence
<220> FEATURE:
<223> OTHER INFORMATION: Synthetic PCR primer

<400> SEQUENCE: 88
atcgaagctt gccgccacca tgagtgtgcc cactcaggtc ctggggttgc tgctgctgtg     60
gcttacagat gccagatgtg aaattgtgtt gacgcagtct                          100

<210> SEQ ID NO 89
<211> LENGTH: 22
<212> TYPE: DNA
<213> ORGANISM: Artificial sequence
<220> FEATURE:
<223> OTHER INFORMATION: Synthetic PCR primer

<400> SEQUENCE: 89
ccaccgtacg tttgatttcc ac                                              22

<210> SEQ ID NO 90
<211> LENGTH: 97
<212> TYPE: DNA
<213> ORGANISM: Artificial sequence
<220> FEATURE:
<223> OTHER INFORMATION: Synthetic PCR primer

<400> SEQUENCE: 90

```
actgaagctt gccgccacca tggaatggag ctgggtcttt ctcttcttcc tgtcagtaac      60
tacaggtgtc cactccgagg tgcagctggt gcagtct                              97
```

<210> SEQ ID NO 91
<211> LENGTH: 24
<212> TYPE: DNA
<213> ORGANISM: Artificial sequence
<220> FEATURE:
<223> OTHER INFORMATION: Synthetic PCR primer

<400> SEQUENCE: 91

```
accgatgggc ccttggtgga ggct                                            24
```

<210> SEQ ID NO 92
<211> LENGTH: 326
<212> TYPE: PRT
<213> ORGANISM: Artificial sequence
<220> FEATURE:
<223> OTHER INFORMATION: Synthetic Fc domain of IgG2m4

<400> SEQUENCE: 92

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240
```

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 93
<211> LENGTH: 978
<212> TYPE: DNA
<213> ORGANISM: Artificial sequence
<220> FEATURE:
<223> OTHER INFORMATION: Synthetic constant of IGG2M4

<400> SEQUENCE: 93
gcctccacca agggcccatc cgtcttcccc ctggcgccct gctccaggag cacctccgag     60
agcacagccg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgacctcca gcaactttgg cacgcagacc    240
tacacctgca acgtagatca caagcccagc aacaccaagg tggacaagac agttgagcgg    300
aaatgctgcg tggagtgccc accatgccca gcacctccag tggccggacc atcagtcttc    360
ctgttccccc caaaacccaa ggacactctc atgatctccc ggacccctga ggtcacgtgc    420
gtggtggtgg acgtgagcca ggaagacccc gaggtccagt tcaactggta cgtggatggc    480
gtggaggtgc ataatgccaa gacaaagccg cgggaggagc agttcaacag cacgttccgt    540
gtggtcagcg tcctcaccgt cctgcaccag gactggctga acggcaagga gtacaagtgc    600
aaggtctcca acaaaggcct cccgtcctcc atcgagaaaa ccatctccaa aaccaaaggg    660
cagccccgag agccacaggt gtacaccctg cccccatccc gggaggagat gaccaagaac    720
caggtcagcc tgacctgcct ggtcaaaggc ttctacccca gcgacatcgc cgtggagtgg    780
gagagcaatg gcagccggga gaacaactac aagaccacgc ctcccatgct ggactccgac    840
ggctccttct cctctacag caagctaacc gtggacaaga gcaggtggca gcagggaat    900
gtcttctcat gctccgtgat gcatgaggct ctgcacaacc actacacaca gaagagcctc    960
tccctgtctc ctggtaaa                                                  978

<210> SEQ ID NO 94
<211> LENGTH: 444
<212> TYPE: PRT
<213> ORGANISM: Artificial sequence
<220> FEATURE:
<223> OTHER INFORMATION: Synthetic 10G5-6 heavy chain IGG2M4

<400> SEQUENCE: 94

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

-continued

```
Trp Ile Gly Trp Val Arg Gln Met Pro Gly Lys Gly Leu Glu Trp Met
         35                  40                  45
Gly Val Ile Tyr Pro Gly Asp Ser Tyr Thr Arg Tyr Ser Pro Ser Phe
 50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Met Pro Asn Trp Gly Ser Leu Asp His Trp Gly Gln Gly Thr
             100                 105                 110
Leu Val Thr Val Ser Ser Ala Ser Thr Lys Gly Pro Ser Val Phe Pro
         115                 120                 125
Leu Ala Pro Cys Ser Arg Ser Thr Ser Glu Ser Thr Ala Ala Leu Gly
 130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                 165                 170                 175
Ser Ser Gly Leu Tyr Ser Leu Ser Ser Val Val Thr Val Thr Ser Ser
             180                 185                 190
Asn Phe Gly Thr Gln Thr Tyr Thr Cys Asn Val Asp His Lys Pro Ser
         195                 200                 205
Asn Thr Lys Val Asp Lys Thr Val Glu Arg Lys Cys Cys Val Glu Cys
 210                 215                 220
Pro Pro Cys Pro Ala Pro Pro Val Ala Gly Pro Ser Val Phe Leu Phe
225                 230                 235                 240
Pro Pro Lys Pro Lys Asp Thr Leu Met Ile Ser Arg Thr Pro Glu Val
                 245                 250                 255
Thr Cys Val Val Val Asp Val Ser Gln Glu Asp Pro Glu Val Gln Phe
             260                 265                 270
Asn Trp Tyr Val Asp Gly Val Glu Val His Asn Ala Lys Thr Lys Pro
         275                 280                 285
Arg Glu Glu Gln Phe Asn Ser Thr Phe Arg Val Val Ser Val Leu Thr
 290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Thr
                 325                 330                 335
Lys Gly Gln Pro Arg Glu Pro Gln Val Tyr Thr Leu Pro Pro Ser Arg
             340                 345                 350
Glu Glu Met Thr Lys Asn Gln Val Ser Leu Thr Cys Leu Val Lys Gly
         355                 360                 365
Phe Tyr Pro Ser Asp Ile Ala Val Glu Trp Glu Ser Asn Gly Gln Pro
 370                 375                 380
Glu Asn Asn Tyr Lys Thr Thr Pro Pro Met Leu Asp Ser Asp Gly Ser
385                 390                 395                 400
Phe Phe Leu Tyr Ser Lys Leu Thr Val Asp Lys Ser Arg Trp Gln Gln
                 405                 410                 415
Gly Asn Val Phe Ser Cys Ser Val Met His Glu Ala Leu His Asn His
             420                 425                 430
Tyr Thr Gln Lys Ser Leu Ser Leu Ser Pro Gly Lys
         435                 440
```

<210> SEQ ID NO 95
<211> LENGTH: 1332
<212> TYPE: DNA
<213> ORGANISM: Artificial sequence
<220> FEATURE:
<223> OTHER INFORMATION: Synthetic 10G5-6 heavy chain IGG2M4

<400> SEQUENCE: 95

```
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatgggggtc atctatcctg gtgactctta taccagatac     180
agcccgtcct tccaaggcca ggtcaccatc tcagccgaca gtccatcag caccgcctac      240
ctgcagtgga gcagcctgaa ggcctcggac accgccatgt attactgtgc gagaatgccc     300
aactggggct cacttgacca ttggggccag ggaaccctgg tcaccgtctc ctcagcctcc     360
accaagggcc catccgtctt ccccctggcg ccctgctcca ggagcacctc cgagagcaca     420
gccgccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgacc tccagcaact ttggcacgca gacctacacc     600
tgcaacgtag atcacaagcc cagcaacacc aaggtggaca agacagttga gcggaaatgc     660
tgcgtggagt gccaccatg cccagcacct ccagtggccg gaccatcagt cttcctgttc     720
cccccaaaac ccaaggacac tctcatgatc tcccggaccc ctgaggtcac gtgcgtggtg     780
gtggacgtga gccaggaaga ccccgaggtc cagttcaact ggtacgtgga tggcgtggag     840
gtgcataatg ccaagacaaa gccgcgggag gagcagttca acagcacgtt ccgtgtggtc     900
agcgtcctca ccgtcctgca ccaggactgg ctgaacggca aggagtacaa gtgcaaggtc     960
tccaacaaag gcctcccgtc ctccatcgag aaaaccatct ccaaaaccaa agggcagccc    1020
cgagagccac aggtgtacac cctgccccca tcccgggagg agatgaccaa gaaccaggtc    1080
agcctgacct gcctggtcaa aggcttctac cccagcgaca tcgccgtgga gtgggagagc    1140
aatgggcagc cggagaacaa ctacaagacc acgcctccca tgctggactc cgacggctcc    1200
ttcttcctct acagcaagct aaccgtggac aagagcaggt ggcagcaggg gaatgtcttc    1260
tcatgctccg tgatgcatga ggctctgcac aaccactaca cacagaagag cctctccctg    1320
tctcctggta aa                                                        1332
```

<210> SEQ ID NO 96
<211> LENGTH: 444
<212> TYPE: PRT
<213> ORGANISM: Artificial sequence
<220> FEATURE:
<223> OTHER INFORMATION: Synthetic 10G5H6 heavy chain IGG2M4

<400> SEQUENCE: 96

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Val Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80
```

-continued

```
Leu Gln Trp Ser Ser Leu Lys Ala Ser Asp Thr Ala Met Tyr Tyr Cys
                85                  90                  95

Ala Arg Met Pro Asn Trp Gly Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Thr Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440
```

<210> SEQ ID NO 97
<211> LENGTH: 336
<212> TYPE: PRT
<213> ORGANISM: Artificial sequence
<220> FEATURE:
<223> OTHER INFORMATION: Synthetic construct containing Fc domain of IgG1

<400> SEQUENCE: 97

```
Leu Val Thr Val Ser Ser Ala Ser Thr Lys Gly Pro Ser Val Phe Pro
1               5                   10                  15

Leu Ala Pro Ser Ser Lys Ser Thr Ser Gly Gly Thr Ala Ala Leu Gly
            20                  25                  30

Cys Leu Val Lys Asp Tyr Phe Pro Glu Pro Val Thr Val Ser Trp Asn
        35                  40                  45

Ser Gly Ala Leu Thr Ser Gly Val His Thr Phe Pro Ala Val Leu Gln
    50                  55                  60

Ser Ser Gly Leu Tyr Ser Leu Ser Ser Val Val Thr Val Pro Ser Ser
65                  70                  75                  80

Ser Leu Gly Thr Gln Thr Tyr Ile Cys Asn Val Asn His Lys Pro Ser
                85                  90                  95

Asn Thr Lys Val Asp Lys Lys Ala Glu Pro Lys Ser Cys Asp Lys Thr
            100                 105                 110

His Thr Cys Pro Pro Cys Pro Ala Pro Glu Leu Leu Gly Gly Pro Ser
        115                 120                 125

Val Phe Leu Phe Pro Pro Lys Pro Lys Asp Thr Leu Met Ile Ser Arg
    130                 135                 140

Thr Pro Glu Val Thr Cys Val Val Val Asp Val Ser His Glu Asp Pro
145                 150                 155                 160

Glu Val Lys Phe Asn Trp Tyr Val Asp Gly Val Glu Val His Asn Ala
                165                 170                 175

Lys Thr Lys Pro Arg Glu Glu Gln Tyr Asn Ser Thr Tyr Arg Val Val
            180                 185                 190

Ser Val Leu Thr Val Leu His Gln Asp Trp Leu Asn Gly Lys Glu Tyr
        195                 200                 205

Lys Cys Lys Val Ser Asn Lys Ala Leu Pro Ala Pro Ile Glu Lys Thr
    210                 215                 220

Ile Ser Lys Ala Lys Gly Gln Pro Arg Glu Pro Gln Val Tyr Thr Leu
225                 230                 235                 240

Pro Pro Ser Arg Asp Glu Leu Thr Lys Asn Gln Val Ser Leu Thr Cys
                245                 250                 255

Leu Val Lys Gly Phe Tyr Pro Ser Asp Ile Ala Val Glu Trp Glu Ser
            260                 265                 270

Asn Gly Gln Pro Glu Asn Asn Tyr Lys Thr Thr Pro Pro Val Leu Asp
        275                 280                 285

Ser Asp Gly Ser Phe Phe Leu Tyr Ser Lys Leu Thr Val Asp Lys Ser
    290                 295                 300

Arg Trp Gln Gln Gly Asn Val Phe Ser Cys Ser Val Met His Glu Ala
305                 310                 315                 320

Leu His Asn His Tyr Thr Gln Lys Ser Leu Ser Leu Ser Pro Gly Lys
                325                 330                 335
```

<210> SEQ ID NO 98
<211> LENGTH: 332
<212> TYPE: PRT
<213> ORGANISM: Artificial sequence
<220> FEATURE:
<223> OTHER INFORMATION: Synthetic construct containing Fc domain of IgG2

<400> SEQUENCE: 98

```
Leu Val Thr Val Ser Ser Ala Ser Thr Lys Gly Pro Ser Val Phe Pro
1               5                   10                  15
```

Leu Ala Pro Cys Ser Arg Ser Thr Ser Glu Ser Thr Ala Ala Leu Gly
            20                  25                  30

Cys Leu Val Lys Asp Tyr Phe Pro Glu Pro Val Thr Val Ser Trp Asn
            35                  40                  45

Ser Gly Ala Leu Thr Ser Gly Val His Thr Phe Pro Ala Val Leu Gln
 50                  55                  60

Ser Ser Gly Leu Tyr Ser Leu Ser Ser Val Val Thr Val Thr Ser Ser
65                  70                  75                  80

Asn Phe Gly Thr Gln Thr Tyr Thr Cys Asn Val Asp His Lys Pro Ser
                85                  90                  95

Asn Thr Lys Val Asp Lys Thr Val Glu Arg Lys Cys Cys Val Glu Cys
            100                 105                 110

Pro Pro Cys Pro Ala Pro Pro Val Ala Gly Pro Ser Val Phe Leu Phe
            115                 120                 125

Pro Pro Lys Pro Lys Asp Thr Leu Met Ile Ser Arg Thr Pro Glu Val
            130                 135                 140

Thr Cys Val Val Val Asp Val Ser His Glu Asp Pro Glu Val Gln Phe
145                 150                 155                 160

Asn Trp Tyr Val Asp Gly Val Glu Val His Asn Ala Lys Thr Lys Pro
                165                 170                 175

Arg Glu Glu Gln Phe Asn Ser Thr Phe Arg Val Val Ser Val Leu Thr
            180                 185                 190

Val Val His Gln Asp Trp Leu Asn Gly Lys Glu Tyr Lys Cys Lys Val
            195                 200                 205

Ser Asn Lys Gly Leu Pro Ala Pro Ile Glu Lys Thr Ile Ser Lys Thr
210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Met Leu Asp Ser Asp Gly Ser
            275                 280                 285

Phe Phe Leu Tyr Ser Lys Leu Thr Val Asp Lys Ser Arg Trp Gln Gln
290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330

<210> SEQ ID NO 99
<211> LENGTH: 333
<212> TYPE: PRT
<213> ORGANISM: Artificial sequence
<220> FEATURE:
<223> OTHER INFORMATION: Synthetic construct containing Fc domain of
      IgG4

<400> SEQUENCE: 99

Leu Val Thr Val Ser Ser Ala Ser Thr Lys Gly Pro Ser Val Phe Pro
1               5                   10                  15

Leu Ala Pro Cys Ser Arg Ser Thr Ser Glu Ser Thr Ala Ala Leu Gly
            20                  25                  30

Cys Leu Val Lys Asp Tyr Phe Pro Glu Pro Val Thr Val Ser Trp Asn
            35                  40                  45

Ser Gly Ala Leu Thr Ser Gly Val His Thr Phe Pro Ala Val Leu Gln
            50                  55                  60

Ser Ser Gly Leu Tyr Ser Leu Ser Ser Val Val Thr Val Pro Ser Ser
 65                  70                  75                  80

Ser Leu Gly Thr Lys Thr Tyr Thr Cys Asn Val Asp His Lys Pro Ser
                 85                  90                  95

Asn Thr Lys Val Asp Lys Arg Val Glu Ser Lys Tyr Gly Pro Pro Cys
            100                 105                 110

Pro Ser Cys Pro Ala Pro Glu Phe Leu Gly Gly Pro Ser Val Phe Leu
            115                 120                 125

Phe Pro Pro Lys Pro Lys Asp Thr Leu Met Ile Ser Arg Thr Pro Glu
            130                 135                 140

Val Thr Cys Val Val Val Asp Val Ser Gln Glu Asp Pro Glu Val Gln
145                 150                 155                 160

Phe Asn Trp Tyr Val Asp Gly Val Glu Val His Asn Ala Lys Thr Lys
                165                 170                 175

Pro Arg Glu Glu Gln Phe Asn Ser Thr Tyr Arg Val Val Ser Val Leu
            180                 185                 190

Thr Val Leu His Gln Asp Trp Leu Asn Gly Lys Glu Tyr Lys Cys Lys
            195                 200                 205

Val Ser Asn Lys Gly Leu Pro Ser Ser Ile Glu Lys Thr Ile Ser Lys
210                 215                 220

Ala Lys Gly Gln Pro Arg Glu Pro Gln Val Tyr Thr Leu Pro Pro Ser
225                 230                 235                 240

Gln Glu Glu Met Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
            260                 265                 270

Pro Glu Asn Asn Tyr Lys Thr Thr Pro Pro Val Leu Asp Ser Asp Gly
            275                 280                 285

Ser Phe Phe Leu Tyr Ser Arg Leu Thr Val Asp Lys Ser Arg Trp Gln
            290                 295                 300

Glu Gly Asn Val Phe Ser Cys Ser Val Met His Glu Ala Leu His Asn
305                 310                 315                 320

His Tyr Thr Gln Lys Ser Leu Ser Leu Ser Leu Gly Lys
                325                 330

<210> SEQ ID NO 100
<211> LENGTH: 332
<212> TYPE: PRT
<213> ORGANISM: Artificial sequence
<220> FEATURE:
<223> OTHER INFORMATION: Synthetic construct containing Fc domain of
      IgG2m4

<400> SEQUENCE: 100

Leu Val Thr Val Ser Ser Ala Ser Thr Lys Gly Pro Ser Val Phe Pro
 1               5                  10                  15

Leu Ala Pro Cys Ser Arg Ser Thr Ser Glu Ser Thr Ala Ala Leu Gly
             20                  25                  30

Cys Leu Val Lys Asp Tyr Phe Pro Glu Pro Val Thr Val Ser Trp Asn
             35                  40                  45

Ser Gly Ala Leu Thr Ser Gly Val His Thr Phe Pro Ala Val Leu Gln
             50                  55                  60

Ser Ser Gly Leu Tyr Ser Leu Ser Ser Val Val Thr Val Thr Ser Ser

```
                65                  70                  75                  80
Asn Phe Gly Thr Gln Thr Tyr Thr Cys Asn Val Asp His Lys Pro Ser
                85                  90                  95

Asn Thr Lys Val Asp Lys Thr Val Glu Arg Lys Cys Cys Val Glu Cys
            100                 105                 110

Pro Pro Cys Pro Ala Pro Pro Val Ala Gly Pro Ser Val Phe Leu Phe
            115                 120                 125

Pro Pro Lys Pro Lys Asp Thr Leu Met Ile Ser Arg Thr Pro Glu Val
        130                 135                 140

Thr Cys Val Val Val Asp Val Ser Gln Glu Asp Pro Glu Val Gln Phe
145                 150                 155                 160

Asn Trp Tyr Val Asp Gly Val Glu Val His Asn Ala Lys Thr Lys Pro
                165                 170                 175

Arg Glu Glu Gln Phe Asn Ser Thr Phe Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Gly Leu Pro Ser Ser Ile Glu Lys Thr Ile Ser Lys Thr
210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Met Leu Asp Ser Asp Gly Ser
        275                 280                 285

Phe Phe Leu Tyr Ser Lys Leu Thr Val Asp Lys Ser Arg Trp Gln Gln
        290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330

<210> SEQ ID NO 101
<211> LENGTH: 401
<212> TYPE: PRT
<213> ORGANISM: Homo sapiens

<400> SEQUENCE: 101

Ala Pro Thr Glu Thr Gln Pro Pro Val Thr Asn Leu Ser Val Ser Val
1               5                   10                  15

Glu Asn Leu Cys Thr Val Ile Trp Thr Trp Asn Pro Pro Glu Gly Ala
            20                  25                  30

Ser Ser Asn Cys Ser Leu Trp Tyr Phe Ser His Phe Gly Asp Lys Gln
        35                  40                  45

Asp Lys Lys Ile Ala Pro Glu Thr Arg Arg Ser Ile Glu Val Pro Leu
    50                  55                  60

Asn Glu Arg Ile Cys Leu Gln Val Gly Ser Gln Cys Ser Thr Asn Glu
65                  70                  75                  80

Ser Glu Lys Pro Ser Ile Leu Val Glu Lys Cys Ile Ser Pro Pro Glu
                85                  90                  95

Gly Asp Pro Glu Ser Ala Val Thr Glu Leu Gln Cys Ile Trp His Asn
            100                 105                 110
```

Leu Ser Tyr Met Lys Cys Ser Trp Leu Pro Gly Arg Asn Thr Ser Pro
            115                 120                 125

Asp Thr Asn Tyr Thr Leu Tyr Tyr Trp His Arg Ser Leu Glu Lys Ile
130                 135                 140

His Gln Cys Glu Asn Ile Phe Arg Glu Gly Gln Tyr Phe Gly Cys Ser
145                 150                 155                 160

Phe Asp Leu Thr Lys Val Lys Asp Ser Ser Phe Glu Gln His Ser Val
                165                 170                 175

Gln Ile Met Val Lys Asp Asn Ala Gly Lys Ile Lys Pro Ser Phe Asn
                180                 185                 190

Ile Val Pro Leu Thr Ser Arg Val Lys Pro Asp Pro Pro His Ile Lys
                195                 200                 205

Asn Leu Ser Phe His Asn Asp Asp Leu Tyr Val Gln Trp Glu Asn Pro
210                 215                 220

Gln Asn Phe Ile Ser Arg Cys Leu Phe Tyr Glu Val Glu Val Asn Asn
225                 230                 235                 240

Ser Gln Thr Glu Thr His Asn Val Phe Tyr Val Gln Glu Ala Lys Cys
                245                 250                 255

Glu Asn Pro Glu Phe Glu Arg Asn Val Glu Asn Thr Ser Cys Phe Met
                260                 265                 270

Val Pro Gly Val Leu Pro Asp Thr Leu Asn Thr Val Arg Ile Arg Val
                275                 280                 285

Lys Thr Asn Lys Leu Cys Tyr Glu Asp Asp Lys Leu Trp Ser Asn Trp
                290                 295                 300

Ser Gln Glu Met Ser Ile Gly Lys Lys Arg Asn Ser Thr Leu Tyr Ile
305                 310                 315                 320

Thr Met Leu Leu Ile Val Pro Val Ile Val Ala Gly Ala Ile Ile Val
                325                 330                 335

Leu Leu Leu Tyr Leu Lys Arg Leu Lys Ile Ile Ile Phe Pro Pro Ile
                340                 345                 350

Pro Asp Pro Gly Lys Ile Phe Lys Glu Met Phe Gly Asp Gln Asn Asp
                355                 360                 365

Asp Thr Leu His Trp Lys Lys Tyr Asp Ile Tyr Glu Lys Gln Thr Lys
370                 375                 380

Glu Glu Thr Asp Ser Val Val Leu Ile Glu Asn Leu Lys Lys Ala Ser
385                 390                 395                 400

Gln

<210> SEQ ID NO 102
<211> LENGTH: 17
<212> TYPE: PRT
<213> ORGANISM: Artificial sequence
<220> FEATURE:
<223> OTHER INFORMATION: Synthetic 10G5 VH CDR2

<400> SEQUENCE: 102

Val Ile Tyr Pro Gly Asp Ser Tyr Thr Arg Tyr Ser Pro Ser Phe Gln
1               5                   10                  15

Gly

<210> SEQ ID NO 103
<211> LENGTH: 324
<212> TYPE: PRT
<213> ORGANISM: Homo sapiens

<400> SEQUENCE: 103

Asp Tyr Lys Asp Asp Asp Glu Ser Arg Thr Glu Gln Pro Pro Val
1               5                   10                  15

Thr Asn Leu Ser Val Ser Val Glu Asn Leu Cys Thr Val Ile Trp Thr
        20                  25                  30

Trp Asn Pro Pro Glu Gly Ala Ser Ser Asn Cys Ser Leu Trp Tyr Phe
        35                  40                  45

Ser His Phe Gly Asp Lys Gln Asp Lys Lys Ile Ala Pro Glu Thr Arg
    50                  55                  60

Arg Ser Ile Glu Val Pro Leu Asn Glu Arg Ile Cys Leu Gln Val Gly
65                  70                  75                  80

Ser Gln Cys Ser Thr Asn Glu Ser Glu Lys Pro Ser Ile Leu Val Glu
                85                  90                  95

Lys Cys Ile Ser Pro Pro Glu Gly Asp Pro Glu Ser Ala Val Thr Glu
                100                 105                 110

Leu Gln Cys Ile Trp His Asn Leu Ser Tyr Met Lys Cys Ser Trp Leu
            115                 120                 125

Pro Gly Arg Asn Thr Ser Pro Asp Thr Asn Tyr Thr Leu Tyr Tyr Trp
        130                 135                 140

His Arg Ser Leu Glu Lys Ile His Gln Cys Glu Asn Ile Phe Arg Glu
145                 150                 155                 160

Gly Gln Tyr Phe Gly Cys Ser Phe Asp Leu Thr Lys Val Lys Asp Ser
                165                 170                 175

Ser Phe Glu Gln His Ser Val Gln Ile Met Val Lys Asp Asn Ala Gly
            180                 185                 190

Lys Ile Lys Pro Ser Phe Asn Ile Val Pro Leu Thr Ser Arg Val Lys
        195                 200                 205

Pro Asp Pro Pro His Ile Lys Asn Leu Ser Phe His Asn Asp Asp Leu
    210                 215                 220

Tyr Val Gln Trp Glu Asn Pro Gln Asn Phe Ile Ser Arg Cys Leu Phe
225                 230                 235                 240

Tyr Glu Val Glu Val Asn Asn Ser Gln Thr Glu Thr His Asn Val Phe
                245                 250                 255

Tyr Val Gln Glu Ala Lys Cys Glu Asn Pro Glu Phe Glu Arg Asn Val
            260                 265                 270

Glu Asn Thr Ser Cys Phe Met Val Pro Gly Val Leu Pro Asp Thr Leu
        275                 280                 285

Asn Thr Val Arg Ile Arg Val Lys Thr Asn Lys Leu Cys Tyr Glu Asp
    290                 295                 300

Asp Lys Leu Trp Ser Asn Trp Ser Gln Glu Met Ser Ile Gly Lys Lys
305                 310                 315                 320

Arg Asn Ser Thr

<210> SEQ ID NO 104
<211> LENGTH: 401
<212> TYPE: PRT
<213> ORGANISM: Macaca fascicularis

<400> SEQUENCE: 104

Ala Pro Thr Glu Thr Gln Pro Pro Val Thr Asn Leu Ser Val Ser Val
1               5                   10                  15

Glu Asn Leu Cys Thr Val Ile Trp Thr Trp Asn Pro Pro Glu Gly Ala
            20                  25                  30

Ser Pro Asn Cys Ser Leu Trp Tyr Phe Ser His Phe Gly Asp Lys Gln
        35                  40                  45

```
Asp Lys Lys Leu Ala Pro Glu Thr Arg Arg Ser Lys Glu Val Pro Leu
 50                  55                  60

Asn Glu Lys Ile Cys Leu Gln Val Gly Ser Gln Cys Ser Thr Asn Glu
 65                  70                  75                  80

Ser Glu Lys Pro Ser Ile Leu Val Glu Lys Cys Ile Ser Pro Pro Glu
                 85                  90                  95

Gly Asp Pro Glu Ser Ala Val Thr Glu Leu Gln Cys Ile Trp His Asn
                100                 105                 110

Leu Ser Tyr Met Gln Cys Ser Trp Leu Pro Gly Arg Asn Thr Ser Pro
                115                 120                 125

Asp Thr Asn Tyr Thr Leu Tyr Tyr Trp His Arg Ser Leu Glu Lys Ile
130                 135                 140

Arg Gln Cys Glu Glu Ile Tyr Lys Glu Gly Gln Tyr Phe Gly Cys Ser
145                 150                 155                 160

Phe Asp Leu Thr Lys Val Lys Asp Ser Ser Phe Glu Gln His Ser Val
                165                 170                 175

Gln Ile Met Val Lys Asp Tyr Ala Gly Lys Ile Lys Pro Ser Phe Asn
                180                 185                 190

Ile Val Pro Leu Thr Ser Arg Val Lys Pro Asp Pro Pro His Ile Lys
                195                 200                 205

Asn Leu Ser Phe His Asn Gly Asp Leu His Val Gln Trp Glu Asn Pro
210                 215                 220

Gln Asn Phe Ile Ser Arg Cys Leu Phe Tyr Glu Val Glu Val Asn Asn
225                 230                 235                 240

Ser Gln Thr Glu Thr His Asn Val Phe Ser Val Gln Glu Ala Lys Cys
                245                 250                 255

Gln Asn Pro Glu Phe Glu Arg Asn Val Glu Asn Thr Ser Cys Phe Met
                260                 265                 270

Val Pro Gly Val Leu Pro Asp Thr Leu Asn Thr Val Arg Ile Arg Val
                275                 280                 285

Lys Thr Asn Lys Leu Cys Tyr Glu Asp Asp Lys Leu Trp Ser Asn Trp
290                 295                 300

Ser Gln Glu Met Ser Ile Gly Lys Lys Arg Asn Ser Thr Leu Tyr Ile
305                 310                 315                 320

Thr Met Leu Leu Ile Val Pro Val Ile Val Ala Gly Ala Ile Ile Val
                325                 330                 335

Leu Leu Leu Tyr Leu Lys Arg Leu Lys Ile Ile Phe Pro Pro Ile
                340                 345                 350

Pro Asp Pro Gly Lys Ile Phe Lys Glu Met Phe Gly Asp Gln Asn Asp
                355                 360                 365

Asp Thr Leu His Trp Lys Lys Tyr Asp Ile Tyr Glu Lys Gln Thr Lys
370                 375                 380

Glu Glu Thr Asp Ser Val Val Leu Ile Glu Asn Leu Lys Lys Ala Ser
385                 390                 395                 400

Gln

<210> SEQ ID NO 105
<211> LENGTH: 398
<212> TYPE: PRT
<213> ORGANISM: Mus musculus

<400> SEQUENCE: 105

Thr Glu Val Gln Pro Pro Val Thr Asn Leu Ser Val Ser Val Glu Asn
1               5                   10                  15
```

```
Leu Cys Thr Ile Ile Trp Thr Trp Ser Pro Pro Glu Gly Ala Ser Pro
                20                  25                  30

Asn Cys Thr Leu Arg Tyr Phe Ser His Phe Asp Asp Gln Gln Asp Lys
            35                  40                  45

Lys Ile Ala Pro Glu Thr His Arg Lys Glu Glu Leu Pro Leu Asp Glu
 50                  55                  60

Lys Ile Cys Leu Gln Val Gly Ser Gln Cys Ser Ala Asn Glu Ser Glu
 65                  70                  75                  80

Lys Pro Ser Pro Leu Val Lys Lys Cys Ile Ser Pro Pro Glu Gly Asp
                85                  90                  95

Pro Glu Ser Ala Val Thr Glu Leu Lys Cys Ile Trp His Asn Leu Ser
            100                 105                 110

Tyr Met Lys Cys Ser Trp Leu Pro Gly Arg Asn Thr Ser Pro Asp Thr
        115                 120                 125

His Tyr Thr Leu Tyr Tyr Trp Tyr Ser Ser Leu Glu Lys Ser Arg Gln
    130                 135                 140

Cys Glu Asn Ile Tyr Arg Glu Gly Gln His Ile Ala Cys Ser Phe Lys
145                 150                 155                 160

Leu Thr Lys Val Glu Pro Ser Phe Glu His Gln Asn Val Gln Ile Met
                165                 170                 175

Val Lys Asp Asn Ala Gly Lys Ile Arg Pro Ser Cys Lys Ile Val Ser
            180                 185                 190

Leu Thr Ser Tyr Val Lys Pro Asp Pro Pro His Ile Lys His Leu Leu
        195                 200                 205

Leu Lys Asn Gly Ala Leu Leu Val Gln Trp Lys Asn Pro Gln Asn Phe
    210                 215                 220

Arg Ser Arg Cys Leu Thr Tyr Glu Val Glu Val Asn Asn Thr Gln Thr
225                 230                 235                 240

Asp Arg His Asn Ile Leu Glu Val Glu Glu Asp Lys Cys Gln Asn Ser
                245                 250                 255

Glu Ser Asp Arg Asn Met Glu Gly Thr Ser Cys Phe Gln Leu Pro Gly
            260                 265                 270

Val Leu Ala Asp Ala Val Tyr Thr Val Arg Val Arg Val Lys Thr Asn
        275                 280                 285

Lys Leu Cys Phe Asp Asp Asn Lys Leu Trp Ser Asp Trp Ser Glu Ala
    290                 295                 300

Gln Ser Ile Gly Lys Glu Gln Asn Ser Thr Phe Tyr Thr Thr Met Leu
305                 310                 315                 320

Leu Thr Ile Pro Val Phe Val Ala Val Ala Val Ile Ile Leu Leu Phe
                325                 330                 335

Tyr Leu Lys Arg Leu Lys Ile Ile Ile Phe Pro Pro Ile Pro Asp Pro
            340                 345                 350

Gly Lys Ile Phe Lys Glu Met Phe Gly Asp Gln Asn Asp Asp Thr Leu
        355                 360                 365

His Trp Lys Lys Tyr Asp Ile Tyr Glu Lys Gln Ser Lys Glu Glu Thr
    370                 375                 380

Asp Ser Val Val Leu Ile Glu Asn Leu Lys Lys Ala Ala Pro
385                 390                 395

<210> SEQ ID NO 106
<211> LENGTH: 30
<212> TYPE: DNA
<213> ORGANISM: Artificial sequence
<220> FEATURE:
<223> OTHER INFORMATION: Synthetic VH CDR1
```

<400> SEQUENCE: 106
ggatacagct taccagcta ctggatcggc					30

<210> SEQ ID NO 107
<211> LENGTH: 30
<212> TYPE: DNA
<213> ORGANISM: Artificial sequence
<220> FEATURE:
<223> OTHER INFORMATION: Synthetic VH CDR2

<400> SEQUENCE: 107
gtcatctatc ctggtgactc ttataccaga					30

<210> SEQ ID NO 108
<211> LENGTH: 27
<212> TYPE: DNA
<213> ORGANISM: Artificial sequence
<220> FEATURE:
<223> OTHER INFORMATION: Synthetic VH CDR3

<400> SEQUENCE: 108
ttccccaact ggggctcatt tgactac					27

<210> SEQ ID NO 109
<211> LENGTH: 35
<212> TYPE: DNA
<213> ORGANISM: Artificial sequence
<220> FEATURE:
<223> OTHER INFORMATION: Synthetic VL CDR1

<400> SEQUENCE: 109
agggccagtc agagattagc agcagctact tagcc					35

<210> SEQ ID NO 110
<211> LENGTH: 21
<212> TYPE: DNA
<213> ORGANISM: Artificial sequence
<220> FEATURE:
<223> OTHER INFORMATION: Synthetic VL CDR2

<400> SEQUENCE: 110
ggtgcatcca gcagggccac t					21

<210> SEQ ID NO 111
<211> LENGTH: 15
<212> TYPE: DNA
<213> ORGANISM: Artificial sequence
<220> FEATURE:
<223> OTHER INFORMATION: Synthetic VL CDR3

<400> SEQUENCE: 111
cagcagtatg agacg					15

<210> SEQ ID NO 112
<211> LENGTH: 27
<212> TYPE: DNA
<213> ORGANISM: Artificial sequence
<220> FEATURE:
<223> OTHER INFORMATION: Synthetic 10G5-6 VH CDR3

<400> SEQUENCE: 112
atgcccaact ggggctcact tgaccat					27

<210> SEQ ID NO 113

```
<211> LENGTH: 15
<212> TYPE: DNA
<213> ORGANISM: Artificial sequence
<220> FEATURE:
<223> OTHER INFORMATION: Synthetic VL CDR3

<400> SEQUENCE: 113
cagcagtatg cttcg                                                      15

<210> SEQ ID NO 114
<211> LENGTH: 20
<212> TYPE: DNA
<213> ORGANISM: Artificial sequence
<220> FEATURE:
<223> OTHER INFORMATION: Synthetic PCR primer
<220> FEATURE:
<221> NAME/KEY: misc_feature
<222> LOCATION: (19)..(19)
<223> OTHER INFORMATION: Y denotes C or T

<400> SEQUENCE: 114
ggggtcaacc gccatcctyg                                                 20

<210> SEQ ID NO 115
<211> LENGTH: 24
<212> TYPE: DNA
<213> ORGANISM: Artificial sequence
<220> FEATURE:
<223> OTHER INFORMATION: Synthetic PCR primer

<400> SEQUENCE: 115
gtctccttcc tcatcttcct gccc                                            24

<210> SEQ ID NO 116
<211> LENGTH: 23
<212> TYPE: DNA
<213> ORGANISM: Artificial sequence
<220> FEATURE:
<223> OTHER INFORMATION: Synthetic PCR primer

<400> SEQUENCE: 116
cccatcggtc ttccccctgg cac                                             23

<210> SEQ ID NO 117
<211> LENGTH: 24
<212> TYPE: DNA
<213> ORGANISM: Artificial sequence
<220> FEATURE:
<223> OTHER INFORMATION: Synthetic PCR primer
<220> FEATURE:
<221> NAME/KEY: misc_feature
<222> LOCATION: (1)..(1)
<223> OTHER INFORMATION: Y denotes C or T

<400> SEQUENCE: 117
ytcttcctcc tgctactctg gctc                                            24

<210> SEQ ID NO 118
<211> LENGTH: 24
<212> TYPE: DNA
<213> ORGANISM: Artificial sequence
<220> FEATURE:
<223> OTHER INFORMATION: Synthetic PCR primer

<400> SEQUENCE: 118
atggtgttgc agacccaggt cttc                                            24
```

```
<210> SEQ ID NO 119
<211> LENGTH: 32
<212> TYPE: DNA
<213> ORGANISM: Artificial sequence
<220> FEATURE:
<223> OTHER INFORMATION: Synthetic PCR primer

<400> SEQUENCE: 119
gaaatctgga actgcctctg ttgtgtgcct gc                                    32

<210> SEQ ID NO 120
<211> LENGTH: 401
<212> TYPE: PRT
<213> ORGANISM: Artificial sequence
<220> FEATURE:
<223> OTHER INFORMATION: Synthetic IL-13alpha receptor 1 polypeptide

<400> SEQUENCE: 120
```

Ala Pro Thr Glu Thr Gln Pro Pro Val Thr Asn Leu Ser Val Ser Val
1               5                   10                  15

Glu Asn Leu Cys Thr Val Ile Trp Thr Trp Asn Pro Pro Glu Gly Ala
            20                  25                  30

Ser Ser Asn Cys Ser Leu Trp Tyr Phe Ser His Phe Gly Asp Lys Gln
        35                  40                  45

Asp Lys Lys Ile Ala Pro Glu Thr Arg Arg Ser Ile Glu Val Pro Leu
    50                  55                  60

Asn Glu Arg Ile Cys Leu Gln Val Gly Ser Gln Cys Ser Thr Asn Glu
65                  70                  75                  80

Ser Glu Lys Pro Ser Ile Leu Val Glu Lys Cys Ile Ser Pro Pro Glu
                85                  90                  95

Gly Asp Pro Glu Ser Ala Val Thr Glu Leu Gln Cys Ile Trp His Asn
            100                 105                 110

Leu Ser Tyr Met Lys Cys Ser Trp Leu Pro Gly Arg Asn Thr Ser Pro
        115                 120                 125

Asp Thr Asn Tyr Thr Leu Tyr Tyr Trp His Arg Ser Leu Glu Lys Ile
    130                 135                 140

His Gln Cys Glu Asn Ile Phe Arg Glu Gly Gln Tyr Phe Gly Cys Ser
145                 150                 155                 160

Phe Asp Leu Thr Lys Val Lys Asp Ser Ser Phe Glu Gln His Ser Val
                165                 170                 175

Gln Ile Met Val Lys Asp Asn Ala Gly Lys Ile Lys Pro Ser Phe Asn
            180                 185                 190

Ile Val Pro Leu Thr Ser Arg Val Lys Pro Asp Pro Pro His Ile Lys
        195                 200                 205

Asn Leu Ser Phe His Asn Asp Asp Leu Tyr Val Gln Trp Glu Asn Pro
    210                 215                 220

Gln Asn Phe Ile Ser Arg Cys Leu Ala Tyr Glu Val Glu Val Asn Asn
225                 230                 235                 240

Ser Gln Thr Glu Thr His Asn Val Phe Tyr Val Gln Glu Ala Lys Cys
                245                 250                 255

Glu Asn Pro Glu Phe Glu Arg Asn Val Glu Asn Thr Ser Cys Phe Met
            260                 265                 270

Val Pro Gly Val Leu Pro Asp Thr Leu Asn Thr Val Arg Ile Arg Val
        275                 280                 285

Lys Thr Asn Lys Leu Cys Tyr Glu Asp Asp Lys Leu Trp Ser Asn Trp
    290                 295                 300

Ser Gln Glu Met Ser Ile Gly Lys Lys Arg Asn Ser Thr Leu Tyr Ile

```
                305                 310                 315                 320

Thr Met Leu Leu Ile Val Pro Val Ile Val Ala Gly Ala Ile Ile Val
                325                 330                 335

Leu Leu Leu Tyr Leu Lys Arg Leu Lys Ile Ile Phe Pro Pro Ile
                340                 345                 350

Pro Asp Pro Gly Lys Ile Phe Lys Glu Met Phe Gly Asp Gln Asn Asp
        355                 360                 365

Asp Thr Leu His Trp Lys Lys Tyr Asp Ile Tyr Glu Lys Gln Thr Lys
    370                 375                 380

Glu Glu Thr Asp Ser Val Val Leu Ile Glu Asn Leu Lys Lys Ala Ser
385                 390                 395                 400

Gln

<210> SEQ ID NO 121
<211> LENGTH: 9
<212> TYPE: PRT
<213> ORGANISM: Artificial sequence
<220> FEATURE:
<223> OTHER INFORMATION: Synthetic VH CDR3
<220> FEATURE:
<221> NAME/KEY: MISC_FEATURE
<222> LOCATION: (1)..(1)
<223> OTHER INFORMATION: Xaa denotes Phe, Met, Gln, Leu or Val
<220> FEATURE:
<221> NAME/KEY: MISC_FEATURE
<222> LOCATION: (6)..(6)
<223> OTHER INFORMATION: Xaa denotes Ser or Ala
<220> FEATURE:
<221> NAME/KEY: MISC_FEATURE
<222> LOCATION: (7)..(7)
<223> OTHER INFORMATION: Xaa denotes Phe, Leu, Ala or Met
<220> FEATURE:
<221> NAME/KEY: MISC_FEATURE
<222> LOCATION: (9)..(9)
<223> OTHER INFORMATION: Xaa denotes Tyr, Gln, Lys, Arg, Trp, His, Ala,
      Thr, Ser, Asn or Gly

<400> SEQUENCE: 121

Xaa Pro Asn Trp Gly Xaa Xaa Asp Xaa
1               5

<210> SEQ ID NO 122
<211> LENGTH: 5
<212> TYPE: PRT
<213> ORGANISM: Artificial sequence
<220> FEATURE:
<223> OTHER INFORMATION: Synthetic VL CDR3
<220> FEATURE:
<221> NAME/KEY: MISC_FEATURE
<222> LOCATION: (2)..(2)
<223> OTHER INFORMATION: Xaa denotes Gln, Arg, Met, Ser, Thr or Val.
<220> FEATURE:
<221> NAME/KEY: MISC_FEATURE
<222> LOCATION: (3)..(3)
<223> OTHER INFORMATION: Xaa denotes Tyr or Val.
<220> FEATURE:
<221> NAME/KEY: MISC_FEATURE
<222> LOCATION: (4)..(4)
<223> OTHER INFORMATION: Xaa denotes Glu, Ala, Gly or Ser.
<220> FEATURE:
<221> NAME/KEY: MISC_FEATURE
<222> LOCATION: (5)..(5)
<223> OTHER INFORMATION: Xaa denotes Thr, Ala or Ser.

<400> SEQUENCE: 122

Gln Xaa Xaa Xaa Xaa
1               5
```

```
<210> SEQ ID NO 123
<211> LENGTH: 36
<212> TYPE: DNA
<213> ORGANISM: Artificial sequence
<220> FEATURE:
<223> OTHER INFORMATION: Synthetic VL CDR1

<400> SEQUENCE: 123
agggccagtc agagtattag cagcagctac ttagcc                              36
```